us005556946A

United States Patent [19]

Fujisawa et al.

[11] Patent Number: 5,556,946

[45] Date of Patent: Sep. 17, 1996

[54] INTERLEUKIN-2/VIRAL ANTIGEN PROTEIN CHIMERS

[75] Inventors: Yukio Fujisawa, Hyogo; Shuji Hinuma, Osaka; Aki Aono, Shiga, all of Japan

[73] Assignee: Takeda Chemical Industries, Ltd., Osaka, Japan

[21] Appl. No.: 386,354

[22] Filed: Feb. 8, 1995

Related U.S. Application Data

[63] Continuation of Ser. No. 86,429, Jun. 30, 1993, abandoned, which is a continuation of Ser. No. 548,509, Jul. 2, 1990, abandoned.

[30] Foreign Application Priority Data

| Jul. 7, 1989 | [JP] | Japan | 1-176036 |
| Mar. 6, 1990 | [JP] | Japan | 2-52816 |
| Apr. 11, 1990 | [JP] | Japan | 2-93938 |
| May 30, 1990 | [JP] | Japan | 2-138180 |

[51] Int. Cl.$^6$ .......... A61K 38/20; C07K 14/55; C12N 15/62
[52] U.S. Cl. .......... 530/351; 435/69.52; 435/69.7; 530/395; 530/403; 536/23.4
[58] Field of Search .......... 435/69.52, 69.7; 514/2; 530/351, 395, 403; 536/23.4

[56] References Cited

FOREIGN PATENT DOCUMENTS

| 1150126 | 7/1985 | European Pat. Off. . |
| 0158198 | 10/1985 | European Pat. Off. . |
| 1225701 | 6/1987 | European Pat. Off. . |
| 0319012 | 6/1989 | European Pat. Off. . |
| 0369316 | 5/1990 | European Pat. Off. . |
| 0396387 | 11/1990 | European Pat. Off. . |
| 07/00971 | 2/1988 | WIPO . |
| 88/02634 | 8/1988 | WIPO . |
| 89/01041 | 2/1989 | WIPO . |
| 9101004 | 1/1991 | WIPO . |

OTHER PUBLICATIONS

Weinberg et al., *Journal of Immunology*, 140:1, pp. 294–299 (1988).

R. Seno et al., *FEBS*, 199:2, pp. 187–192 (1986).

*Primary Examiner*—Garnette D. Draper
*Assistant Examiner*—John D. Ulm
*Attorney, Agent, or Firm*—David G. Conlin; Linda M. Buckley

[57] ABSTRACT

Disclosed are (1) a fused protein obtained by combining an antigen used for vaccine and a lymphokine by the application of gene engineering, (2) a recombinant DNA containing a nucleotide sequence coding for the above fused protein, (3) a transformant bearing the above recombinant DNA, (4) a method for producing the fused protein which comprises cultivating the above transformant, producing and accumulating the above fused protein in a culture, and collecting the fused protein, and (5) a hybrid protein obtained by chemically combining an antigen used for vaccine with a lymphokine. The resulting fused and hybrid proteins have strong immunogenicity.

20 Claims, 38 Drawing Sheets

```
  1  Met Gly Gly Ala Ala Ala Arg Leu Gly Ala Val Ile Leu Phe Val Val
 17  Ile Val Gly Leu His Gly Val Arg Gly Lys Tyr Ala Leu Ala Asp Ala
 33  Ser Leu Lys Met Ala Asp Pro Asn Arg Phe Arg Gly Lys Asp Leu Pro
 49  Val Leu Asp Pro Leu Thr Asp Pro Pro Gly Val Arg Arg Val Tyr His
 65  Ile Gln Ala Gly Leu Pro Asp Pro Phe Gln Pro Pro Ser Leu Pro Ile
 81  Thr Val Tyr Tyr Ala Val Leu Glu Arg Ala Cys Arg Ser Val Leu Leu
 97  Asn Ala Pro Ser Glu Ala Pro Gln Ile Val Arg Gly Ala Ser Glu Asp
113  Val Arg Lys Gln Pro Tyr Asn Leu Thr Ile Ala Trp Phe Arg Met Gly
129  Gly Asn Cys Ala Ile Pro Ile Thr Val Met Glu Tyr Thr Glu Cys Ser
145  Tyr Asn Lys Ser Leu Gly Ala Cys Pro Ile Arg Thr Gln Pro Arg Trp
161  Asn Tyr Tyr Asp Ser Phe Ser Ala Val Ser Glu Asp Asn Leu Gly Phe
177  Leu Met His Ala Pro Ala Phe Glu Thr Ala Gly Thr Tyr Leu Arg Leu
193  Val Lys Ile Asn Asp Trp Thr Glu Ile Thr Gln Phe Ile Leu Glu His
209  Arg Ala Lys Gly Ser Cys Lys Tyr Ala Leu Pro Leu Arg Ile Pro Pro
225  Ser Ala Cys Leu Ser Pro Gln Ala Tyr Gln Gln Gly Val Thr Val Asp
241  Ser Ile Gly Met Leu Pro Arg Phe Ile Pro Glu Asn Gln Arg Thr Val
257  Ala Val Tyr Ser Leu Lys Ile Ala Gly Trp His Gly Pro Lys Ala Pro
273  Tyr Thr Ser Thr Leu Leu Pro Pro Glu Leu Ser Glu Thr Pro Asn Ala
289  Thr Gln Pro Glu Leu Ala Pro Glu Asp Pro Glu Asp Ser Ala Leu Leu
305  Glu Asp Pro Val Gly Thr Val Ala Pro Gln Ile Pro Pro Asn Trp His
321  Ile Pro Ser Ile Gln Asp Ala Ala Thr Pro Tyr His Pro Pro Ala Thr
337  Pro Asn Asn Met Gly Leu Ile Ala Gly Ala Val Gly Gly Ser Leu Leu
353  Ala Ala Leu Val Ile Cys Gly Ile Val Tyr Trp Met His Arg Arg Thr
369  Arg Lys Ala Pro Lys Arg Ile Arg Leu Pro His Ile Arg Glu Asp Asp
385  Gln Pro Ser Ser His Gln Pro Leu Phe Tyr
```

FIG.1

```
   1  TTT AAA AAG CAG GGG TTA GGG AGT TGT TCG GTC ATA AGC TTC AGC
  46  GCG AAC GAC CAA CTA CCC CGA TCA TCA GTT ATC CTT AAG GTC TCT
  91  TTT GTG TGG TGC GTT CCG GTA TGG GGG GGG CTG CCG CCA GGT TGG
 136  GGG CCG TGA TTT TGT TTG TCG TCA TAG TGG GCC TCC ATG GGG TCC
 181  GCG GCA AAT ATG CCT TGG CGG ATG CCT CTC TCA AGA TGG CCG ACC
 226  CCA ATC GCT TTC GCG GCA AAG ACC TTC CGG TCC TGG ACC CGC TGA
 271  CCG ACC CTC CGG GGG TCC GGC GCG TGT ACC ACA TCC AGG CGG GCC
 316  TAC CGG ACC CGT TCC AGC CCC CCA GCC TCC CGA TCA CGG TTT ACT
 361  ACG CCG TGT TGG AGC GCG CCT GCC GCA GCG TGC TCC TAA ACG CAC
 406  CGT CGG AGG CCC CCC AGA TTG TCC GCG GGG CCT CCG AAG ACG TCC
 451  GGA AAC AAC CCT ACA ACC TGA CCA TCG CTT GGT TTC GGA TGG GAG
 496  GCA ACT GTG CTA TCC CCA TCA CGG TCA TGG AGT ACA CCG AAT GCT
 541  CCT ACA ACA AGT CTC TGG GGG CCT GTC CCA TCC GAA CGC AGC CCC
 586  GCT GGA ACT ACT ATG ACA GCT TCA GCG CCG TCA GCG AGG ATA ACC
 631  TGG GGT TCC TGA TGC ACG CCC CCG CGT TTG AGA CCG CCG GCA CGT
 676  ACC TGC GGC TCG TGA AGA TAA ACG ACT GGA CGG AGA TTA CAC AGT
 721  TTA TCC TGG AGC ACC GAG CCA AGG GCT CCT GTA AGT ACG CCC TCC
 766  CGC TGC GCA TCC CCC CGT CAG CCT GCC TCT CCC CCC AGG CCT ACC
 811  AGC AGG GGG TGA CGG TGG ACA GCA TCG GGA TGC TGC CCC GCT TCA
 856  TCC CCG AGA ACC AGC GCA CCG TCG CCG TAT ACA GCT TGA AGA TCG
 901  CCG GGT GGC ACG GGC CCA AGG CCC CAT ACA CGA GCA CCC TGC TGC
 946  CCC CTG AGC TGT CCG AGA CCC CCA ACG CCA CGC AGC CAG AAC TCG
 991  CCC CGG AAG ACC CCG AGG ATT CGG CCC TCT TGG AGG ACC CCG TGG
1036  GGA CGG TGG CGC CGC AAA TCC CAC CAA ACT GGC ACA TCC CGT CGA
1081  TCC AGG ACG CCG CGA CGC CTT ACC ATC CCC CGG CCA CCC CGA ACA
1126  ACA TGG CCC TGA TCG CCG GCG CGG TGG GCG GCA GTC TCC TGG CAG
1171  CCC TGG TCA TTT GCG GAA TTG TGT ACT GGA TGC ACC GCC GCA CTC
1216  GGA AAG CCC CAA AGC GCA TAC GCC TCC CCA CAT CCG GGA AGA CG
1261  ACC AGC CGT CCT CGC ACC AGC CCT TGT TTT ACT AGA TAC CCC CCC
1306  TTA ATG GGT GCG GGG GGG TCA GGT CTG CGG GGT TGG GAT GGG ACC
1351  TTA ACT CCA TAC AAA GCG AGT CTG GAA GGG GGG AAA GGC GGA CAG
1396  TCG ATA AGT CGG TAG CGG GGG ACG CGC ACC TGT TCC GCC TGT CGC
1441  ACC CAC AGC TTT TTC GCG A
```

FIG.2

```
                                                                    Ala Pro
Ser Ser Pro Gly Thr Pro Gly Val Ala Ala Ala Thr Gln Ala Ala Asn
Gly Gly Pro Ala Thr Pro Ala Pro Pro Ala Pro Gly Pro Ala Pro Thr
Gly Asp Thr Lys Pro Lys Lys Asn Lys Lys Pro Lys Asn Pro Pro Pro
Pro Arg Pro Ala Gly Asp Asn Ala Thr Val Ala Ala Gly His Ala Thr
Leu Arg Glu His Leu Arg Asp Ile Lys Ala Lys Asn Thr Asp Ala Asn
Phe Tyr Val Cys Pro Pro Pro Thr Gly Ala Thr Val Val Gln Phe Glu
Gln Pro Arg Arg Cys Pro Thr Arg Pro Glu Gly Gln Asn Tyr Thr Glu
Gly Ile Ala Val Val Phe Lys Glu Asn Ile Ala Pro Tyr Lys Phe Lys
Ala Thr Met Tyr Tyr Lys Asp Val Thr Val Ser Gln Val Trp Phe Gly
His Arg Tyr Ser Gln Phe Met Gly Ile Phe Glu Asp Arg Ala Pro Val
Pro Phe Glu Glu Val Ile Asp Lys Ile Asn Ala Lys Gly Val Cys Arg
Ser Thr Ala Lys Tyr Val Arg Asn Asn Leu Glu Thr Thr Ala Phe His
Arg Asp Asp His Glu Thr Asp Met Glu Leu Lys Pro Ala Asn Ala Ala
Thr Arg Thr Ser Arg Gly Trp His Thr Thr Asp Leu Lys Tyr Asn Pro
Ser Arg Val Glu Ala Phe His Arg Tyr Gly Thr Thr Val Asn Cys Ile
Val Glu Glu Val Asp Ala Arg Ser Val Tyr Pro Tyr Asn Glu Phe Val
Leu Ala Thr Gly Asp Phe Val Tyr Met Ser Pro Phe Tyr Gly Tyr Arg
Glu Gly Ser His Thr Glu His Thr Ser Tyr Ala Ala Asp Arg Phe Lys
Gln Val Asp Gly Phe Tyr Ala Arg Asp Leu Thr Thr Lys Ala Arg Ala
Thr Ala Pro Thr Thr Arg Asn Leu Leu Thr Thr Pro Lys Phe Thr Val
Ala Trp Asp Trp Val Pro Lys Arg Pro Ser Val Cys Thr Met Thr Lys
Trp Gln Glu Val Asp Glu Met Leu Arg Ser Glu Tyr Gly Gly Ser Phe
Arg Phe Ser Ser Asp Ala Ile Ser Thr Thr Phe Thr Thr Asn Leu Thr
Glu Tyr Pro Leu Ser Arg Val Asp Leu Gly Asp Cys Ile Gly Lys Asp
Ala Arg Asp Ala Met Asp Arg Ile Phe Ala Arg Arg Tyr Asn Ala Thr
His Ile Lys Val Gly Gln Pro Gln Tyr Tyr Leu Ala Asn Gly Gly Phe
Leu Ile Ala Tyr Gln Pro Leu Leu Ser Asn Thr Leu Ala Glu Leu Tyr
```

FIG. 3A

```
Val Arg Glu His Leu Arg Glu Gln Ser Arg Lys Pro Pro Asn Pro Thr
Pro Pro Pro Pro Gly Ala Ser Ala Asn Ala Ser Val Glu Arg Ile Lys
Thr Thr Ser Ser Ile Glu Phe Ala Arg Leu Gln Phe Thr Tyr Asn His
Ile Gln Arg His Val Asn Asp Met Leu Gly Arg Val Ala Ile Ala Trp
Cys Glu Leu Gln Asn His Glu Leu Thr Leu Trp Asn Glu Ala Arg Lys
Leu Asn Pro Asn Ala Ile Ala Ser Val Thr Val Gly Arg Arg Val Ser
Ala Arg Met Leu Gly Asp Val Met Ala Val Ser Thr Cys Val Pro Val
Ala Ala Asp Asn Val Ile Val Gln Asn Ser Met Arg Ile Ser Ser Arg
Pro Gly Ala Cys Tyr Ser Arg Pro Leu Val Ser Phe Arg Tyr Glu Asp
Gln Gly Pro Leu Val Glu Gly Gln Leu Gly Glu Asn Asn Glu Leu Arg
Leu Thr Arg Asp Ala Ile Glu Pro Cys Thr Val Gly His Arg Arg Tyr
Phe Thr Phe Gly Gly Gly Tyr Val Tyr Phe Glu Glu Tyr Ala Tyr Ser
His Gln Leu Ser Arg Ala Asp Ile Thr Thr Val Ser Thr Phe Ile Asp
Leu Asn Ile Thr Met Leu Glu Asp His Glu Phe Val Pro Leu Glu Val
Tyr Thr Arg His Glu Ile Lys Asp Ser Gly Leu Leu Asp Tyr Thr Glu
Val Gln Arg Arg Asn Gln Leu His Asp Leu Arg Phe Ala Asp Ile Asp
Thr Val Ile His Ala Asp Ala Asn Ala Ala Met Phe Ala Gly Leu Gly
Ala Phe Phe Glu Gly Met Gly Asp Leu Gly Arg Ala Val Gly Lys Val
Val Met Gly Ile Val Gly Gly Val Val Ser Ala Val Ser Gly Val Ser
Ser Phe Met Ser Asn Pro Phe Gly Ala Leu Ala Val Gly Leu Leu Val
Leu Ala Gly Leu Ala Ala Ala Phe Phe Ala Phe Arg Tyr Val Met Arg
Leu Gln Ser Asn Pro Met Lys Ala Leu Tyr Pro Leu Thr Thr Lys Glu
Leu Lys Asn Pro Thr Asn Pro Asp Ala Ser Gly Glu Gly Glu Glu Gly
Gly Asp Phe Asp Glu Ala Lys Leu Ala Glu Ala Arg Glu Met Ile Arg
Tyr Met Ala Leu Val Ser Ala Met Glu His Thr Glu His Lys Ala Lys
Lys Lys Gly Thr Ser Ala Leu Leu Ser Ala Lys Val Thr Asp Met Val
Met Arg Lys Arg Arg Asn Thr Asn Tyr Thr Gln Val Pro Asn Lys Asp
Ser Asp Ala Asp Glu Asp Asp Leu
```

FIG.3B

```
1                                          GAGTTGCGCCGCCCG    15
GACTGCAGCCGCCCGACCTCCGAAGGTCGTTACCGTTACCCGCCCGGCGTAT          67
ATCTCACGTACGACTCCGACTGTCCGCTGGTGGCCATCGTCGAGAGCGCCCC         119
CGACGGCTGTATCGGCCCCCGGTCGGTCGTGGTCTACGACCGAGACGTTTTC         171
TCGATCCTCTACTCGGTCCTCCAGCACCTCGCCCCCAGGCTACCTGACGGGG         223
GGCACGACGGGCCCCCGTAGTCCCGCC ATG CGC CAG GGC GCC CCC GCG      271
CGG GGG TGC CGG TGG TTC GTC GTA TGG GCG CTC TTG GGG TTG ACG  316
CTG GGG GTC CTG GTG GCG TCG GCG GCT CCG AGT TCC CCC GGC ACG  361
CCT GGG GTC GCG GCC GCG ACC CAG GCG GCG AAC GGG GGA CCT GCC  406
ACT CCG GCG CCG CCC GCC CCT GGC CCC GCC CCA ACG GGG GAC ACG  451
AAA CCG AAG AAG AAC AAA AAA CCG AAA AAC CCA CCG CCG CCG CGC  496
CCC GCC GGC GAC AAC GCG ACC GTC GCC GCG GGC CAC GCC ACC CTG  541
CGC GAG CAC CTG CGG GAC ATC AAG GCG AAG AAC ACC GAT GCA AAC  586
TTT TAC GTG TGC CCA CCC CCC ACG GGC GCC ACG GTG GTG CAG TTC  631
GAG CAG CCG CGC CGC TGC CCG ACC CGG CCC GAG GGT CAG AAC TAC  676
ACG GAG GGC ATC GCG GTG GTC TTC AAG GAG AAC ATC GCC CCG TAC  721
AAG TTC AAG GCC ACC ATG TAC TAC AAA GAC GTC ACC GTT TCG CAG  766
GTG TGG TTC GGC CAC CGC TAC TCC CAG TTT ATG GGG ATC TTT GAG  811
GAC CGC GCC CCC GTC CCC TTC GAG GAG GTG ATC GAC AAG ATC AAC  856
GCC AAG GGG GTC TGT CGG TCC ACG GCC AAG TAC GTG CGC AAC AAC  901
CTG GAG ACC ACC GCG TTT CAC CGG GAC GAC CAC GAG ACC GAC ATG  946
GAG CTG AAA CCG GCC AAC GCC GCG ACC CGC ACG AGC CGG GGC TGG  991
CAC ACC ACC GAC CTC AAG TAC AAC CCC TCG CGG GTG GAG GCG TTC 1036
CAC CGG TAC GGG ACG ACG GTA AAC TGC ATC GTC GAG GAG GTG GAC 1081
GCG CGC TCG GTG TAC CCG TAC AAC GAG TTT GTG CTG GCG ACT GGC 1126
GAC TTT GTG TAC ATG TCC CCG TTT TAC GGC TAC CGG GAG GGG TCG 1171
CAC ACC GAA CAC ACC AGC TAC GCC GCC GAC CGC TTC AAG CAG GTC 1216
GAC GGC TTC TAC GCG CGC GAC CTC ACC ACC AAG GCC CGG GCC ACG 1261
```

FIG. 4A

```
GCG CCG ACC ACC CGG AAC CTG CTC ACG ACC CCC AAG TTC ACC GTG 1306
GCC TGG GAC TGG GTG CCA AAG CGC CCG TCG GTC TGC ACC ATG ACC 1351
AAG TGG CAG GAG GTG GAC GAG ATG CTG CGC TCC GAG TAC GGC GGC 1396
TCC TTC CGA TTC TCC TCC GAC GCC ATA TCC ACC ACC TTC ACC ACC 1441
AAC CTG ACC GAG TAC CCG CTC TCG CGC GTG GAC CTG GGG GAC TGC 1486
ATC GGC AAG GAC GCC CGC GAC GCC ATG GAC CGC ATC TTC GCC CGC 1531
AGG TAC AAC GCG ACG CAC ATC AAG GTG GGC CAG CCG CAG TAC TAC 1576
CTG GCC AAT GGG GGC TTT CTG ATC GCG TAC CAG CCC CTT CTC AGC 1621
AAC ACG CTC GCG GAG CTG TAC GTG CGG GAA CAC CTC CGA GAG CAG 1666
AGC CGC AAG CCC CCA AAC CCC ACG CCC CCG CCG CCC GGG GCC AGC 1711
GCC AAC GCG TCC GTG GAG CGC ATC AAG ACC ACC TCC TCC ATC GAG 1756
TTC GCC CGG CTG CAG TTT ACG TAC AAC CAC ATA CAG CGC CAT GTC 1801
AAC GAT ATG TTG GGC CGC GTT GCC ATC GCG TGG TGC GAG CTG CAG 1846
AAT CAC GAG CTG ACC CTG TGG AAC GAG GCC CGC AAG CTG AAC CCC 1891
AAC GCC ATC GCC TCG GTC ACC GTG GGC CGG CGG GTG AGC GCG CGG 1936
ATG CTC GGC GAC GTG ATG GCC GTC TCC ACG TGC GTG CCG GTC GCC 1981
GCG GAC AAC GTG ATC GTC CAA AAC TCG ATG CGC ATC AGC TCG CGG 2026
CCC GGG GCC TGC TAC AGC CGC CCC CTG GTC AGC TTT CGG TAC GAA 2071
GAC CAG GGC CCG TTG GTC GAG GGG CAG CTG GGG GAG AAC AAC GAG 2116
CTG CGG CTG ACG CGC GAT GCG ATC GAG CCG TGC ACC GTG GGA CAC 2161
CGG CGC TAC TTC ACC TTC GGT GGG GGC TAC GTG TAC TTC GAG GAG 2206
TAC GCG TAC TCC CAC CAG CTG AGC CGC GCC GAC ATC ACC ACC GTC 2251
AGC ACC TTC ATC GAC CTC AAC ATC ACC ATG CTG GAG GAT CAC GAG 2296
TTT GTC CCC CTG GAG GTG TAC ACC CGC CAC GAG ATC AAG GAC AGC 2341
GGC CTG CTG GAC TAC ACG GAG GTC CAG CGC CGC AAC CAG CTG CAC 2386
GAC CTG CGC TTC GCC GAC ATC GAC ACG GTC ATC CAC GCC GAC GCC 2431
AAC GCC GCC ATG TTC GCG GGC CTG GGC GCG TTC TTC GAG GGG ATG 2476
GGC GAC CTG GGG CGT GCG GTC GGC AAG GTG GTG ATG GGC ATC GTG 2521
```

FIG. 4B

```
GGC GGC GTG GTA TCG GCC GTG TCG GGC GTG TCC TCC TTC ATG TCC  2566
AAC CCC TTT GGG GCG CTG GCC GTG GGT CTG TTG GTC CTG GCC GGC  2611
CTG GCG GCG GCC TTC TTC GCC TTT CGC TAC GTC ATG CGG CTG CAG  2656
AGC AAC CCC ATG AAG GCC CTG TAC CCG CTA ACC ACC AAG GAG CTC  2701
AAG AAC CCC ACC AAC CCG GAC GCG TCC GGG GAG GGC GAG GAG GGC  2746
GGC GAC TTT GAC GAG GCC AAG CTA GCC GAG GCC CGG GAG ATG ATA  2791
CGG TAC ATG GCC CTG GTG TCG GCC ATG GAG CAC ACG GAA CAC AAG  2836
GCC AAG AAG AAG GGC ACG AGC GCG CTG CTT AGC GCC AAG GTC ACC  2881
GAC ATG GTC ATG CGC AAG CGC CGC AAC ACC AAC TAC ACC CAA GTT  2926
                                                    Stop
CCC AAC AAA GAC AGT GAC GCC GAC GAG GAC GAC CTG TGA CGGGGG   2971
GTTTGTTGTAAATAAAAACCACGGGTGTTAAACCGCATGCGCATCTTTTGGT        3023
TTTTTTTTTGTACGCCCTTTGTGTGTGTGGGAAGAAAGAAAAAGGAACACA         3075
TAAACTCCCCCGGGTGTCCGCGGCCTGTTTCCTCTTTCCTTTCCCGTGACAA        3127
AACTGACCCCCTTGGTCAGTGCCGATTCCCCCCCCCCCCCCACGCCTTCCT         3179
CCACGTCGAAGGCTTTTGTATTGTAAAGCTACCCGCCTACCCGCGCCTCCCA        3231
ATAAAAAAAAAAGAACATACACCAATGGGTCTTATTTGGTATTACCTGGTT         3283
TATTTAAAAAGATATACAGTAAGACATCCCATGGTACCAAAGACCGGGGCGA        3335
ATCAGCGGGCCCCCATCATCTGAGAGACGAACAAATCGGCGGCGCGGGCCGT        3387
GTCAACGTCCACGTGTGCTGCGCTGCTGGCGTTGACAAGGGCCCCGGCCTCC        3439
GCGTTGGATGCCTCCGGTTGGGATCC                                  3465
```

FIG. 4C

```
  1-GTCAACGGGCCCCTCTTTGATCACTCACCCACAGCTTCGCCCACCACAGCCCCCAACACCGCGTGTATTACAGCGTGAGAACGTGGGCTCCTGCGCACC
101-TGAAGGAGGAGCTGCCCGGTTCATCATGGGGGCGGGGGCTCGGGTGCTGATTGGCCCGTCAGCGAATTCAGAGGTTTACTGTTTGACGGCATTTC
201-CGGAATAACGCCCACTCAGCCGCCGCCTGGCAGCTGATTATCGCCGAGCTGTTACCGTCGTGGTCGTTACCGCCACACTCTTTGCCTCGGTCTACGGTGCGGGGAGCTCGAG
301-TTGCGCGCCCGGACTGCAGCCCGCCCCGACTCCGAAGGTCGTTACCGTCGGTCGTGGTGTCTACGACGCCGACGTATATCTCACGTACGACTCCGCGTGGCCA
401-TCGTCGAGAGCGCCCCGACGGCTGTATCGGCCCCCCGTCGTACGACGCCGACGTTTCTCGATCCTCTACTCGGTCCTCCAGCACCTCGC
501-CCCCAGGCTACCTGACGGGGGGCACGACGGGCCCCCGTAGTCCCGCC ATG CAC CAG GGC GCC CTC TGG CGC CGG TGG TTC
                                                   Met His Gln Gly Ala Pro Ser Trp Gly Arg Arg Trp Phe-13

587-GTC GTA TGG GCG CTC TTC GGG TTG ACG CTG GGG GTC CTG GTG GTG CTG GTG GCT CCG AGT TCC CCC GGC ACG CCT
    Val Val Trp Ala Leu Leu Gly Leu Thr Leu Gly Val Leu Val Ala Ser Ala Pro Ser Ser Pro Gly Thr Pro-38
662-GGG GTC GCC GGC GAC GAC CCA GGC GGC GAA CCG GGG CCC CAC TGC GCC GCC GCC CTT GGC GCC GCC CCA ACG
    Gly Val Ala Arg Asp Asp Pro Gly Gly Glu Pro Gly His Cys Ala Ala Ala Leu Gly Ala Ala Pro Thr-63
737-GGG GAC CCG AAA CCG AAG AAG AAA CCG AAA AAA CCC CCA AAC ACG CCC GCC CCC GAC AAC GCG ACC
    Gly Asp Pro Lys Pro Lys Lys Asn Lys Pro Lys His Pro Pro Arg Pro Ala Gly Asp Asn Ala Thr-88
812-GTC GCC GCC GGC CAC GCC ACC CTG CGC GAG CAC CTG CGG GAC ATC AAG GCG GAG AAC ACC GAT GCA AAC TTT TAC
    Val Ala Ala Gly His Ala Thr Leu Arg Glu His Leu Arg Asp Ile Lys Ala Glu Asn Thr Asp Ala Asn Phe Tyr-113
887-GTG TGC CCA CCC CCG ACG GGC GCC ACG GTG GTG CAG TTC GAG CAG CCC CGC TGC CCG ACC CGG CCC GAG GGT
    Val Cys Pro Pro Pro Thr Gly Ala Thr Val Val Gln Phe Glu Gln Pro Arg Cys Pro Thr Arg Pro Glu Gly-138
962-CAG AAC TAC GAG GAG GGC ATC GCG GTC GTC TTC AAG GAG AAC ATC GCC CCG TAC AAG GCC ACC ATG TAC
    Gln Asn Tyr Glu Glu Gly Ile Ala Val Val Phe Lys Glu Asn Ile Ala Pro Tyr Lys Ala Thr Met Tyr-163
1037-TAC AAA GAC GTC ACC GTT TCG CAG GTG TGG TTC GGC CAC CGC TAC TCC CAG TTT ATG GGG ATC TTT GAG GAC CGC
     Tyr Lys Asp Val Thr Val Ser Gln Val Trp Phe Gly His Arg Tyr Ser Gln Phe Met Gly Ile Phe Glu Asp Arg-188
1112-GCC CCC GTC CCC TTC GAG GAG CTG CCC GTC ATC GAC AAG ATC AAC GCC AAG GGG GTC TGT CGG TCC ACG GCC AAG TAC GTG
     Ala Pro Val Pro Phe Glu Glu Val Ile Asp Lys Ile Asn Ala Lys Gly Val Cys Arg Ser Thr Ala Lys Tyr Val-213
1187-CGC AAC AAC CTG GAG ACC GCG TTT CAC CGG GAC ATG GAG ACC GAG ATG GAG CTG AAA CCG GCC AAC GCC
     Arg Asn Asn Leu Glu Thr Ala Phe His Arg Asp Asp His Glu Thr Asp Met Glu Leu Lys Pro Ala Asn Ala-238
```

FIG. 5A

```
1262-GCG ACC CGC ACG AGC CGG GGC TGG CAC ACC ACC GAC CTC AAG TAC TAC AAC CCC TCG CGG GTG GAG GCG TTC CAC CGG
      Ala Thr Arg Thr Ser Arg Gly Trp His Thr Thr Asp Leu Lys Tyr Asn Pro Ser Arg Val Glu Ala Phe His Arg-263
1337-TAC GGG ACG ACG GTA AAC TGC ATC GTC GAC GAG GTG GAC GCG CGC TCG GTG CTG TAC CCG TAC GAC GAG TTT GTG CTG
      Tyr Gly Thr Thr Val Asn Cys Ile Val Asp Glu Val Asp Ala Arg Ser Val Tyr Pro Tyr Asp Glu Phe Val Leu-288
1412-GCG ACT GGC GAC TTT GTG TAC ATG TCC CCG TTT TAC GGC TAC CGG GAG GGG TCG CAC GAA CAC ACC ACG TAC
      Ala Thr Gly Asp Phe Val Tyr Met Ser Pro Phe Tyr Gly Tyr Arg Glu Gly Ser His Thr Glu His Thr Thr Tyr-313
1487-GCC GCC GAC CGC TTC AAG CAG CGC GAC GTC GAC CGC TTC TAC GCG CGC GAC CTC ACC AAG GCC CGG GCC ACG GCG CCG
      Ala Ala Asp Arg Phe Lys Gln Arg Asp Val Asp Arg Phe Tyr Ala Arg Asp Leu Thr Lys Ala Arg Ala Thr Ala Pro-338
1562-ACC ACC CGG AAC CTG CTC ACG ACC CCC AAG TTC ACC GTG GCC TGG GTG GAC TGG GTG CCA AAG CGC CCG TCG GTC TGC
      Thr Thr Arg Asn Leu Leu Thr Thr Pro Lys Phe Thr Val Ala Trp Val Asp Trp Val Pro Lys Arg Pro Ser Val Cys-363
1637-ACC ATG ACC AAG TGG CAG GAA GTG CAG GAG ATG CTG CGC TCC GAG TAC GGC TCC TTC CGA TTC TCC GAC
      Thr Met Thr Lys Trp Gln Glu Val Gln Glu Met Leu Arg Ser Glu Tyr Gly Gly Ser Phe Arg Phe Ser Ser Asp-388
1712-GCC ATA TCC ACC ACC TTC ACC AAC CTG ACC GAG TAC CCG CTC TCC CGC GTG GAC CTG GGG GAC TGC ATC GGC
      Ala Ile Ser Thr Thr Phe Thr Asn Leu Thr Glu Tyr Pro Leu Ser Arg Val Asp Leu Gly Asp Cys Ile Gly-413
1787-AAG GAC GCC CGG CAC CGG ATG GAC GCC ATC TTC GCC CGC AGG TAC AAC GCG ACG CAC ATC AAG GTG GGC CAG CCG
      Lys Asp Ala Arg His Arg Met Asp Ala Ile Phe Ala Arg Arg Tyr Asn Ala Thr His Ile Lys Val Gly Gln Pro-438
1862-CAG TAC TAC CTG GCC AAT GGC TTT CTG ATC GCG TAC CAG CCC CTT CTC AGC AAC ACG CTC GCG GAG CTG TAC
      Gln Tyr Tyr Leu Ala Asn Gly Gly Phe Leu Ile Ala Tyr Gln Pro Leu Leu Ser Asn Thr Leu Ala Glu Leu Tyr-463
1937-GTG CGG GAA CAC CTC CGA GAG CAG CAG AGC CGC AAG CCC CCA AAC CCC ACG CCC CCG GCC AGC GCC AAC
      Val Arg Glu His Leu Arg Glu Gln Gln Ser Arg Lys Pro Pro Asn Pro Thr Pro Pro Pro Gly Ala Ser Ala Asn-488
2012-GCG TCC GTG GAG CGC ATC AAG ACC TCC ATC GAG TTC GCC CGG CTG CAG TTT ACC TAC AAC CAC ATA CAG
      Ala Ser Val Glu Arg Ile Lys Thr Ser Ile Glu Phe Ala Arg Leu Gln Phe Thr Tyr Asn His Ile Gln-513
2087-CGC CAT GTC AAC GAT ATG TTG GGC CGC GTT GCC ATC GCG TGG TGC CTA CAG AAT CAC GAG CTG ACC CTG TGG
      Arg His Val Asn Asp Met Leu Gly Arg Val Ala Ile Ala Trp Cys Leu Gln Asn His Glu Leu Thr Leu Trp-538
2162-AAC GAG GCG CGC AAG CTG AAC CCC ATC GCC GTC ACC GTG GGC CGG AGC GTG ATG CTC
      Asn Glu Ala Arg Lys Leu Asn Pro Asn Ala Ile Ala Ser Val Thr Val Gly Arg Ser Val Ala Arg Met Leu-563
```

FIG.5B

```
2237-GGC GAC GTG ATG GCC GTC TCC ACG TGC GTG CCG GTC GCC GCC GAC AAC GTG ATC GTC CAA AAC TCG ATG CGC ATC
      Gly Asp Val Met Ala Val Ser Thr Cys Val Pro Val Ala Ala Asp Asn Val Ile Val Gln Asn Ser Met Arg Ile-588
2312-AGC TCC CGG CCC GGG GCC TGC TAC AGC CGC CCC CTG GTC GCC TTT CGG TAC GAA GAC CAG GGC CCG TTG GTC GAG
      Ser Ser Arg Pro Gly Ala Cys Tyr Ser Arg Pro Leu Val Ala Phe Arg Tyr Glu Asp Gln Gly Pro Leu Val Glu-613
2387-GGG CAG CTG GGG GAG AAC AAC GAG CTG CGG ACG CGC GAT GCG ATC GAG CCG TGC ACC GTG GGA CAC CGG CGC
      Gly Gln Leu Gly Glu Asn Asn Glu Leu Arg Thr Arg Asp Ala Ile Glu Pro Cys Thr Val Gly His Arg Arg-638
2462-TAC TTC ACC TTC GGT GGG GGC TAC GTG TAC TTC GAG GAG TAC GCC CAC CAG CTG AGC CGC GCC GAC ATC
      Tyr Phe Thr Phe Gly Gly Gly Tyr Val Tyr Phe Glu Glu Tyr Ala Tyr Ser His Gln Leu Ser Arg Ala Asp Ile-663
2537-ACC ACC GTC ACC ACC TTC ATC GAC CTC AAC ATC CTC GAG GAT CAC GAG TTT GTC CCC CTG GAG GTG TAC
      Thr Thr Val Thr Thr Phe Ile Asp Leu Asn Ile Thr Met Leu Glu Asp His Glu Phe Val Pro Leu Glu Val Tyr-688
2612-ACC CCC CAC GAG ATC AAG GAC AGC GGC CTG GAC CTG CTC GAC GCC CGC AAC CAG CTG CAC GAC CTG
      Thr Arg His Glu Ile Lys Asp Ser Gly Leu Asp Leu Leu Asp Ala Arg Asn Gln Leu His Asp Leu-713
2687-CGC TTC GCC GAC ATC GAC CTG ATC GAC GTC ATC CAC GAC GCC AAC GCC ATC TTC GCG GGC CTG GCG TTC TTC
      Arg Phe Ala Asp Ile Asp Leu Ile Asp Val Ile His Asp Ala Asn Ala Ile Phe Ala Gly Leu Ala Phe Phe-738
2762-GAG ATG GGC GAC CTG GGG CGC GCC GTC ATG GGA CTC GTG GGC GTG GTA TCG GCG GTG
      Glu Gly Met Gly Asp Leu Gly Arg Ala Val Met Gly Val Val Gly Val Ser Ala Val-763
2837-TCG GGC GTG TCC TCC ATG TCC AAC CCC TTT GGG GCG CTG GTC CTG GCC GGC CTG GCC
      Ser Gly Val Ser Ser Met Ser Asn Pro Phe Gly Ala Leu Val Gly Leu Leu Ala Gly Leu Ala-788
2912-GCG TTC TTC GCC TTT CGT TAC GTC ATG GTC ATG CGG CTG CAG AGC CTG ATG AAG AGC CTC TAC CCT CTA ACC ACC
      Ala Phe Phe Ala Phe Arg Tyr Val Met Val Met Arg Leu Gln Ser Leu Met Lys Ser Leu Tyr Pro Leu Thr Thr-813
2987-AAG GAC CTC AAG AAC AAC GAC CTC AAC TCC GGG GAG GGC GAC TTT GAC GAG GCC AAG
      Lys Asp Leu Lys Asn Pro Thr Asn Pro Asp Ala Ser Gly Glu Gly Asp Phe Asp Glu Ala Lys-838
3062-CTA GCC GAG GCC AGG GAG ATG ATA CGG ATG GCC TAC ATG GCC CTG GTG TCG GAG CGC ACG AAG GCC AAG
      Leu Ala Glu Ala Arg Glu Met Ile Arg Met Ala Tyr Met Ala Leu Val Ser Ala Met Glu Arg Thr Lys Ala Lys-863
3137-AAG AAG GGC ACG AGC AGC CGG CTC CTC AGC GCC AAG GCC GAC GTC ATG GGC CGG AAG CGC AAC ACC TAC
      Lys Lys Gly Thr Ser Ser Arg Leu Leu Ser Ala Lys Val Thr Asp Met Val Met Arg Lys Arg Asn Thr Asn Tyr-888
```

FIG. 5C

3212-ACC CAA GTT CCC AAC AAA GAC GGT GAC GCC GAC GAG GAC GAC CTG TGACGGGGGGTTTGTTGTAAATAAAAACCACGGGTGTTAA
     Thr Gln Val Pro Asn Lys Asp Gly Asp Ala Asp Glu Asp Asp Leu END

3297-ACCGCATGGCCATCTTTTGTTTTTTGTTTGTCAGCCTTTGTCTGTGGAAGAGAAAAGGAACACATAAACTCCCCGGTGTCCGCGGC

3397-CTGTTCCTCTTCCTTCCCGTGACAAACGGACCCCCTGGTCAGTGCCGATTCCTCCCCACGCTCCTCCACGTCAAAGGCTTTGCATTGT

3497-AAAGCTACCGCCTACCCGCCCCTCCCAATAAAAAAAAGAACATACACCAATGGTCTTATTGGTATTACCTGGTTTATTTAAAAGATATACAGTA

3597-AGACATCCCATGGTACCAAAGACCGGGCGAATCAGCGGCCCCCATCATCTGAGACGAACAAATCGGCGGCCGGCCGTGTCAACGTCCACGTGTG

3697-CTGCGCTGCTGGCCTTGACAAGGCCCCGGCCTCCGCGTTGGATGCTCCGGTTGGGATCC

FIG.5-D

```
CTCGGAGAAGATGCTGCGGTCAGCGTCCACGGCGAGGTGCTGCCCCGCGACGTTCGCCGCG      60
GTCGCCAACGGCTTTGCGGCCGCGCGCCCGGCTTCTCGCCGCCCCTGACGGCGGGGCGCGGG     120
CACGGTCATCGACAACCGCTCGGCGCCGGGGCGTGTTCGACGCGCACCGGTTCATGCGAGC     180
GTCTCTCCTGCGACACCAGGTGGACCCGGCCCTGCTCCCCAGCATCACCCATCGCTTCTT      240
CGAGCTCGTCAACGGGCCCCTCTTTGATCACTCCACCCACAGCTTCGCCCAGCCCCCCAA      300
CACCGCGCTGTATTACAGCGTCGAGAACGTGGGGCTCCTGCCGCACCTGAAGGAGGAGCT      360
CGCCCCGGTTCATCATGGGGGCGGGGGGCTCGGGTGCTGATTGGGCCGTCAGCGAATTTCA     420
GAGGTTTTACTGTTTTGACGGCATTTCCGGAATAACGCCCACTCAGCGCGCCGCCTGGCG      480
ATATATTCGCGAGCTGATTATCGCCACCACACTCTTTGCCTCGGTCTACCGGTGCGGGGA      540
GCTCGAGTTGCGCCGCCCGGACTGCAGCCGCCCGACCTCCGAAGGTCGTTACCGTTACCC      600
GCCCGGCGTATATCTCACGTACGACTCCGACTGTCCGCTGGTGGCCATCGTCGAGAGCGC      660
CCCCGACGGCTGTATCGGCCCCCGGTCGGTCGTGGTCTACGACCGAGACGTTTTCTCGAT      720
CCTCTACTCGGTCCTCCAGCACCTCGCCCCCAGGCTACCTGACGGGGGGCACGACGGGC      779
                MetArgGlnGlyAlaAlaArgGlyCysArgTrpPheValValTrp      -15
CCCCGTAGTCCCGCCATGCGCCAGGGCGCCGCGCGGGGGTGCCGGTGGTTCGTCGTATGG      839
AlaLeuLeuGlyLeuThrLeuGlyValLeuValAlaSerAlaAlaProSerSerProGly       6
GCGCTCTTGGGGTTGACGCTGGGGGTCCTGGTGGCGTCGGCGGCTCCGAGTTCCCCCGGC      899
ThrProGlyValAlaAlaAlaThrGlnAlaAlaAsnGlyGlyProAlaThrProAlaPro      26
ACGCCTGGGGTCGCGGCCGCGACCCAGGCGGCGAACGGGGGACCTGCCACTCCGGCGCCG      959
ProAlaProGlyProAlaProThrGlyAspThrLysProLysLysAsnLysLysProLys      46
CCCGCCCCTGGCCCCTCCCCAACGGGGGACACGAAACCGAAGAACAACAAAAAACCGAAA     1019
AsnProProProProArgProAlaGlyAspAsnAlaThrValAlaAlaGlyHisAlaThr      66
AACCCACCGCCGCCGCGCCCCGCCGGCGACAACGCGACCGTCGCCGCGGGCCACGCCACC     1079
LeuArgGulHisLeuArgAspIleLysAlaGluAsnThrAspAlaAsnPheTyrValCys      86
CTGCGCGAGCACCTGCGGGACATCAAGGCGGACAACACCGATGCAAACTTTTACGTGTGC     1139
ProProProThrGlyAlaThrValValGlnPheGluGlnProArgArgCysProThrArg     106
CCACCCCCCACGGGCGCCACGGTGGTGCAGTTCGACGAGCCGCGCCGCTGCCCGACCCGG     1199
ProGluGlyGlnAsnTyrThrGluGlyIleAlaValValPheLysGluAsnIleAlaPro     126
CCCGAGGGTCAGAACTACACGGAGGGCATCGCGGTGGTCTTCAAGGACAACATCGCCCCG     1259
TyrLysPheLysAlaThrMetTyrTyrLysAspValThrValSerGlnValTrpPheGly     146
TACAAGTTCAAGGCCACCATGTACTACAAAGACGTCACCGTTTCGCAGGTGTGGTTCGGC     1319
HisArgTyrSerGlnPheMetGlyIlePheGluAspArgAlaProValProPheGluGlu     166
CACCGCTACTCCCAGTTTATGGGGATCTTTGAGGACCGCGCCCCCGTCCCCTTCGAGGAG     1379
ValIleAspLysIleAsnAlaLysGlyValCysArgSerThrAlaLysTyrValArgAsn     186
GTGCTCGACAAGATCAACGCCAAGGGGGTCTGTCGGTCCACGGCCAAGTACGTGCGCAAC     1439
```

FIG. 6A

```
AsnLeuGluThrThrAlaPheHisArgAspAspHisGluThrAspMetGluLeuLysPro       206
AACCTGGAGACCACCGCGTTTCACCGGGACGACCACGAGACCGACATGGAGCTGAAACCG     1499
AlaAsnAlaAlaThrArgThrSerArgGlyTrpHisThrThrAspLeuLysTyrAsnPro      226
GCCAACGCCGCGACCCGCACGAGCCGGGGCTGGCACACCACCGACCTCAAGTACAACCCC     1559
SerArgValGluAlaPheHisArgTyrGlyThrThrValAsnCysIleValGluGluVal      246
TCGCGGGTGGAGGCGTTCCACCGGTACGGGACGACGGTAAACTGCATCGTCGAGGAGGTG     1619
AspAlaArgSerValTyrProTyrAspGluPheValLeuAlaThrGlyAspPheValTyr      266
GACGCCGCTCGGTGTACCCGTACGACGAGTTTGTGCTGGCGACTGGCGACTTTGTGTAC     1679
MetSerProOheTyrGlyTyrArgGluAlySerHisThrGluHisThrSerTyrAlaAla      286
ATGTCCCCGTTTTACGGCTACCGGGAGGGGTCGCAGACCGAACACACCAGCTACGCCGCC     1739
AspArgPheLysGlnValAspGlyPheTyrAlaArgAspLeuThrTyrLysAlaArgAla      306
GACCGCTTCAAGCAGGTTGACGGCTTCTACGCGCGCGACCTCACCTACAAGGCCCGGGCC     1799
ThrAlaProThrThrArgAsnLeuLeuThrThrProLysPheThrValAlaTrpAspTrp      326
ACGGCGCCGACCACCCGGAACCTGCTCACGACCCCCAAGTTCACCGTGGCCTGGGACTGG     1859
ValProLysArgProSerValCysThrMetThrLysTrpGlnGluValAspGluMetLeu      346
GTGCCAAAGCGCCCCGTCGGTCTGCACCATGACCAAGTGGCAGGAGGTGGACGAGATGCTG   1919
ArgSerGluTyrGlyGlySerPheArgPheSerSerAspAlaIleSerThrThrPheThr     366
CGCTCCGAGTACGGCGGCTCCTTCCGATTCTCCTCCGACGCCATATCCACCACCTTCACC     1979
ThrAsnLeuThrGluTyrProLeuSerArgValAspLeuGlyAspCysIleGlyLysAsp      386
ACCAACCTGACCGAGTACCCGCTCTCGCGCGTGGACCTGGGGGACTGCATCGGCAAGGAC     2039
AlaArgAspAlaMetAspArgIlePheAlaArgArgTyrAsnAlaThrHisIleLysVal      406
GCCCGCGACGCCATGGACCGCATCTTCGCCCGCAGGTACAACGCGACGCACATCAAGGTG     2099
GlyGlnProGlnTyrTyrLeuAlaAsnGlyGlyPheLeuIleAlaTyrGlnProLeuLeu      426
GGCCAGCCGCAGTACTACCTGGCCAATGGGGGCTTTCTGATCGCGTACCAGCCCCTTCTC     2159
SerAsnThrLeuAlaGluLeuTyrValArgGluHisLeuArgGluGlnSerArgLysPro      446
AGCAACACGCTCGCGGAGCTGTACGTGCGGGAACACCTCCGAGAGCAGAGCCGCAAGCCC     2219
ProAsnProThrProProProProGlyAlaSerAlaAsnAlaSerValGluArgIleLys      466
CCAAACCCCACGCCCCCGCCGCCCGGGGCCAGCGCCAACGCGTCCGTGGAGCGCATCAAG     2279
ThrThrSerSerIleGluPheAlaArgLeuGlnPhrThrTyrAsnHisIleGlnArgHis      486
ACCACCTCCTCCATCGAGTTCGCCCCGGCTGCAGTTTACGTACAACCACATACAGCGCCAT   2339
ValAsnAspMetLeuGlyArgValAlaIleAlaTrpCysGluLeuGlnAsnHisGluLeu      506
GTCAACGATATGTTGGGCCGCGTTGCCATCGCGTGGTGCGAGCTGCAGAATCACGAGCTG     2399
ThrLeuTrpAsnGluAlaArgLysLeuAsnProAsnAlaIleAlaSerAlaThrValGly      526
ACCCTGTGGAACGAGGCCCGCAAGCTGAACCCCAACGCCATCGCCTCGGCCACCGTGGGC     2459
ArgArgValSerAlaArgMetLeuGlyAspValMetAlaValSerThrCysValProVal      546
CGGCGGGTGAGCGCGCGGATGCTCGGCGACGTGATGGCCGTCTCCACGTGCGTGCCGGTC     2519
AlaAlaAspAsnValIleValGlnAsnSerMetArgIleSerSerArgProGlyAlaCys      566
GCCGCGGACAACGTGATCGTCCAAAACTCGATGCGCATCAGCTCGCGGCCCGGGGCCTGC     2579
TyrSerArgProLeuValSerPheArgTyrGluAspGlnGlyProLeuValGluGlyGln      586
TACAGCCGCCCCCTGGTCAGCTTTCGGTACGAAGACCAGGGCCCGTTGGTCGAGCGGCAG     2639
```

FIG. 6B

```
LeuGlyGluAsnAsnGluLeuArgLeuThrArgAspAlaIleGluProCysThrValGly      606
CTGGGGGAGAACAACGAGCTGCCGGCTGACGCGCGATGCGATCGAGCCGTGCACCGTGGGA   2699
HisArgArgTyrPheThrPheGlyGlyGlyTyrValTyrPheGluGluTyrAlaTyrSer    626
CACCCGGCGCTACTTCACCTTCGGCGGGGGCTACGTGTACTTCGAGGAGTACGCGTACTCC   2759
HisGlnLeuSerArgAlaAspIleThrThrValSerThrPheIleAspLeuAsnIleThr    646
CACCAGCTGAGCCGCGCCGACATCACCACCGTCAGCACCTTCATCGACCTCAACATCACC   2819
MetLeuGluAspHisGluPheValProLeuGluValTyrThrArgHisGluIleLysAsp    666
ATGCTGGAGGATCACGAGTTTGTCCCCCTGGAGGTGTACACCCGCCACGCGATCAAGGAC   2879
SerGlyLeuLeuAspTyrThrGluValGlnArgArgAsnGluLeuHisAspLeuArgPhe    686
AGCGGCCTGCTGGACTACACGGAGGTCCAGCGCCGCAACCAGCTGCACGACCTGCGCTTC   2939
AlaAspIleAspThrValIleHisAlaAspAlaAsnAlaAlaMetPheAlaGlyLeuGly    706
GCCGACATCGACACGGTCATCCACGCCGACGCCAACGCCGCCATGTTCGCGGGCCTGGGC   2999
AlaPhePheGluGlyMetGlyAspLeuGlyArgAlaValGlyLysValValMetGlyIle    726
GCGTTCTTCGAGGGGATGGGCGACCTGGGGCGCGCGGTCGGCAAGGTGGTGATGGGCATC   3059
ValGlyGlyValValSerAlaValSerGlyValSerSerPheMetSerAsnProPheGly    746
GTGGGCGGCGTGGTATCGGCCGTGTCGGGCGTGTCCTCCTTCATGTCCAACCCCTTTGGG   3119
AlaLeuAlaValGlyLeuLeuValLeuAlaGlyLeuAlaAlaAlaPhePheAlaPheArg    766
GCGCTGGCCGTGGGTCTGTTGGTCCTGGCCGGCCTGGCGGCGGCTTTCTTCGCCTTTCGC   3179
TyrValMetArgLeuGlnSerAsnProMetLysAlaLeuTyrProLeuThrThrLysGlu    786
TACGTCATGCGGCTGCAGAGCAACCCCATGAAGGCCCTGTACCCGCTAACCACCAAGGAG   3239
LeuLysAsnProThrAsnProAspAlaSerGlyGluGlyGluGlyGlyAspPheAsp      806
CTCAAGAACCCCACCAACCCGGACGCGTCCGGGGAGGGCGAGGAGGGCGGCGACTTTGAC   3299
GluAlaLysLeuAlaGluAlaArgGluMetIleArgTyrMetAlaLeuValSerAlaMet    826
GAGGCCAAGCTAGCCGAGGCCCGGGAGATGATACGGTACATGGCCCTGGTGTCTGCCATG   3359
GluArgThrGluHisLysAlaLysLysLysGlyThrSerAlaLeuLeuSerAlaLysVal    846
GAGCGCACGGAACACAAGGCCAAGAAGAAGGGCACGAGCGCGCTGCTCAGCGCCAAGGTC   3419
ThrAspMetValMetArgLysArgArgAsnThrAsnTyrThrGlnValProAsnLysAsp    866
ACCGACATGGTCATGCGCAAGCGCCGCAACACCAACTACACCCAAGTTCCCAACAAAGAC   3479
GlyAspAlaAspGluAspAspLeu                                         874
GGTGACGCCGACGAGGACGACCTGTGACGGGGGGTTTGTTGTAAATAAAAACCACGGGTG
TTAAACCGCATGTGCATCTTTTGGTTTGTTTGTTTGGTACGCCTTTTGTGTGTGTGGGAA   3599
GAAAGAAAAGGGAACACATAAACTCCCCCGGGTGTCCGCGGCCTGTTTCCTCTTTCCTTT
CCCGTGACAAAACGGACCCCCTTGGTCAGTGCCGATTCCCCCCCCACGCCTTCCTCCACG   3719
TCGAAGGCTTTTGCATTGTAAAGCTACCCGCCTACCCGCGCCCTCCCAATAAAAAAAGAAC
ATACACCAATGGGTCTTATTTGGTATTACCTGGTTTATTTAAAAAGATATACAGTAAGAC   3839
ATCCCATGGTACCAAAGACCGGGGCGAATCAGCCGGGCCCCCATCATCTGAGAGACGAACA
AATCGGCGGCGCGGGCCGTGTCAACGTCCACGTGTGCTGCGCTGCTGGCGTTGACAAGGG   3959
CCCCGGCCCTCCGCGTTGGATGCCTCCGGTTGGGATCC    3996
```

FIG.6C

```
  1
Ala Pro Thr Ser Ser Ser Thr Lys Lys Thr Gln Leu Gln
                        20
Leu Glu His Leu Leu Leu Asp Leu Gln Met Ile Leu Asn

Gly Ile Asn Asn Tyr Lys Asn Pro Lys Leu Thr Arg Met
40
Leu Thr Phe Lys Phe Tyr Met Pro Lys Lys Ala Thr Glu
                                60
Leu Lys His Leu Gln Cys Leu Glu Glu Glu Leu Lys Pro

Leu Glu Glu Val Leu Asn Leu Ala Gln Ser Lys Asn Phe
       80
His Leu Arg Pro Arg Asp Leu Ile Ser Asn Ile Asn Val
                                   100
Ile Val Leu Glu Leu Lys Gly Ser Glu Thr Thr Phe Met

Cys Glu Tyr Ala Asp Glu Thr Ala Thr Ile Val Glu Phe
          120
Leu Asn Arg Trp Ile Thr Phe Cys Gln Ser Ile Ile Ser
          133
Thr Leu Thr
```

FIG.7

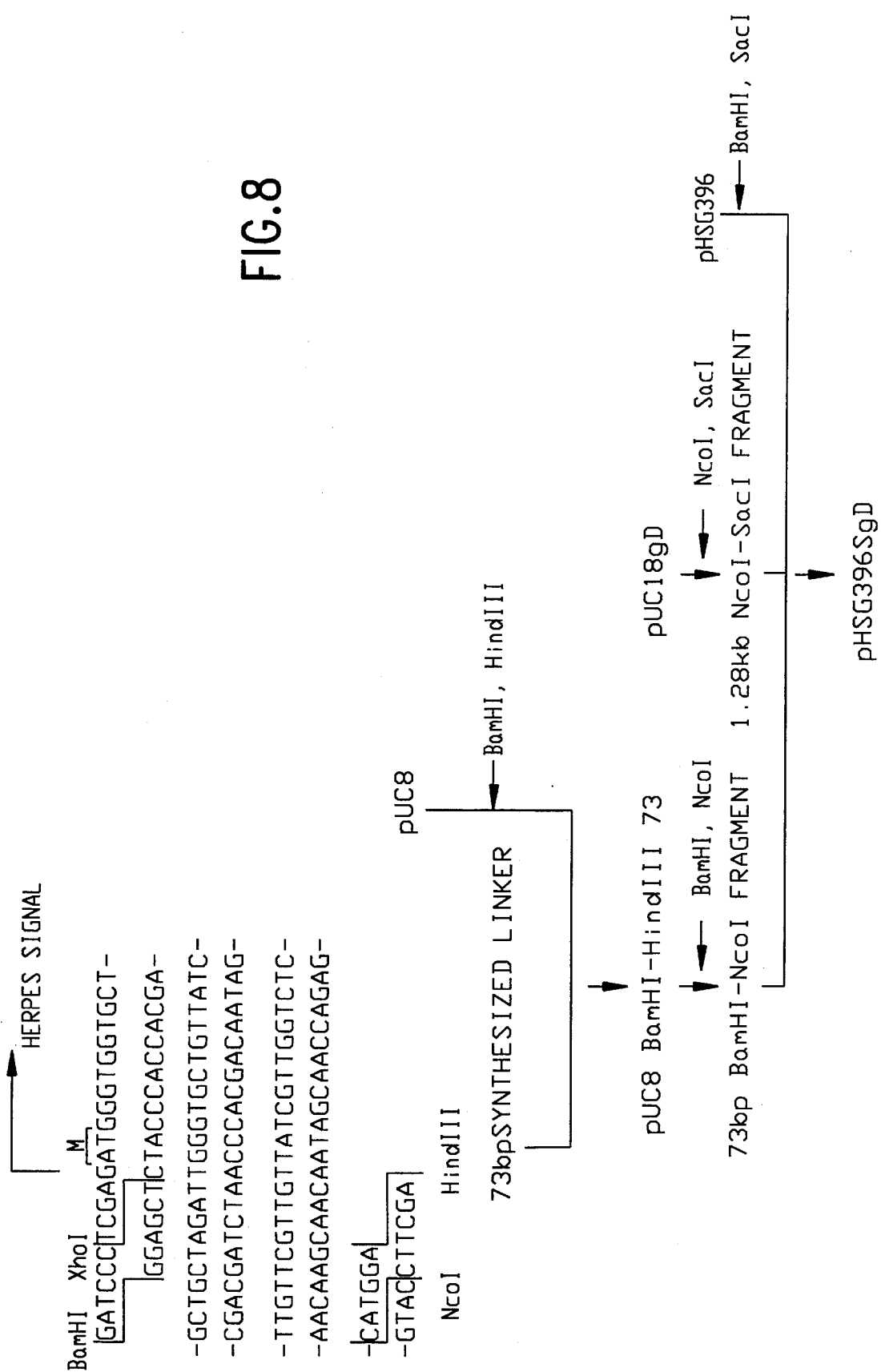

```
   1  ATG GGG GGG GCT GCC GCC AGG TTG GGG GCC GTG ATT TTG TTT GTC
  46  GTC ATA GTG GGC CTC CAT GGG GTC CGC GGC AAA TAT GCC TTG GCG
  91  GAT GCC TCT CTC AAG ATG GCC GAC CCC AAT CGC TTT CGC GGC AAA
 136  GAC CTT CCG GTC CTG GAC CCG CTG ACC GAC CCT CCG GGG GTC CGG
 181  CGC GTG TAC CAC ATC CAG GCG GGC CTA CCG GAC CCG TTC CAG CCC
 226  CCC AGC CTC CCG ATC ACG GTT TAC TAC GCC GTG TTG GAG CGC GCC
 271  TGC CGC AGC GTG CTC CTA AAC GCA CCG TCG GAG GCC CCC CAG ATT
 316  GTC CGC GGG GCC TCC GAA GAC GTC CGG AAA CAA CCC TAC AAC CTG
 361  ACC ATC GCT TGG TTT CGG ATG GGA GGC AAC TGT GCT ATC CCC ATC
 406  ACG GTC ATG GAG TAC ACC GAA TGC TCC TAC AAC AAG TCT CTG GGG
 451  GCC TGT CCC ATC CGA ACG CAG CCC CGC TGG AAC TAC TAT GAC AGC
 496  TTC AGC GCC GTC AGC GAG GAT AAC CTG GGG TTC CTG ATG CAC GCC
 541  CCC GCG TTT GAG ACC GCC GGC ACG TAC CTG CGG CTC GTG AAG ATA
 586  AAC GAC TGG ACG GAG ATT ACA CAG TTT ATC CTG GAG CAC CGA GCC
 631  AAG GGC TCC TGT AAG TAC GCC CTC CCG CTG CGC ATC CCC CCG TCA
 676  GCC TGC CTC TCC CCC CAG GCC TAC CAG CAG GGG GTG ACG GTG GAC
 721  AGC ATC GGG ATG CTG CCC CGC TTC ATC CCC GAG AAC CAG CGC ACC
 766  GTC GCC GTA TAC AGC TTG AAG ATC GCC GGG TGG CAC GGG CCC AAG
 811  GCC CCA TAC ACG AGC ACC CTG CTG CCC CCT GAG CTG TCC GAG ACC
 856  CCC AAC GCC ACG CAG CCA GAA CTC GCC CCG GAA GAC CCC GAG GAT
 901  TCG CTA GCG CCT ACT TCA AGT TCT ACA AAG AAA ACA CAG CTA CAA
 946  CTG GAG CAT TTA CTG CTG GAT TTA CAG ATG ATT TTG AAT GGA ATT
 991  AAT AAT TAC AAG AAT CCC AAA CTC ACC AGG ATG CTC ACA TTT AAG
1036  TTT TAC ATG CCC AAG AAG GCC ACA GAA CTG AAA CAT CTT CAG TGT
1081  CTA GAA GAA GAA CTC AAA CCT CTG GAG GAA GTG CTA AAT TTA GCT
1126  CAA AGC AAA AAC TTT CAC TTA AGA CCC AGG GAC TTA ATC AGC AAT
1171  ATC AAC GTA ATA GTT CTG GAA CTA AAG GGA TCT GAA ACA ACA TTC
1216  ATG TGT GAA TAT GCT GAT GAG ACA GCA ACC ATT GTA GAA TTT CTG
1261  AAC AGA TGG ATT ACC TTT TGT CAA AGC ATC ATC TCA ACA CTG ACT
1306  TGA
```

FIG.11

```
  1 Met Gly Gly Ala Ala Ala Arg Leu Gly Ala Val Ile Leu Phe Val
 16 Val Ile Val Gly Leu His Gly Val Arg Gly Lys Tyr Ala Leu Ala
 31 Asp Ala Ser Leu Lys Met Ala Asp Pro Asn Arg Phe Arg Gly Lys
 46 Asp Leu Pro Val Leu Asp Pro Leu Thr Asp Pro Pro Gly Val Arg
 61 Arg Val Tyr His Ile Gln Ala Gly Leu Pro Asp Pro Phe Gln Pro
 76 Pro Ser Leu Pro Ile Thr Val Tyr Tyr Ala Val Leu Glu Arg Ala
 91 Cys Arg Ser Val Leu Leu Asn Ala Pro Ser Glu Ala Pro Gln Ile
106 Val Arg Gly Ala Ser Glu Asp Val Arg Lys Gln Pro Tyr Asn Leu
121 Thr Ile Ala Trp Phe Arg Met Gly Gly Asn Cys Ala Ile Pro Ile
136 Thr Val Met Glu Tyr Thr Glu Cys Ser Tyr Asn Lys Ser Leu Gly
151 Ala Cys Pro Ile Arg Thr Gln Pro Arg Trp Asn Tyr Tyr Asp Ser
166 Phe Ser Ala Val Ser Glu Asp Asn Leu Gly Phe Leu Met His Ala
181 Pro Ala Phe Glu Thr Ala Gly Thr Tyr Leu Arg Leu Val Lys Ile
196 Asn Asp Trp Thr Glu Ile Thr Gln Phe Ile Leu Glu His Arg Ala
211 Lys Gly Ser Cys Lys Tyr Ala Leu Pro Leu Arg Ile Pro Pro Ser
226 Ala Cys Leu Ser Pro Gln Ala Tyr Gln Gln Gly Val Thr Val Asp
241 Ser Ile Gly Met Leu Pro Arg Phe Ile Pro Glu Asn Gln Arg Thr
256 Val Ala Val Tyr Ser Leu Lys Ile Ala Gly Trp His Gly Pro Lys
271 Ala Pro Tyr Thr Ser Thr Leu Leu Pro Pro Glu Leu Ser Glu Thr
286 Pro Asn Ala Thr Gln Pro Glu Leu Ala Pro Glu Asp Pro Glu Asp
301 Ser Leu Ala Pro Thr Ser Ser Ser Thr Lys Lys Thr Gln Leu Gln
316 Leu Glu His Leu Leu Leu Asp Leu Gln Met Ile Leu Asn Gly Ile
331 Asn Asn Tyr Lys Asn Pro Lys Leu Thr Arg Met Leu Thr Phe Lys
346 Phe Tyr Met Pro Lys Lys Ala Thr Glu Leu Lys His Leu Gln Cys
361 Leu Glu Glu Glu Leu Lys Pro Leu Glu Glu Val Leu Asn Leu Ala
376 Gln Ser Lys Asn Phe His Leu Arg Pro Arg Asp Leu Ile Ser Asn
391 Ile Asn Val Ile Val Leu Glu Leu Lys Gly Ser Glu Thr Thr Phe
406 Met Cys Glu Tyr Ala Asp Glu Thr Ala Thr Ile Val Glu Phe Leu
421 Asn Arg Trp Ile Thr Phe Cys Gln Ser Ile Ile Ser Thr Leu Thr
```

FIG.12

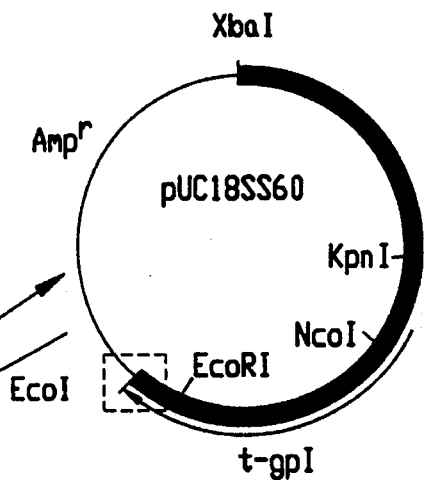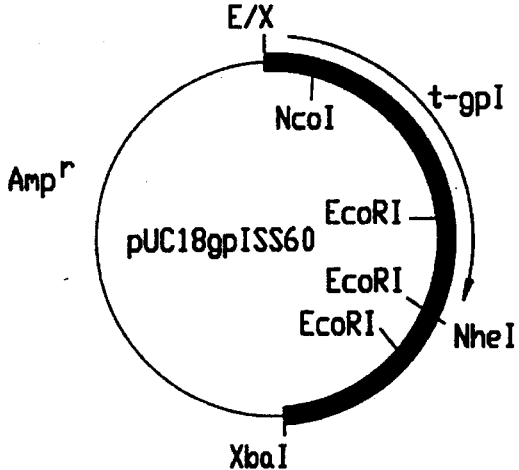
FIG. 16E pUC18gpISS60
| EcoRI (PARTIAL)
5.5 Kb FRAGMENT
| Klenow POLYMERASE
| T4 DNA LIGASE
pUC18gpISS060-E7
| XbaI
2.7 Kb FRAGMENT
| Klenow POLYMERASE ——————————————— pTB701
EcoRI
Klenow POLYMERASE

```
  1 CG AGA GCA GTC CAT GGT TTT AGA CCT CGG GCG AAT TGC GTG GTT TTA  47
  1                                         Met Gly Thr Val Asn Lys   6
 48 AGT GAC TAT ATT CCG AGG GTC GCC TGT AAT ATG GGG ACA GTT AAT AAA  95
  7 Pro Val Val Gly Val Leu Met Gly Phe Gly Ile Ile Thr Gly Thr Leu  22
 96 CCT GTG GTG GGG GTA TTG ATG GGG TTC GGA ATT ATC ACG GGA ACG TTG 143
 23 Arg Ile Thr Asn Pro Val Arg Ala Ser Val Leu Arg Tyr Asp Asp Phe  38
144 CGT ATA ACG AAT CCG GTC AGA GCA TCC GTC TTG CGA TAC GAT GAT TTT 191
 39 His Ile Asp Glu Asp Lys Leu Asp Thr Asn Ser Val Tyr Glu Pro Tyr  54
192 CAC ATC GAT GAA GAC AAA CTG GAT ACA AAC TCC GTA TAT GAG CCT TAC 239
 55 Tyr His Ser Asp His Ala Glu Ser Ser Trp Val Asn Arg Gly Glu Ser  70
240 TAC CAT TCA GAT CAT GCG GAG TCT TCA TGG GTA AAC CGG GGA GAG TCT 287
 71 Ser Arg Lys Ala Tyr Asp His Asn Ser Pro Tyr Ile Trp Pro Arg Asn  86
288 TCG CGA AAA GCG TAC GAT CAT AAC TCA CCT TAT ATA TGG CCA CGT AAT 335
 87 Asp Tyr Asp Gly Phe Leu Glu Asn Ala His Glu His His Gly Val Tyr 102
336 GAT TAT GAT GGA TTT TTA GAG AAC GCA CAC GAA CAC CAT GGG GTG TAT 383
103 Asn Gln Gly Arg Gly Ile Asp Ser Gly Glu Arg Leu Met Gln Pro Thr 118
384 AAT CAG GGC CGT GGT ATC GAT AGC GGG GAA CGG TTA ATG CAA CCC ACA 431
119 Gln Met Ser Ala Gln Glu Asp Leu Gly Asp Asp Thr Gly Ile His Val 134
432 CAA ATG TCT GCA CAG GAG GAT CTT GGG GAC GAT ACG GGC ATC CAC GTT 479
135 Ile Pro Thr Leu Asn Gly Asp Asp Arg His Lys Ile Val Asn Val Asp 150
480 ATC CCT ACG TTA AAC GGC GAT GAC AGA CAT AAA ATT GTA AAT GTG GAC 527
151 Gln Arg Gln Tyr Gly Asp Val Phe Lys Gly Asp Leu Asn Pro Lys Pro 166
528 CAA CGT CAA TAC GGT GAC GTG TTT AAA GGA GAT CTT AAT CCA AAA CCC 575
167 Gln Gly Gln Arg Leu Ile Glu Val Ser Val Glu Glu Asn His Pro Phe 182
576 CAA GGC CAA AGA CTC ATT GAG GTG TCA GTG GAA GAA AAT CAC CCG TTT 623
183 Thr Leu Arg Ala Pro Ile Gln Arg Ile Tyr Gly Val Arg Tyr Thr Glu 198
624 ACT TTA CGC GCA CCG ATT CAG CGG ATT TAT GGA GTC CGG TAC ACC GAG 671
199 Thr Trp Ser Phe Leu Pro Ser Leu Thr Cys Thr Gly Asp Ala Ala Pro 214
```

FIG.17A

```
672  ACT TGG AGC TTT TTG CCG TCA TTA ACC TGT ACG GGA GAC GCA GCG CCC  719
215  Ala Ile Gln His Ile Cys Leu Lys His Thr Thr Cys Phe Gln Asp Val  230
720  GCC ATC CAG CAT ATA TGT TTA AAA CAT ACA ACA TGC TTT CAA GAC GTG  767
231  Val Val Asp Val Asp Cys Ala Glu Asn Thr Lys Glu Asp Gln Leu Ala  246
768  GTG GTG GAT GTG GAT TGC GCG GAA AAT ACT AAA GAG GAT CAG TTG GCC  815
247  Glu Ile Ser Tyr Arg Phe Gln Gly Lys Lys Glu Ala Asp Gln Pro Trp  262
816  GAA ATC AGT TAC CGT TTT CAA GGT AAG AAG GAA GCG GAC CAA CCG TGG  863
263  Ile Val Val Asn Thr Ser Thr Leu Phe Asp Glu Leu Glu Leu Asp Pro  278
864  ATT GTT GTA AAC ACG AGC ACA CTG TTT GAT GAA CTC GAA TTA GAC CCC  911
279  Pro Glu Ile Glu Pro Gly Val Leu Lys Val Leu Arg Thr Glu Lys Gln  294
912  CCC GAG ATT GAA CCG GGT GTC TTG AAA GTA CTT CGG ACA GAA AAA CAA  959
295  Tyr Leu Gly Val Tyr Ile Trp Asn Met Arg Gly Ser Asp Gly Thr Ser  310
960  TAC TTG GGT GTG TAC ATT TGG AAC ATG CGC GGC TCC GAT GGT ACG TCT  1007
311  Thr Tyr Ala Thr Phe Leu Val Thr Trp Lys Gly Asp Glu Lys Thr Arg  326
1008 ACC TAC GCC ACG TTT TTG GTC ACC TGG AAA GGG GAT GAA AAA ACA AGA  1055
327  Asn Pro Thr Pro Ala Val Thr Pro Gln Pro Arg Gly Ala Glu Phe His  342
1056 AAC CCT ACG CCC GCA GTA ACT CCT CAA CCA AGA GGG GCT GAG TTT CAT  1103
343  Met Trp Asn Tyr His Ser His Val Phe Ser Val Gly Asp Thr Phe Ser  358
1104 ATG TGG AAT TAC CAC TCG CAT GTA TTT TCA GTT GGT GAT ACG TTT AGC  1151
359  Leu Ala Met His Leu Gln Tyr Lys Ile His Glu Ala Pro Phe Asp Leu  374
1152 TTG GCA ATG CAT CTT CAG TAT AAG ATA CAT GAA GCG CCA TTT GAT TTG  1199
375  Leu Leu Glu Trp Leu Tyr Val Pro Ile Asp Pro Thr Cys Gln Pro Met  390
1200 CTG TTA GAG TGG TTG TAT GTC CCC ATC GAT CCT ACA TGT CAA CCA ATG  1247
391  Arg Leu Tyr Ser Thr Cys Leu Tyr His Pro Asn Ala Pro Gln Cys Leu  406
1248 CGG TTA TAT TCT ACG TGT TTG TAT CAT CCC AAC GCA CCC CAA TGC CTC  1295
407  Ser His Met Asn Ser Gly Cys Thr Phe Thr Ser Pro His Leu Ala Gln  422
1296 TCT CAT ATG AAT TCC GGT TGT ACA TTT ACC TCG CCA CAT TTA GCC CAG  1343
423  Arg Val Ala Ser Thr Val Tyr Gln Asn Cys Glu His Ala Asp Asn Tyr  438
1344 CGT GTT GCA AGC ACA GTG TAT CAA AAT TGT GAA CAT GCA GAT AAC TAC  1391
```

FIG. 17B

```
 439 Thr Ala Tyr Cys Leu Gly Ile Ser His Met Glu Pro Ser Phe Gly Leu  454
1392 ACC GCA TAT TGT CTG GGA ATA TCT CAT ATG GAG CCT AGC TTT GGT CTA 1439
 455 Ile Leu His Asp Gly Gly Thr Thr Leu Lys Phe Val Asp Thr Pro Glu  470
1440 ATC TTA CAC GAC GGG GGC ACC ACG TTA AAG TTT GTA GAT ACA CCC GAG 1487
 471 Ser Leu Ser Gly Leu Tyr Val Phe Val Val Tyr Phe Asn Gly His Val  486
1488 AGT TTG TCG GGA TTA TAC GTT TTT GTG GTG TAT TTT AAC GGG CAT GTT 1535
 487 Glu Ala Val Ala Tyr Thr Val Val Ser Thr Val Asp His Phe Val Asn  502
1536 GAA GCC GTA GCA TAC ACT GTT GTA TCC ACA GTA GAT CAT TTT GTA AAC 1583
 503 Ala Ile Glu Glu Arg Gly Phe Pro Pro Thr Ala Gly Gln Pro Pro Ala  518
1584 GCA ATT GAA GAG CGT GGA TTT CCG CCA ACG GCC GGT CAG CCA CCG GCG 1631
 519 Thr Thr Lys Pro Lys Glu Ile Thr Pro Val Asn Pro Gly Thr Ser Pro  534
1632 ACT ACT AAA CCC AAG GAA ATT ACC CCC GTA AAC CCC GGA ACG TCA CCA 1679
 535 Leu Leu Arg Tyr Ala Ala Trp Thr Gly Gly Leu Ala Ala Val Val Leu  550
1680 CTT CTA CGA TAT GCC GCA TGG ACC GGA GGG CTT GCA GCA GTA GTA CTT 1727
 551 Leu Cys Leu Val Ile Phe Leu Ile Cys Thr Ala Lys Arg Met Arg Val  566
1728 TTA TGT CTC GTA ATA TTT TTA ATC TGT ACG GCT AAA CGA ATG AGG GTT 1775
 567 Lys Ala Tyr Arg Val Asp Lys Ser Pro Tyr Asn Gln Ser Met Tyr Tyr  582
1776 AAA GCC TAT AGG GTA GAC AAG TCC CCG TAT AAC CAA AGC ATG TAT TAC 1823
 583 Ala Gly Leu Pro Val Asp Asp Phe Glu Asp Ser Glu Ser Thr Asp Thr  598
1824 GCT GGC CTT CCA GTG GAC GAT TTC GAG GAC TCG GAA TCT ACG GAT ACG 1871
 599 Glu Glu Glu Phe Gly Asn Ala Ile Gly Gly Ser His Gly Gly Ser Ser  614
1872 GAA GAA GAG TTT GGT AAC GCG ATT GGA GGG AGT CAC GGG GGT TCG AGT 1919
 615 Tyr Thr Val Tyr Ile Asp Lys Thr Arg ***                           624
1920 TAC ACG GTG TAT ATA GAT AAG ACC CGG TGA TCA CCG AAC CGG GGC AAC 1967
1968 GTC GAG CGT GTA AAT TTA AAT AAA AAA CAG TAC GCT TTT ATC CGG TGT 2015
2016 ATG TTT TAA ATT TAT TTT TTT TTT TCT ATA TAA AGG GAT GGG GTG TCA 2063
2064 GGA TCT CTC GTA GGT TCT TGG GAC TCC AAG GGA CCC GCA GCC CAG GTA 2111
2112 CGC GTC AAA AAG CCT GTG ACA A                                    2133
```

FIG. 17C

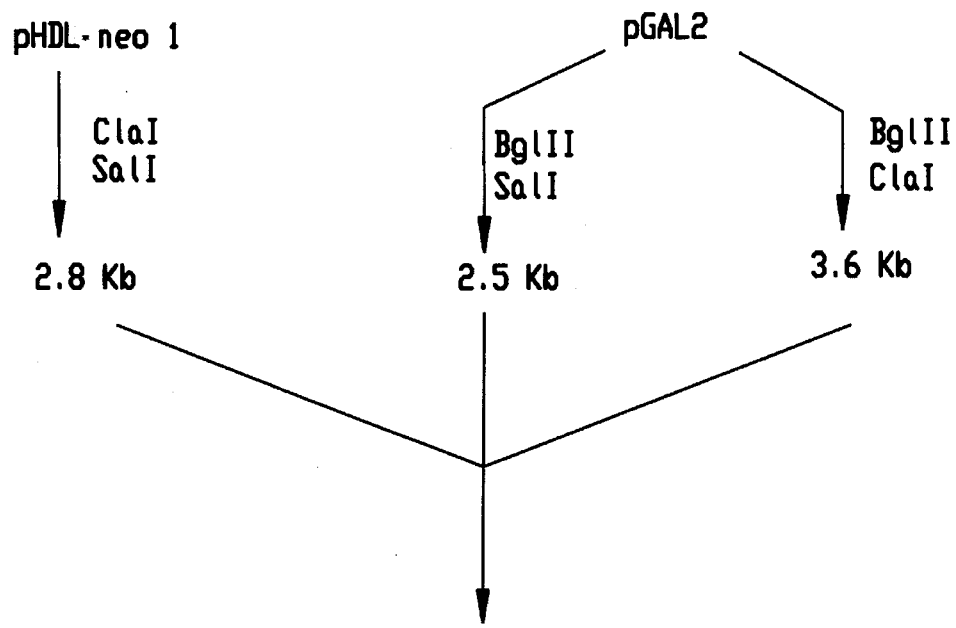
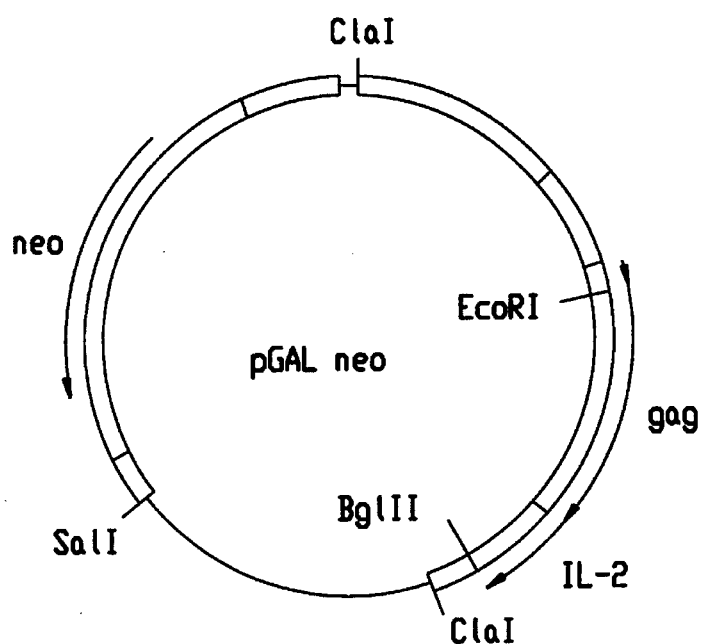
FIG.22

INTERLEUKIN-2/VIRAL ANTIGEN PROTEIN CHIMERS

This is a continuation of application Ser. No. 08/086,429 filed on Jun. 30, 1993, now abandoned, which is a continuation of Ser. No. 07/548,509, filed Jul. 2, 1990, now abandoned.

BACKGROUND OF THE INVENTION

The present invention relates to techniques for producing fused proteins useful as immunogens of therapeutic and preventive vaccines by expressing genes for fused proteins of antigens used for vaccines with lymphokines in eucaryotes or procaryotes, using recombinant DNA techniques. Further, the present invention relates to techniques for producing hybrid proteins useful as immunogens of therapeutic and preventive vaccines by chemically combining antigens used for vaccines with lymphokines.

A substance for stimulating immune responses to an antigen is called an adjuvant, which is often added to vaccines as an auxiliary substance. As the adjuvants most generally used, there are known aluminium hydroxide, aluminium phosphate and Freund's adjuvants. At present, aluminium hydroxide and aluminium phosphate are used for human, and Freund's adjuvants can not be used for human because of their strong side effects. As alternative substances to aluminium hydroxide and aluminium phosphate, there have been studied muramyldipeptide (MDP) derivatives, various lymphokines, lipid A derivatives, cholera toxins and the like.

Most of antigens produced by gene engineering technique generally have weak immunogenicity. It has therefore been desired to develop a strong adjuvant having reduced side effects in lieu of aluminium hydroxide and aluminium phosphate, or to prepare an antigen having improved immunogenicity, for the purpose of enhancing the immunogenicity of these antigens.

SUMMARY OF THE INVENTION

With the object of preparing an antigen having stronger immunogenicity, the present inventors have conducted investigations. As a result, the present inventors have discovered that fused proteins obtained by combining antigen proteins with lymphokines by genetic engineering techniques and hybrid proteins obtained by chemically combining them can attain this object.

In accordance with the present invention, there are provided (1) a fused protein obtained by combining an antigen used for a vaccine with a lymphokine by genetic engineering techniques, (2) a recombinant DNA containing a nucleotide sequence coding for the fused protein described in (1), (3) a transformant bearing the recombinant DNA described in (2), (4) a method for producing the fused protein which comprises cultivating the transformant described in (3), producing and accumulating the fused protein described in (1) in a culture, and collecting the fused protein, and (5) a hybrid protein obtained by chemically combining an antigen used for a vaccine with a lymphokine.

BRIEF DESCRIPTION OF THE DRAWINGS

FIG. 1 is a representation showing an example of an amino acid sequence of a surface protein gD gene of HSV-1 strain Miyama;

FIG. 2 is a representation showing an example of a nucleotide sequence corresponding to the amino acid sequence shown in FIG. 1;

FIGS. 3-A and 3-B are a representation showing an example of an amino acid sequence of a surface protein gB gene of the HSV-1 strain Miyama;

FIGS. 4-A to 4C are a representation showing an example of a nucleotide sequence corresponding to the amino acid sequence shown in FIGS. 3-A and 3-B;

FIGS. 5A to 5D show an example of a nucleotide sequence of a surface protein gB of HSV-1 strain KOS, and an amino acid sequence deduced therefrom;

FIGS. 6A to 6C show an example of a nucleotide sequence of a surface protein of HSV-1 strain F, and an amino acid sequence deduced therefrom;

FIG. 7 is a representation showing an amino acid sequence of an interleukin 2 active substance;

FIG. 8 is a schematic representation showing the construction of plasmid pHSG396SgD;

FIG. 11 is a representation showing a nucleotide sequence of the fused protein gene obtained in the present invention;

FIG. 12 is a representation showing an amino acid sequence deduced from the nucleotide sequence shown in FIG. 1;

FIGS. 16A to 16G are schematic representations showing the construction of plasmids used in Reference Example 2;

FIGS. 17A to 17C are a representation showing a nucleotide sequence and an amino acid sequence deduced from the nucleotide sequence of gpI gene inserted into the plasmid pUC18 in Reference Example 2;

FIG. 22 is a schematic representation showing the construction of an expression plasmid for animal cells of the fused protein gene according to the present invention.

DESCRIPTION OF THE PREFERRED EMBODIMENTS

Figure 9:
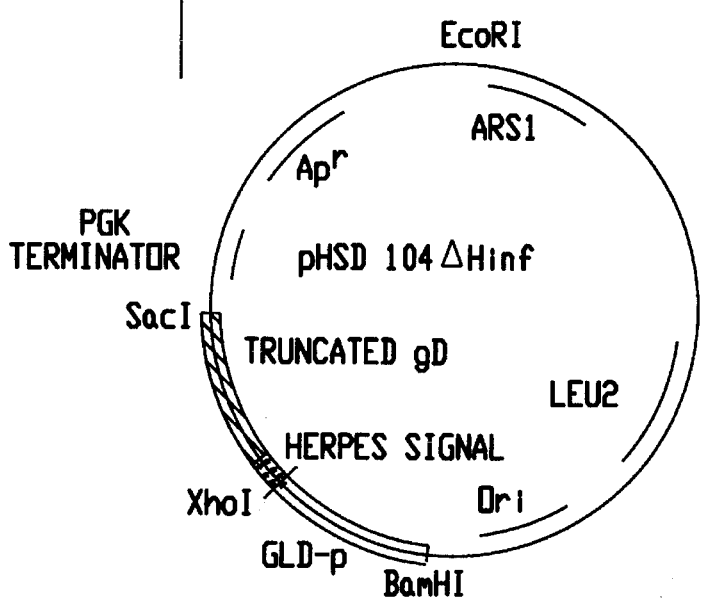
FIG. 9 is a schematic representation showing the construction of a truncated gD gene of HSV-1.

Preferred lymphokines for use in the present invention include interleukin (hereinafter referred to as IL)-1, IL-2, IL-3, IL-4, IL-5, IL-6, IL-7, granular colony stimulating factor (G-CSF), granular macrophage colony stimulating factor (GM-CSF), macrophage colony stimulating factor (M-CSF) and interferon-γ.

The antigens (proteins or polypeptides) used for vaccines in accordance with the present invention include antigens of viruses whose hosts are animals, such as antigens of herpesviruses including herpes simplex virus (HSV), varicella-zoster virus (VZV) and cytomegalovirus (CMV); antigens of retroviruses including human immunodeficiency virus (HIV) and adult human T cell leukemia virus (HTLV-I); antigens of hepadonaviruses including hepatitis B virus (HBV); antigens of togaviruses including non-A, non-B hepatitis viruses (HCV and HEV) and Japanese encephalitis virus; antigens of picornaviruses including hepatitis A virus (HAV); antigens of orthomyxoviruses including influenza virus; antigens of parvoviruses; antigens of papovaviruses; antigens of adennoviruses; antigens of poxviruses; antigens of reoviruses; antigens of paramyxoviruses; antigens of rhabdoviruses; antigens of arenaviruses; and antigens of coronaviruses; antigens of pathogenic protozoa such as a malarial antigen; and antigens of pathogenic bacteria such as a Bordetella pertussis antigen.

Examples of such antigens include surface antigen gD or gB of herpes simplex virus (HSV) type 1 or type 2, surface antigen gpI or gpIII of varicella-zoster virus (VZV), gag antigen or env antigen of human immunodeficiency virus (HIV), gag antigen or env antigen of adult human T cell leukemia virus (HTLV-I), C antigen, M antigen or E antigen of hepatitis C virus (HCV), and core antigen, surface antigen L protein, surface antigen M protein or surface antigen S protein of hepatitis B virus (HBV).

In some embodiments of the present invention, the antigen used for vaccine may be fused with the lymphokine through a linker. In other embodiments, a hybrid protein comprising an antigen used as a vaccine and a lymphokine is formed by chemical methods.

Linkers for use in the present invention comprise one amino acid residue or a peptide residue comprising 2 to about 30 amino acid residues (preferably one amino acid residue or a peptide residue comprising 2 to about 10 amino acid residues) selected from G, A, V, L, I, S, T, C, M, E, D, K, R, H, F, Y, W, P, N and Q.

As an example, a fused protein of an HSV surface protein which is an HSV antigen with IL-2 will hereinafter be described.

As the HSV surface protein, glycoproteins gD and gB lacking transmembrance domains are advantageously used.

The present invention particularly provides (1) fused protein (I) of glycoprotein gD lacking the transmembrane domain with IL-2, or fused protein (II) of glycoprotein gB lacking transmembrane domain with IL-2; (2) recombinant DNAs (III) and (IV) containing nucleotide sequences coding for fused proteins (I) and (II), respectively; (3) transformants bearing recombinant DNAs (III) or (IV), respectively; and (4) a method for producing fused protein (I) or (II) which comprises cultivating the transformant bearing recombinant DNA (III) or (IV), producing and accumulating fused protein (I) or (II) in a culture, and collecting fused protein (I) or (II).

As surface protein genes of HSV, there can be used, for example, gD and gB genes of various HSV-1 strains such as HSV-1 strain Miyama. Examples of the gD genes include a gene having the amino acid sequence shown in FIG. 1 (surface protein gD of HSV-1 strain Miyama, Japanese Patent Application No. 63-180114/1988). The essential portion of this amino acid sequence is from Lys of No. 26 to Ala of No. 302. Examples of the DNAs containing the nucleotide sequence coding for this gD gene include a DNA having the nucleotide sequence shown in FIG. 2. The portion from No. 186 to No. 1016 thereof corresponds to the essential portion. Examples of the gB include a polypeptide having the amino acid sequence shown in FIGS. 3-A and 3-B (surface protein gB of HSV-1 strain Miyama, Japanese Patent Application No. 1-158238/1989 filed on Jun. 22, 1989 and Japanese Patent Application No. 1-308941/1989 filed on Nov. 30, 1989). The essential portion thereof is from Ala of No. 1 to Asp of No. 293. Examples of the DNAs containing the nucleotide sequence coding for this gB include a DNA having the nucleotide sequence shown in FIGS. 4-A to 4-C. The portion from No. 341 to No. 1219 thereof corresponds to the essential portion. The gB genes further include, for example, genes having the nucleotide sequences and the amino acid sequences deduced therefrom shown in FIGS. 5-A to 5-D [surface protein gB of HSV-1 strain KOS, D. J. Bzik et al., Virol. 133, 301 (1984)] and FIGS. 6-A to 6-C [surface protein gB of HSV-1 strain F, P. E. Pellet et al., J. Virol. 53, 243 (1985)]. The IL-2 genes are combined with these genes, preferably with the truncated gD or gB gene lacking the coding regions of the transmembrane domains, whereby the fused protein genes can be constructed.

Amino acids residues in a protein may be modified by oxidation, reduction, or other dervitization without loss of activity. Furthermore, modifications of the primary structure of the protein by deletion, addition or alteration of the amino acids can be made without destroying the activity of the protein. Such modifications are included in the definition of "essential portion" as used herein so long as the bioactivity of the protein is not destroyed. It is expected that such modifications may qualitatively or quantitatively affect the bioactivity of the protein in the vaccines of the present invention.

IL-2 is one particularly preferred lymphokine for use in the vaccines of the present invention. Any IL-2 gene can be used as long as it codes for an IL-2 active substance. The IL-2 active substance may be any IL-2 as long as it has IL-2 activity, namely the activity of enabling the passage maintenance of T cells. Examples of such substances include natural IL-2 produced in animal bodies or animal cells, recombinant IL-2 produced by recombinant technology and their related substances. In particular, human IL-2 is preferable, and more particularly, recombinant human IL-2 is preferable. When the Il-2 described above and the related substances thereof are proteins, they may have sugar chains or not.

Specifically, there may be used, for example, polypeptide (A) produced by genetic engineering technique and having the amino acid sequence shown in FIG. 7 (refer to Japanese Patent Unexamined Publication No. 61-78799/1986), and a fragment having a portion of the amino acid sequence necessary for its biological or immunological activity. Examples of the fragments include a fragment lacking one amino acid residue at the amino terminus (refer to European Patent Publication No. 91539), a fragment lacking 4 amino acid residues at the amino terminal portion (refer to Japanese Patent Unexamined Publication No. 60-126088/1985) and a fragment lacking several amino acid residues at the carboxyl terminal portion. Further, a portion of the above polypeptide (A) may be deleted or substituted by a different amino acid(s). For example, the cystine residue at the 125-position may be replaced with a serine residue (refer to Japanese Patent Unexamined Publication No. 59-93093/1984).

The above recombinant IL-2 produced by genetic engineering technique may be a polypeptide in which an Met residue is further added to the amino terminus of polypeptide (A) (refer to Japanese Patent Unexamined Publication No. 61- 78799/1986), or a mixture of polypeptide (A) and the polypeptide in which an Met residue is further added to the amino terminus of polypeptide (A) (refer to Japanese Patent Unexamined Publication No. 60-115528/1985).

The recombinant DNA (expression plasmid) containing the nucleotide sequence coding for the fused protein (I) or (II) of the present invention can be prepared, for example, by the following processes.

(a) A desired truncated gene is cut out from a plasmid in which the gD or gB gene of HSV-1 strain Miyama has been cloned.

(b) A appropriate linker is added thereto as needed, followed by construction of a fused gene in which an IL-2 gene is linked to the 3'-terminal portion of the DNA.

(c) The resulting fused protein gene is ligated downstream from a promoter in an expression vector.

In the present invention, any vector (for example, plasmid) may be used as long as it can be replicated in an eucaryotic cell as a host. When the host is yeast, examples of such vectors include pSH19 [S. Harashima et al., Mol. Cell. Biol.* 771 (1984)] and pSH19-1 (European Patent Publication No. 0235430), and a vehicle for expression of foreign genes is obtained by inserting a promoter therein. When the host is an animal cell, the vehicle for expression of foreign genes is obtained, for example, by inserting an SV40-derived promoter, a retrovirus promoter or the like in pBR322.

As the promoter used in the present invention, any promoter is usable as long as the promoter is suitable for expression in the host used for the gene expression. When the host is yeast, it is preferred that a GLD (GAPDH) promoter, a PHO5 promoter, a PGK promoter, an ADH promoter, a PH081 promoter and the like are used. When the host is an animal cell, an SV40-derived promoter, a retrovirus promoter and the like are preferably used.

The promoters can be prepared enzymatically from the corresponding genes. They can also be chemically synthesized.

By using the vector containing the recombinant DNA thus constructed, the eucaryotic cell is transformed.

The host includes, for example, yeast and animal cells.

Examples of the yeast include *Saccharomyces cerevisiae* AH22R$^-$, NA87-11A and DKD-5D and *Schizosaccharomyces pombe* ATCC38399(h$^-$ leul-32) and TH168(h$^{90}$ ade6-M210 ural leul) [M.Kishida et al., *Current Genetics,* 10, 443(1986)].

Examples of the animal cells include adherent cells such as monkey COS-7 cell, monkey Vero cell Chinese hamster ovary (CHO) cell, mouse L cell and human FL cell, and non-adherent cells such as mouse myeloma cell (such as SP2/0), mouse YAC-1 cell, mouse MethA cell, mouse P388 cell and mouse EL-4 cell.

The transformation of the yeast is carried out according to, for example, the method described in *Proc. Natl. Acad. Sci. U.S.A.,* 75, 1929 (1978). The transformation of the animal cell is carried out according to, for example, the method described in *Virology,* 52, 456 (1973).

The transformants (recombinants) thus obtained are cultivated by per se known methods.

When the transformants in which the host is yeast are cultivated, there is used, for example, Burkholder minimum medium [K. L. Bostian et al., *Proc. Natl. Acad. Sci. U.S.A.,* 77, 4505 (1980)] as a medium. The pH of the medium is preferably adjusted to about 5 to 8. The cultivation is usually carried out at about 20° to 35° C. for about 24 to 72 hours, with aeration or agitation if necessary.

When the transformants in which the host is an animal cell are cultivated, there can be used as the medium, for example, about 5 to 20% fetal calf serum-containing, MEM medium [Science, 122, 501 (1952)], DMEM medium [*Virology,* 8, 396 (1959)], RPMI1640 medium [*Journal of the American Medical Association,* 199, 519 (1967)] and 199 medium [*Proceeding of the Society for the Biological Medicine,* 73, 1 (1950)]. The pH is preferably about 6 to 8. The cultivation is usually carried out at about 30° to 40° C. for about 15 to 60 hours, with aeration or agitation if necessary.

In the present invention, the fused proteins having both the HSV surface antigenicity and the IL-2 activity can be separated and purified by appropriate combinations of per se known separating and purifying methods. These known separating and purifying methods include methods utilizing a solubility such as salt precipitation and solvent precipitation, methods mainly utilizing a difference in molecular weight such as dialysis, ultrafitration, gel filtration and SDS-polyacrylamide gel electrophoresis, methods utilizing a difference in electric charge such as ion-exchange column chromatography, methods utilizing specific affinity such as affinity chromatography, methods utilizing a difference in hydrophobicity such as reverse-phase high performance liquid chromatography and methods utilizing a difference in isoelectric point such as isoelectric point electrophoresis.

The fused protein of an antigen other than the HSV surface protein and IL-2 can be prepared using a gene (DNA) coding for that antigen in lieu of the HSV surface protein gene, according to the methods described above.

The fused protein of the antigen used for vaccine and a lymphokine other than IL-2 can be prepared using a gene coding for the antigen and a gene coding for the lymphokine, according to the methods described above.

When the virus is a partially or completely single-stranded virus, a double-stranded DNA which is obtained by conversion with DNA polymerase can be used. When the virus is an RNA virus, there can be used a double-stranded DNA which is obtained by synthesizing a single-stranded DNA by using a reverse transcriptase and then converting the single-stranded DNA with DNA polymerase.

The host used for expression of the recombinant DNA may be a procaryotic cell such as *Escherichia coli* or Bacillus. However, in order to improve the immunogenicity of the antigen-lymphokine fused proteins obtained, a eucaryotic cell is advantageously used as described above.

The protein simultaneously containing the antigen used for vaccine and the lymphokine can be obtained by combining 2 kinds of proteins by chemical methods as described below, in addition to the above genetic engineering technique. Namely, for the purpose of chemically combining the antigen used for vaccine with the lymphokine, there can be utilized substituent groups existing in these proteins, such as amino, carboxyl, hydroxyl and sulfhydryl groups. For example, the following methods are used.

(1) A reactive amino group of one protein is condensed with a reactive carboxyl group of the other protein by dehydration in a water-soluble solvent, using a water-soluble carbodiimide reagent such as 1-ethyl-3-(3-dimethylaminopropyl)-carbodiimide or 1-cyclohexyl-3-(2-morpholinoethyl)- carbodiimide-p-toluene sulfonate.

(2) A reactive amino group of one protein is reacted with a reactive ester of N-hydroxysuccimide such as p-maleimidomethylcyclohexane-1-carboxyl-N-hydroxysuccimide ester or N-(ε-maleimidocaproyloxy)succimide ester to maleimidate the protein, and then the resulting product is combined with a sulfhydryl group of (i) a protein obtained by reducing the other protein with dithiothreitol (DTT) or (ii) a protein obtained by introducing a sulfhydryl group in the other protein with N-succimidyl-3-(2-pyridylthio)-propionate (SPDP), to combine them through a thioether bond.

(3) Both reactive amino groups of two kinds of proteins are combined with each other by using a dialdehyde reagent such as succindialdehyde or glutaraldehyde.

(4) Sulfhydryl groups are introduced in two kinds of proteins by reduction with DTT or by SPDP, followed by reoxidation to produce a heterodimer.

Also, a desired heterodimeric protein can be efficiently produced by various combinations of these methods so that the activitoes of two kinds of proteins are not reduced.

After the completion of the combining reactions described above, the resulting hybrid proteins can be purified and separated by gel filtration chromatography using Sephadex G100 or G200, Sepharose 6B or 4B, Ultrogel AcA44 or 34, or Sephacryl S200. Further, the proteins can also be separated by a combination with affinity chromatography using an antibody column.

The antigen-lymphokine fused proteins or the antigen-lymphokine hybrid proteins obtained according to the present invention have stronger immunogenicity than the antigens not fused or combined with the lymphokines. This results from the fact that the antigen and the lymphokine simultaneously stimulate lymphocytes to promote efficiently the differentiation and proliferation of the lymphocytes, because of the presence of the antigen and the lymphokine in the same molecule. As a result, the production of antibodies to the antigens is significantly enhanced. In addition, the antigen-lymphokine proteins can also induce cell-mediated immunity. Accordingly, these proteins are particularly useful as therapeutic vaccines for virus infectious diseases observed in patients whose immunological function is lowered (for example, cancer patients and AIDS patients), and as therapeutic vaccines for prevention of recurrence diseases due to viruses inducing persistent infection (for example, herpesviruses, retroviruses and hepatitis viruses). Of course, the antigen-lymphokine proteins can also be advantageously used as preventive vaccines for prevention of infection with viruses, pathogenic protozoa and pathogenic bacteria.

The antigen-lymphokine proteins obtained according to the present invention can be (intramuscularly, subcutaneously or intracutaneously) administered in accordance with administration methods of various vaccines used for prevention of infection with viruses, pathogenic protozoa and pathogenic bacteria. In addition, these proteins can also be intravenously administered. Further, the antigen-lymphokine proteins can be used as themselves alone, as mixtures of them with conventional pharmaceutically acceptable carriers, and as liposomal preparations.

When bases, amino acids and so on are indicated by the abbreviations in this specification and the drawings, the abbreviations adopted by IUPAC-IUB Commission on Biochemical Nomenclature or commonly used in the art are employed. For example, the following abbreviations are used. When the optical isomer is capable of existing with respect to the amino acids, the L-form is represented unless otherwise specified.

DNA : Deoxyribonucleic acid
cDNA: Complementary deoxyribonucleic acid
RNA : Ribonucleic acid
mRNA: Messenger RNA
A: Adenine
T: Thymine
G: Guanine
C: Cytosine
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediaminetetraacetic acid
SDS: Sodium dodecyl sulfate
DTT: Dithiothreitol
Gly: Glycine (G)
Ala: Alanine (A)
Val: Valine (V)
Leu: Leucine (L)
Ile: Isoleucine (I)
Ser: Serine (S)
Thr: Threonine (T)
Cys: Cysteine (C)
½ Cys: Half cysteine
Met: Methionine (M)
Glu: Glutamic acid (E)
Asp: Aspartic acid (D)
Lys: Lysine (K)
Arg: Arginine (R)
His: Histidine (H)
Phe: Phenylalanine (F)
Tyr: Tyrosine (Y)
Trp: Tryptophan (W)
Pro: Proline (P)
Asn: Asparagine (N)
Gln: Glutamine (Q)
$Ap^r$: Ampicillin-resistant gene
$Tc^r$: Tetracycline-resistant gene
ARS 1: Autonomous replication sequence 1

With respect to the proteins of the present invention, a portion of the amino acid sequence may be modified, namely there may be addition, elimination or substitution by a different amino acid(s) as long as the immunogenicity is not lost.

The present invention will hereinafter be described in detail with the following Reference Examples and Examples. It is understood of course that these Reference Examples and Examples are merely illustrative and are not intended to limit the scope of the invention.

Transformant CHO-HDL-1-5 obtained in Example 3 described below and bearing plasmid pHDLdhfrl was deposited with the Fermentation Research Institute, Agency of Industrial Science and Technology, Ministry of International Trade and Industry, Japan (FRI) under the accession number FERM BP-2506 on Jul. 7, 1989. This microorganism was also deposited with the Institute for Fermentation, Osaka, Japan (IFO) under the accession number IFO 50192 on Jun. 26, 1989.

Transformant *Escherichia coli* DH1/pHSD BJ-1 bearing plasmid pHSD BJ-1 described in Reference Example mentioned below was deposited with the FRI under the accession number FERM BP-1784 on Mar. 9, 1988. This microorganism was also deposited with the IFO under the accession number IFO 14730 on Feb. 23, 1988.

Transformant *Saccharomyces cerevisiae* NA74-3A(ρ⁻)/pGFE213 bearing plasmid pGFE213 described in Example 1 mentioned below was deposited with the FRI under the accession number FERM BP-2095 on Oct. 11, 1988. This microorganism was also deposited with the IFO under the accession number IFO 10460 on Sep. 19, 1988.

Animal cell SP-neo-HSD-39 described in Example 6 mentioned below was deposited with the FRI under the accession number FERM BP-2809 on Mar. 16, 1990. This microorganism was also deposited with the IFO under the accession number IFO 50231 on Mar. 1, 1990.

Animal cell SP-neo-HDL-245 described in Example 8 mentioned below was deposited with the FRI under the accession number FERM BP-2810 on Mar. 16, 1990. This microorganism was also deposited with the IFO under the accession number IFO 50232 on Mar. 1, 1990.

Transformant *Escherichia coli* K12 DH1/pTB652 bearing plasmid pTB652 described in Example 5 mentioned below was deposited with the FRI under the accession number FERM BP-1373 on Sep. 5, 1986. This microorganism was also deposited with the IFO under the accession number IFO 14539 on Aug. 29, 1986.

Transformant *Escherichia coli* JM109/pVGL4 bearing plasmid pVGL4 described in Example 15 mentioned below was deposited with the FRI under the accession number FERM BP-2977 on Jun. 20, 1990. This microorganism was also deposited with the IFO under the accession number IFO 15049 on Jun. 13, 1990.

REFERENCE EXAMPLE 1

Preparation of Plasmid pHSG396.SqD

A DNA coding for the 20 amino acid residues from the N-terminus of gD, namely the 73-bp DNA fragment shown in FIG. 8 was chemically synthesized, and inserted into vector pUC8 digested with BamHI and HindIII.

The resulting pUC8 BamHI-HindIII73 was digested with BamHI and NcoI to obtain a 73-bp fragment. On the other hand, a NcoI-SacI DNA fragment of about 1.28 kb was obtained from cloning plasmid pUC18gD having an HindIII-NruI fragment [plasmid pHSD BJ-1 (IFO 14730, FERM BP-1784 origin] of about 1.4 kb containing the gD-coding region of HSV. The above 73-bp fragment and the above NcoI-SacI DNA fragment were reacted with a BamHI-SacI digest of plasmid vector pHSG396 (Takara Shuzo) to prepare subcloning plasmid pHSG396SgD.

REFERENCE EXAMPLE 2

(1) Preparation of Virus DNA of Varicella-zoster Virus, Kuzuhara Strain

Flow 2000 cells (of human fetal lung origin) which were infected with varicella-zoster virus, Kuzuhara strain (VZV, KY strain) were inoculated at 10:1 to a monolayer (1575 cm²) of Flow 2000 cells, followed by incubation in GIT medium (Nihon Pharmaceutical) at 37° C. When at least 50% of the cells showed cytopathic effect, the cells were treated with trypsin-EDTA, and the infected cells were recovered, followed by centrifugation at low speed (1,500 rpm, 10 minutes) to remove a supernatant. To pellets of the resulting infected cells was added 0.3 ml of PBS (0.8% NaCl, 0.02% KCl, 0.115% $Na_2HPO_4$, 0.02% $KH_2PO_4$, pH 7.2) to obtain 0.66 ml of a suspension.

To the suspension was added 0.66 ml of low melting point agarose [1% low melting point agarose (FMC), 10 mM Tris HCl (pH 8.0), 1 mM EDTA), and the mixture was poured into a template (57 mm×2 mm×9 mm) to obtain an agarose block containing the infected cells. The agarose block was incubated in 15 ml of lysis buffer [1% SDS, 100 mM EDTA, 20 mM NaCl, 10 mM Tris-HCl (pH 8.0), 1 mg/ml Proteinase K] at 37° C. overnight. The agarose block was transferred into a buffer which was prepared by removing SDS and Proteinase K from the above lysis buffer, and incubated overnight again. Then, the culture was allowed to stand in TE buffer (50 mM Tris-HCl, 500 mM EDTA, pH 8.0) at 4° C. until it was subjected to electrophoresis.

The above agarose block containing virus DNA was embedded in a 1% agarose gel [1% GTG agarose (FMC), 89 mM Tris-borate, 89 mM boric acid, 2 mM EDTA (pH 8.0)], and electrophoresis was carried out by using a pulsed field gel electgrophoresis apparatus (LKB) at 240 V at a pulse of 60 sec for 18 hours.

After electrophoresis, the gel was stained in 0.5 μg/ml ethidium bromide solution, and the virus DNA which appeared near 120 kb was cut out together with the agarose gel. The agarose gel was immersed in 30 ml of TE buffer (10 mM Tris-HCl, 1 mM EDTA, pH 8.0), and allowed to stand at 4° C. for 2 hours. Then, the TE buffer was exchanged for a fresh one. After standing for 2 hours, the buffer was exchanged for a fresh one once more, followed by standing overnight. The agarose gel was washed with TE buffer once, and then immersed in 30 ml of a restriction enzyme reaction solution [10 mM Tris-HCl (pH 7.5), 7 mM $MgCl_2$, 100 mM NaCl, 7 mM 2-ME(mercaptoethanol), 0.01%BSA (bovine serum albumin)], followed by standing at 4° C. for 2 hours. After this reaction solution was exchanged for a fresh one (10 ml), 1,200 units of restriction enzyme HindIII (Takara Shuzo) was added thereto, followed by standing at 37° C. for 5 hours.

After the reaction, the HindIII-digested virus DNA was electrically eluted from the agarose gel in a dialysis tube. About 2 ml of the resulting eluate was concentrated to 200 μl by a Centricon (Amicon), and ethanol was added thereto to precipitate the DNA. The precipitate was dissolved in 20 μl of restriction enzyme buffer (the same as described above in composition), and 10 units of XbaI and 10 units of HindIII (Takara Skhuzo) were added thereto, followed by reaction at 37° C. for 2 hours. The resulting reaction solution was subjected to electrophoresis in a 0.7% GTG agarose gel (FMC) as it is. As a result, there were detected fragments having a size similar to that reported by Davison et al. [*J. Gen. Virol.* 67, 1759 (1986)].

(2) Preparation of Plasmid Containing DNA Fragment of VZV, KY Strain

Of the XbaI-HindIII-digested fragments of the DNA of the VZV, KY strain, which were obtained in (1), fractions of about 8 to 10 kb were cut out of the agarose gel and electrically eluted, followed by phenol treatment and ethanol precipitation. About 50 ng of the DNA fragments were mixed with about 30 ng of pUC18 cleaved with XbaI and HindIII, and the mixture was incubated in 25 μl of a reaction solution [66 mM Tris-HCl, pH 7.6, 6.6 mM $MgCl_2$, 10 mM dithiothreitol, 1 mM ATP, 20 units of T4 DNA ligase (Takara Shuzo)] at 16° C. overnight. Then, using the resulting solution, *Escherichia coli* JM109 was transformed. Plasmids contained in a white colony which appeared on an agar plate containing 100 μg/ml ampicillin, 0.2% X-gal and 10 mM IPTG were isolated by the alkali extraction method (T. Maniatis et al., *Molecular Cloning*, Cold Spring Harbor Laboratory, U.S.A., 1982), and the size of the XbaI-HindIII-digested fragments of cloned VZV DNA was examined by electrophoresis using a 0.7% agarose gel. A clone (pVHX7) into which a fragment of about 8.5 kb was inserted was selected, and the restriction map of the fragment was prepared. As a result, the map was similar to that reported by Davison et al., and it was anticipated that the fragment would contain a glycoprotein gpI gene (FIG. 16-1).

A 5.2 kb fragment obtained from the XbaI-SmaI digests of the above fragment was subcloned into the XbaI/SmaI site of pUC18 to prepare pCU18gpI (FIG. 16-1).

With respect to insert of pUC18gpI, the nucleotide sequence of the region of about 2.1 kb from the SmaI site was determined by the dideoxynucleotide synthetic chain termination method. The results showed that a VZVgpI protein was coded in the above region (FIGS. 17A to 17C).

An amino acid sequence deduced from the above nucleotide sequence is shown in FIGS. 17A to 17C. The nucleotide sequence of the above region was very similar to that reported by Davison et al. However, there were observed mutations in four bases [T of No. 196 (this invention)→C (Davison); C of No. 276→T; T of No. 1969→C; and T of No. 2040→lacking] (mutation in one amino acid: the 40-position is Thr in the report of Davison, but Ile in this invention).

(3) Construction (I) of Plasmid for Expression of VZVgpI Gene: Construction of Truncated gpI Transient Expression Plasmid (i) pUC18gpI (FIG. 16-1) was digested with AvaI and NcoI to isolate a 0.35-kb fragment from −53 to +293 of a translation initiating codon of gpI. pUC19Nco which was obtained by inserting an NcoI linker (Pharmacia) into the SmaI site of vector pUC19 was cleaved with NcoI and BamHI. The resulting vector was ligated to the above 0.35-kb NcoI-AvaI fragment with T4 DNA ligase once, followed by reaction with BamHI, AvaI and T4 DNA ligase in order. Finally, ring closure was conducted with T4 DNA ligase to prepare pUC19gpINco (FIG. 16-2).

pUC19gpINco was reacted with XbaI, Klenow fragment *E. coli* DNA polymerase I (Klenow polymerase) and KpnI in order to open the ring. Thus, a 0.35-kb fragment was obtained. On the other hand, pUC18Nhe which was prepared by inserting an Nhe linker into pUC18 was reacted with EcoRI, Klenow DNA polymerase and KpnI in order to obtain a ring-opened vector. The resulting vector was ligated to the above 0.35-kb fragment with T4 DNA ligase to prepare pUC18NhegpINco (FIG. 16-2).

(ii) pUC18gpI was digested with SmaI and NcoI to obtain a 1.8-kb fragment, and pUC18NhegpINco was reacted with NheI, Klenow DNA polymerase and NcoI in order to obtain a 3.1-kb vector. The above 1.8-kb fragment was ligated to the above 3.1-kb vector with T4 DNA ligase to obtain plasmid pUC18gpISma (FIG. 16-3).

The plasmid pUC18gpISma was cleaved with EcoT22I and the termini of the cleaved fragment were changed to flush ends, followed by insertion of an NheI linker to obtain plasmid pUC18NhegpIEcT (FIG. 16-3).

(iii) The plasmid pUC18NhegpIEcT was digested with XbaI to obtain a 2.1-kb fragment, and this fragment was treated with Klenow DNA polymerase. On the other hand, pTB701 [a vector which was obtained by removing a c kinase gene from pTB652, Oho et al., *Science* 236, 1116–1120 (1987)] was cleaved with EcoRI, followed by treatment with Klenow DNA polymerase to obtain a vector. The above fragment treated with Klenow DNA polymerase was ligated to the resulting vector with T4 DNA ligase to prepare expression plasmid pTBgpIEcT (FIG. 16-4).

(iv) pUC18gpI was cleaved with SmaI and SacI, and the portion of about 0.45 kb on the 3'-terminal side of the gpI gene was digested with exonuclease III. Then, the resulting fragment was treated with mung bean nuclease and Klenow DNA polymerase to change the termini thereof to flush ends, followed by ring closure with T4 DNA ligase to prepare pUC18SS60 (FIG. 16-5).

pUC18SS60 was cleaved with KpnI and partially digested with EcoRI to obtain a 2.3-kb fragment. The termini of this fragment were changed to flush ends with T4 DNA polymerase, and an NheI linker (New England Biolabs) was ligated thereto, followed by trimming with NcoI and NheI to prepare a 1.3-kb fragment. The resulting fragment was ligated to a vector which was obtained by cleaving pUC18NhegpIEcT with NcoI and NheI to prepare pUC18gpISS60 (FIG. 16-5).

(v) pUC18gpISS60 was partially digested with EcoRI, and DNA fragments each of which was cleaved only at one portion were recovered. Then, the fragments were treated with Klenow DNA polymerase, followed by ring closure with T4 DNA ligase. From these was selected clone pUC18SS60-E7 in which the EcoRI site derived from pUC18 in pUC18SS60 disappeared (FIG. 16-6).

The termini of a 2.7-kb fragment obtained by treating pUC18SS60-E7 with XbaI were changed to flush ends with Klenow DNA polymerase. On the other hand, pTB701 was cleaved with EcoRI and then the termini of the fragment were changed to flush ends with Klenow DNA polymerase to obtain a vector. The above fragment was ligated to the resulting vector to prepare expression plasmid pTBgpIE7-17 (FIG. 16-6).

(4) Construction (II) of Plasmid for Expression of VZVgpI Gene: Construction of Truncated gpI Stable Expression Plasmid Expression plasmid pTB564 of a hamster dihydrofolate reductase (hDHFR) was digested with ClaI to obtain a 1.9-kb fragment. The termini of the resulting fragment were changed to flush ends with Klenow DNA ligase. The expression plasmid pTB564 was prepared by ligating a 0.9-kb fragment, a 2.4-kb fragment and a 0.8-kb fragment to one another with T4 DNA ligase, which were obtained by digesting pTB348, pTB399 and pTB401 [R. Sasada et al., *Cell Structure and Function* 12, 205 (1987)] with PstI and BamHI, SalI and BamHI, and SalI and PstI, respectively. On the other hand, pTBgpIE7-17 was cleaved with SalI, and then the termini of the fragment were changed to flush ends with Klenow DNA polymerase to obtain a vector. The above fragment was ligated to the resulting vector to prepare expression plasmid pTBE7dhfr4 (FIG. 16-7).

EXAMPLE 1

Construction of HSV-1 Truncated gD Gene

The plasmid vector pHSG396SgD (Reference Example) having the HSV-1 strain Miyama gD gene was digested with restriction enzymes XhoI and XbaI to obtain a DNA fragment of about 1.35 kb, followed by further digestion with restriction enzyme HinfI to obtain an XhoI-HinfI fragment of about 0.91 kb. A 12-bp DNA fragment shown in FIG. 9 containing a stop codon was chemically synthesized, and reacted with the above XhoI-HinfI fragment and an XhoI-SacI digest of plasmid vector pHSG397 (Takara Shuzo) to prepare subcloning plasmid pHSG397SgDΔHinf. The resulting plasmid was digested with restriction enzymes XhoI and SacI to obtain an XhoI-SacI DNA fragment of about 0.92 kb. The fragment thus obtained was reacted with an XhoI-SacI digest of the plasmid pGFE213 (IFO 10460, FERM BP-2095 origin) described in Japanese Patent Application No. 63-180114/1988 and Reference Example 1 of Japanese Patent Application No. 63-317546/1988 to obtain expression plasmid pHSD104ΔHinf (refer to FIG. 9).

EXAMPLE 2

Construction of Gene Expression Plasmid for Fused Protein Composed of HSV-1 Truncated gD and Il-2

The subcloning plasmid pHSG397SgDΔHinf constructed in Example 1 was digested with XhoI, and a Klenow fragment was allowed to react on the digest, followed by insertion of an EcoRI linker (pGGAATTCC) (NEB) to obtain pHSG397SgDΔHinfE. The resulting plasmid was digested with HinfI to obtain a DNA fragment of about 0.95 kb, on which a Klenow fragment is allowed to react, followed by addition of an NheI linker (pCGCTAGCG) (Pharmacia) using T4 DNA ligase (Takara Shuzo). The resulting fragment was further digested with EcoRI and NheI to obtain an EcoRI-NheI fragment of about 0.9 kb coding for truncated gD lacking 94 amino acid residues from the C-terminus.

Then, animal cell expression plasmid pTB399 [Japanese Patent Unexamined Publication No. 61-63282/1986, R. Sasada et al., *Cell Structure and Function* 12, 205 (1987)] of human interleukin 2 awas digested with EcoRI and HindIII to obtain a fragment, which was further digested with HgiAI to obtain a fragment of about 0.45 kb. T4 DNA polymerase was allowed to react on the fragment thus obtained, followed by addition of the above NheI linker. The resulting fragment was further digested with BamHI and NheI to obtain an NheI-BamHI fragment of about 0.43 kb containing the coding region of mature human interleukin 2.

The two fragments described above were reacted with a fragment of about 3.9 kb obtained by EcoRI-BglII digestion of pTB399 to obtain an expression plasmid pHDL201.

Figure 10:
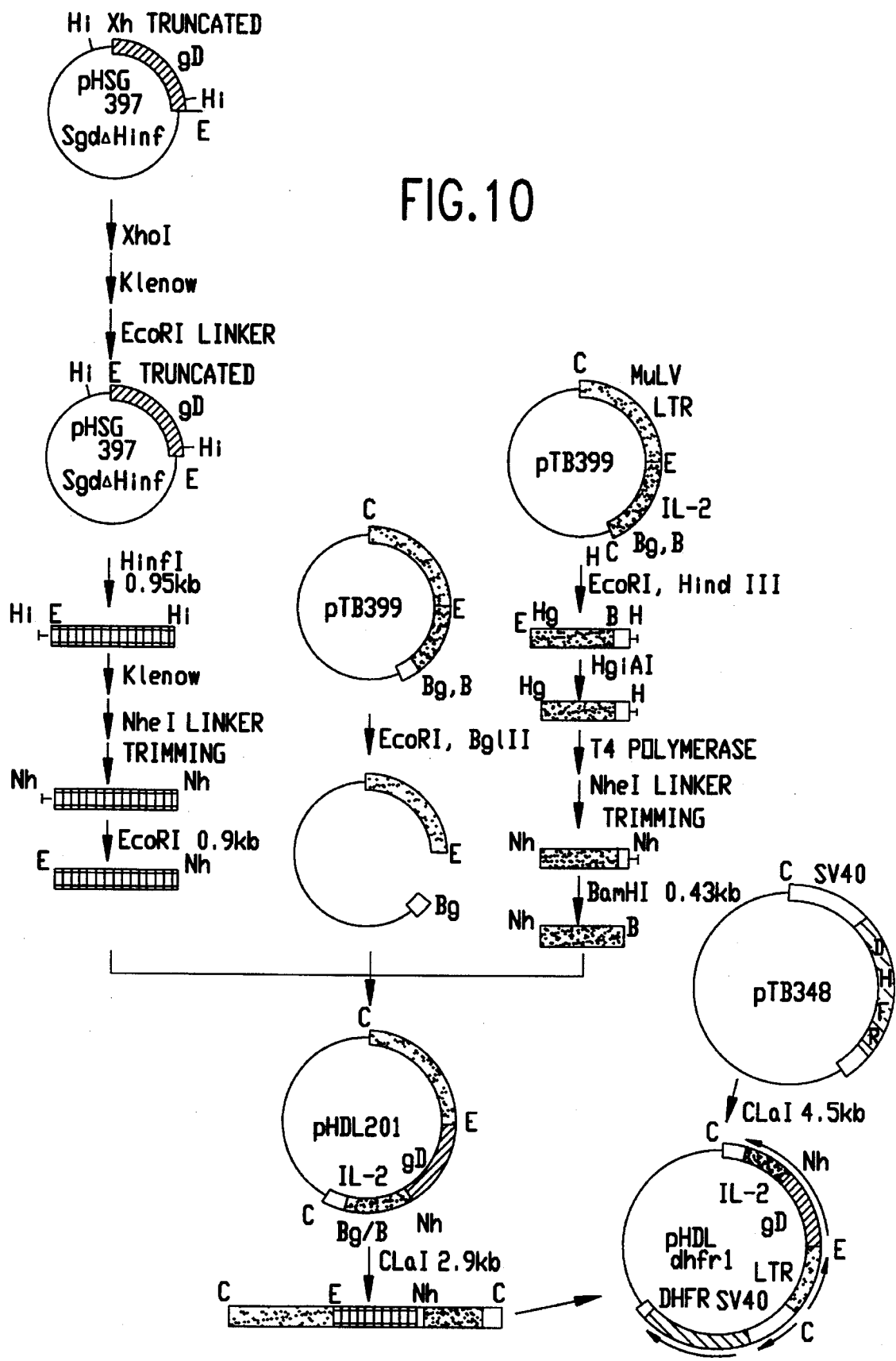
FIG. 10 is a schematic representation showing the construction of an expression plasmid of a fused protein gene according to the present invention.

Further, in order to express the above fused protein in CHO cells and to enable gene amplification, a DNA fragment containing a fused gene of IL-2 and truncated gD of about 2.9 kb which was obtained by digesting the plasmid pHDL201 with ClaI was inserted into the ClaI site of dihydrofolate reductase (DHFR) gene expression plasmid pTB348 (refer to Japanese Patent Unexamined Publication No. 61-63282/1986) to obtain plasmid pHDLdhfrl (refer to FIG. 10).

The nucleotide sequence of the resulting fused gene is shown in FIG. 11, and the amino acid sequence deduced therefrom is shown in FIG. 12.

EXAMPLE 3

Gene Expression of Fused Protein Composed of HSV-1 Truncated qD and IL-2 in Animal Cell Using the plasmid pHDLdhfrl constructed in Example 2, CHO cell DHFR⁻ strain [G. Urlaub and L. A. Chasim, *Proc. Natl. Acad. Sci. U.S.A.* 77, 4216–4220 (1980)] was transformed by the calcium phosphate method [C. M. Gorman et al, *Science* 221, 551–553 (1983)] to obtain a transformant which was converted to DHFR⁺.

The resulting transformant CHO-HDL-1-5 (IFO 50192, FERM BP-2506) was cultivated in Dulbecco MEM medium (Gibco) containing 10% fetal calf serum (Whittaker M. A. Bioproducts) so as to become confluent. Then, the medium was exchanged for a methionine-free medium, and 25 μCi/ml of S-methionine was added thereto, followed by cultivation overnight.

After a supernatant of the culture was recovered, 5 μl/ml of supernatant of rabbit anti-HSV-1 (MacIntyre) serum (Dakopatt) or 10 μl/ml of supernatant of rabbit anti-human IL-2 serum was added to the supernatant, followed by cultivation at 4° C. for 2 hours. Then, protein A-Sepharose (Pharmacia) was added thereto, and cultivation was further carried out at 4° C. for 2 hours, followed by centrifugation to recover a precipitate. The precipitate was washed with a buffer containing 0.05% NP-40, and Laemmli buffer was added thereto, followed by heating at 100° C. for 5 minutes. After cooling, a supernatant was recovered by centrifugation and subjected to SDS-polyacrylamide gel electrophoresis. After electrophoresis, the gel was dried, and subjected to autoradiography. As a result, it was revealed that products of about 45 to 60 k daltons which were reactive to both anti-HSV-1 and anti-IL-2 antibodies were produced.

EXAMPLE 4

Detection of IL-2 Activity in Expressed Product of Gene Coding for Fused Protein Composed of HSV-1 Truncated gD and IL-2

With respect to the culture of the transformant in which the expression of the fused protein composed of truncated gD and human IL-2 was observed in Example 3, the IL-2 activity was measured by the modified MTT method [H. Tada et al., *J. Immunol. Methods* 93, 157 (1986)], using IL-2-dependent cell strain NKC3.

As a result, the IL-2 activity was only detected in the culture supernatant of the cell in which the fused gene was introduced.

EXAMPLE 5

Construction of Plasmid for Expression of HSV-1 Truncated gD Gene in Myeloma Cell The plasmid pHSG397SgDΔHinfE constructed in Example 2 was digested with restriction enzyme EcoRI to obtain a fragment of about 0.9 kb coding for truncated gD. The fragment thus obtained was inserted into the EcoRI site of pTB701 [a vector obtained by removing a C-kinase gene from plasmid pTB652 described in Ono et al., *Science* 236, 1116–1120 (1987)], thereby obtaining a truncated gD expression plasmid pHSD207 having a long terminal report and the early promoter of SV40.

Figure 13:
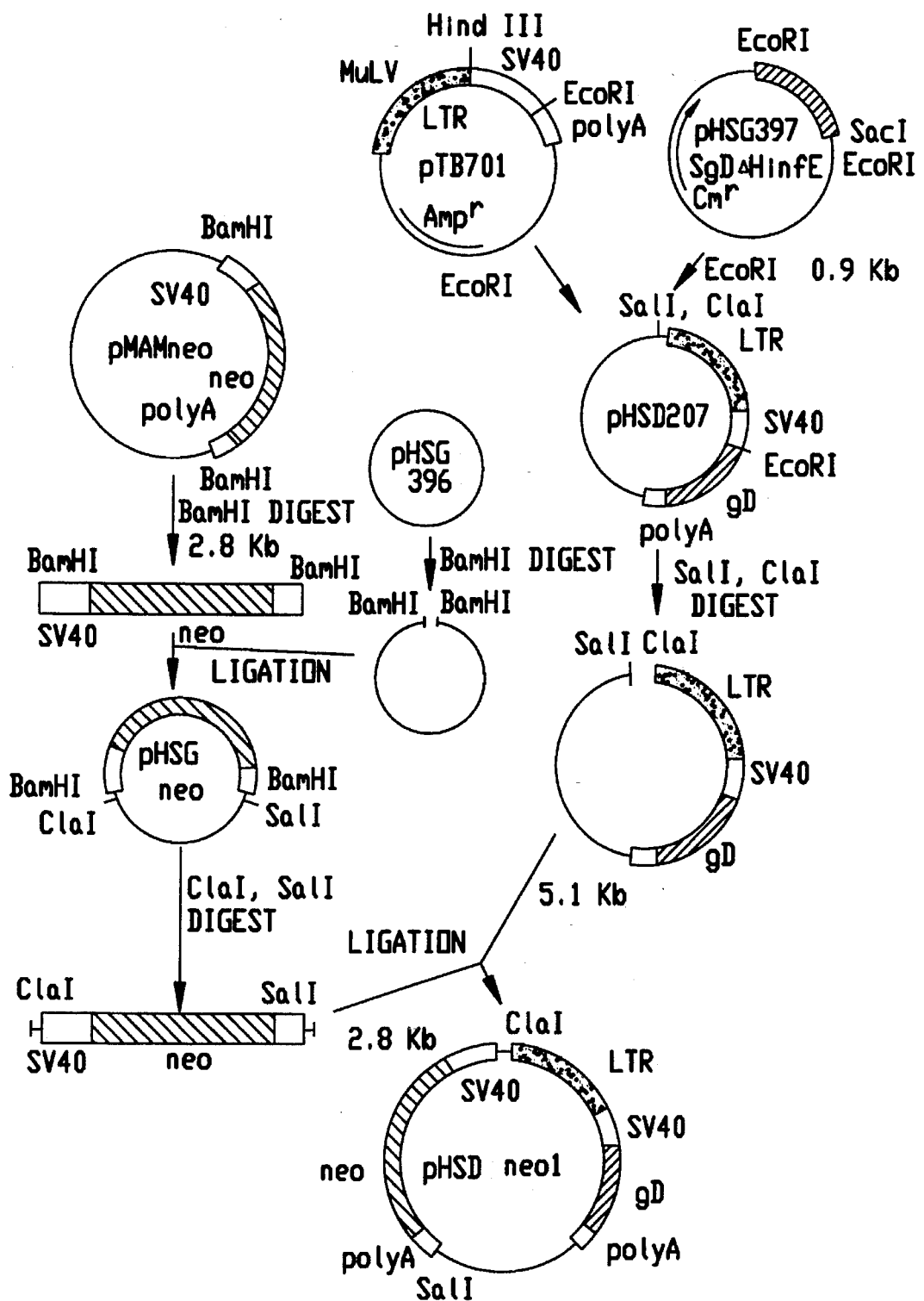
FIG. 13 is a schematic representation showing the construction of an expression plasmid for animal cells of the truncated gD gene of HSV-1.

Then, plasmid pMAMneo (Clontec) having a neomycin-resistant gene was digested with BamHI to obtain a fragment of about 2.8 kb containing the early promoter of SV40, the neomycin-resistant gene and a polyadenylation site. This fragment was subcloned to the BamHI site of pHSG396 (Takara Shuzo), followed by further digestion with restriction enzymes ClaI and SalI to obtain a ClaI-SalI fragment of about 2.8 kb containing the neomycin-resistant gene. The resulting fragment was reacted with a ClaI-SalI digest (about 5.1 kb) of the above plasmid pHSD207 to obtain an expression plasmid pHSDneoI of about 7.9 kb (refer to FIG. 13).

EXAMPLE 6

Expression of HSV-1 Truncated gD Gene in Myeloma Cell

Using the plasmid pHSDneol constructed in Example 5, mouse myeloma cell Sp2/0-Ag14 (Dainippon Pharmaceutical) was transformed by electroporation using a Gene Pulser (Bio-Rad), followed by cultivation in RPMI1640 medium (Gibco) containing 400 μg/ml of G418 (Gibco) and 10% fetal calf serum to obtain G418-resistant transformants. A culture supernatant of the transformants was screened according to an enzyme immunoassay by a sandwich method using a microplate (Nunc) coated with rabbit anti-HSV-1 serum (Dakopatt) and biotinyl anti-HSV-1 & -2 antibody (Chemicon) to obtain clones in which truncated gD was expressed.

The resulting high expression clone SP-neo-HSD-39 was cultivated in RPMI1640 medium (Gibco) containing 10% fetal calf serum (Whittaker M. A. Bioproducts), and then the medium was exchanged for a methionine-free medium, and 25 μCi/ml of $^{35}$S-methionine was added thereto, followed by cultivation overnight.

After a supernatant of the culture was recovered, 5 μl/ml of supernatant of rabbit anti-HSV-1 serum (Dakopatt) was added to the supernatant, and the mixture was incubatied at 4° C. for 2 hours, followed by centrifugation to recover a precipitate. The precipitate was washed with a buffer containing 0.05% NP-40, and Laemmli buffer was added thereto, followed by heating at 100° C. for 5 minutes. After cooling, a supernatant was recovered by centrifugation and subjected to SDS-polyacrylamide gel electrophoresis. After electrophoresis, the gel was dried, and subjected to autoradiography. As a result, it was revealed that products of about 40 to 50 k daltons which were reactive to an anti-HSV-1 antibody were produced.

EXAMPLE 7

Figure 14:
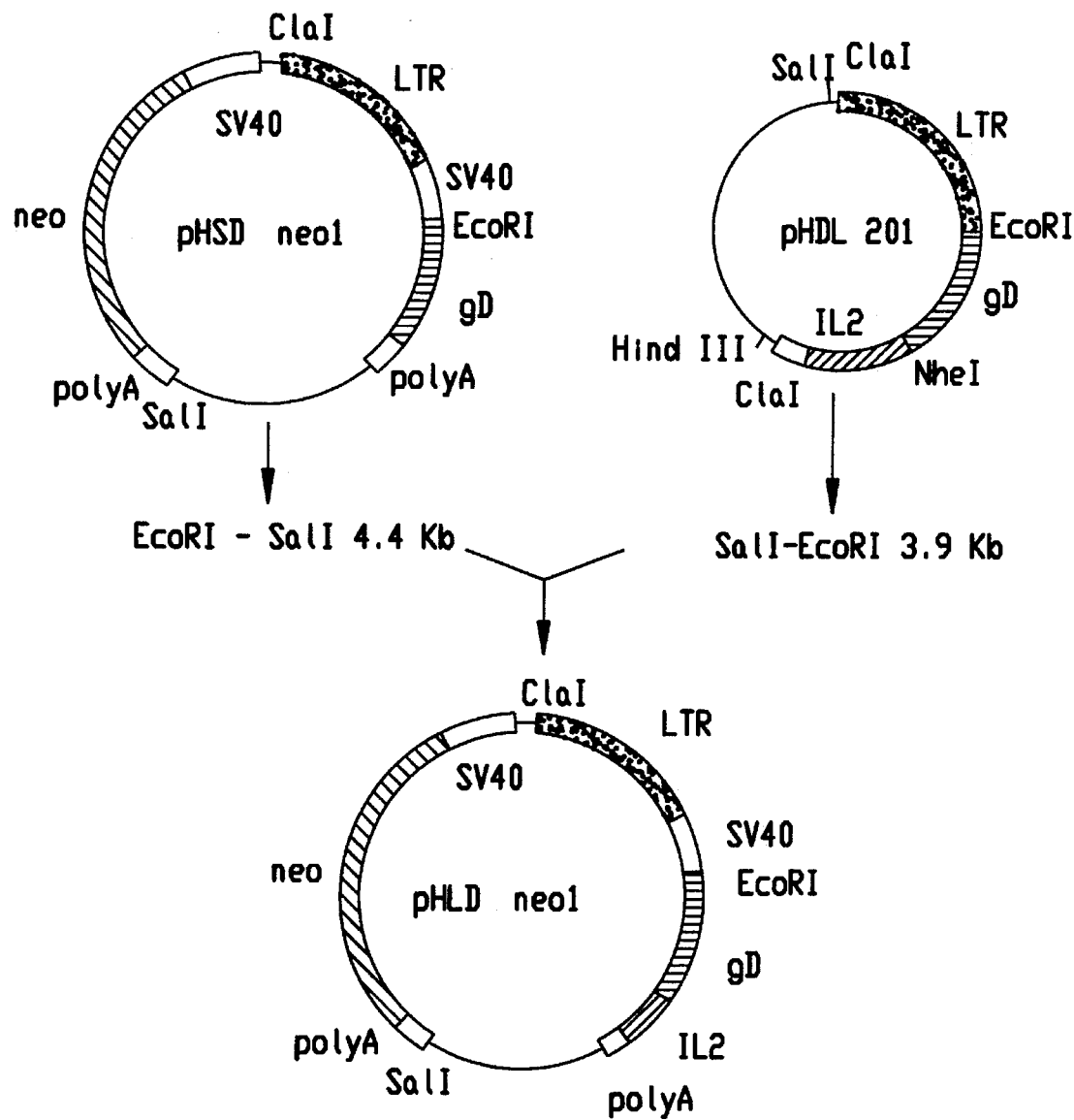
FIG. 14 is a schematic representation showing the construction of an expression plasmid for animal cells of the fused protein gene according to the present invention.

Construction of Gene Expression Plasmid Fused Protein Composed of HSV-1 Truncated qD and IL-2 in Myeloma Cell The plasmid pHDL201 constructed in Example 2 was digested with restriction enzymes SalI and EcoRI to obtain a fragment of about 3.9 kb containing a fused gene composed of truncated gD and IL-2. On the other hand, the truncated gD expression plasmid pHSDneol having the neomycin-resistant gene in Example 5 was digested with SalI and EcoRI to obtain a fragment of about 4.4 kb containing the neomycin-resistant gene. These two fragments were reacted with each other to obtain expression plasmid pHDLneol of the truncated gD-IL-2 fused gene having the neomycin-resistant gene (refer to FIG. 14).

EXAMPLE 8

Gene Expression of Fused Protein Composed of HSV-1 Truncated gD and IL-2 in Myeloma Cell Using the plasmid pHDLneol constructed in Example 7, mouse myeloma cell Sp2/0-Ag14 (Dainippon Pharmaceutical) was transformed by electroporation using a Gene Pulser (Bio-Rad), followed by cultivation in RPMI1640 medium (Gibco) containing 200 μg/ml of G418 (Gibco) and 10% fetal calf serum to obtain G418-resistant transformants. A culture supernatant of the transformants was screened according to an enzyme immunoassay by a sandwich method using a microplate (Nunc) coated with rabbit anti-HSV-1 serum (Dakopatt) and biotinyl anti-HSV-1 & -2 antibody (Chemicon) to obtain clones in which truncated gD was expressed.

Of the clones, Sp-neo-HDL-245 relatively high in expression amount was cultivated in serum-free medium ASF104 (Ajinomoto), and 1 ml of a supernatant thereof was concentrated by Ultrafree PF (Millipore). Then, Laemmli buffer was added thereto to 50 μl, followed by heating at 100° C. for 5 minutes. After cooling, SDS-polyacrylamide gel electrophoresis was conducted, and further the western blotting method was carried out using rabbit anti-HSV-1 serum (Dakopatt) and rabbit anti-human IL-2 serum (Genzyme). As a result, bands recognized by all antibodies were specifically detected.

EXAMPLE 9

Expression of HSV-1 Trucated gD Gene in Animal Cell

Expression plasmid pHSDdhfrl of HSV-1 truncated gD gene for animal cells was prepared as described in Reference Examples 1 and 2 and Example 1 of Japanese Patent Application No. 1-233728/1989, and transformant CHO-HSD-1-7 was obtained as described in Example 2 of the same application. The details thereof will hereinafter be described.

The plasmid pHSG397SgDΔHinf shown in Example 1 was digested with XhoI and SacI, and then T4 DNA polymerase was allowed to react on the digest to obtain a fragment of about 0.9 kb containing the truncated gD gene, both ends of the fragment being flush.

Then, plasmid pTB399 [Japanese Patent Unexamined Publication No. 61-63282/1986; R. Sasada et al., *Cell Structure and Function* 12, 205 (1987)] was digested with restriction enzymes EcoRI and BglII, and then T4 DNA polymerase was allowed to react on the digest to obtain a fragment of about 3.9 kb both ends of which are flush. The resulting fragment was reacted with the above fragment containing truncated gD in the presence of T4 DNA ligase to obtain expression plasmid pHSD209.

Then, in order to express the gene in CHO cells and to enable gene amplification, a fragment of about 2.4 kb which was obtained by digesting the plasmid pHSD209 with restriction enzyme ClaI was inserted into the ClaI site of plasmid pTB348 (refer to Japanese Patent Unexamined Publication No. 61-63282/1986) to obtain plasmids pHSDdhfr1 and pHSDdhfr2.

Using the plasmid pHSDdhfr1, CHO cell DHFR$^-$ strain [G. Urlaub and L. A. Chasim, *Proc. Natl. Acad. Sci. U.S.A.* 77, 4216–4220 (1980)] was transformed by the calcium phosphate method [C. M. Gorman et al, *Science* 221, 551–553 (1983)] to obtain a transformant which was converted to DHFR$^+$.

EXAMPLE 10

Purification of HSV-1 Truncated gD (t-gD)

The transformant CHO-HSD-1-7 obtained in Example 9 was cultivated in serum-free medium ASF104 (Ajinomoto) so as to give a confluent state. Then, 5 1 of the culture supernatant was dialyzed against 20 mM Tris-HCl (pH 8.0) buffer, followed by addition of ammonium sulfate to obtain a 20% saturated concentration. The resulting solution was subjected to a Butyl-Toyopearl column (100 ml in bed capacity, ⌀2.6×19 cm) equilibrated with 20% saturated ammonium sulfate/20 mM Tris-HCl (pH 8.0) buffer, and then the column was washed with the same buffer. Subsequently, t-gD was eluted by a concentration gradient (totaled 800 ml) from 20% to 0% ammonium sulfate. t-gD fractions (70 ml) eluted at saturated ammonium sulfate concentrations of about 3 to 5% were concentrated to 4 ml with an ultrafiltration membrane (DIAFLO; Amicon). The resulting solution was subjected to a Sephacryl S-300 column (198 ml in bed capacity, ⌀1.6×98.5 cm) equilibrated with PBS, and t-gD fractions were collected as a purified sample (3.5 mg/16 ml).

EXAMPLE 11

Purification of Fused Protein (t-gD-IL-2) Composed of HSV-1 Truncated gD and IL-2

The transformant CHO-HDL-1-5 obtained in Example 3 was cultivated in serum-free medium ASF104 (Ajinomoto) so as to give a confluent state. Then, 5 l of the culture supernatant was dialyzed against 20 mM Tris-HCl (pH 8.0) buffer, followed by addition of ammonium sulfate to obtain a 20% saturated concentration. The resulting solution was subjected to a Butyl-Toyopearl 650 column (100 ml in bed capacity, ⌀2.6×19 cm) equilibrated with 20% saturated ammonium sulfate/20 mM Tris-HCl (pH 8.0) buffer, and then the column was washed with the same buffer. Subsequently, t-gD-IL-2 was eluted by a concentration gradient (totaled 800 ml) from 20% to 0% ammonium sulfate. t-gD fractions (70 ml) eluted at saturated ammonium sulfate concentrations of about 0% were concentrated to 4 ml with an ultrafiltration membrane (Amicon). The resulting solution was subjected to a Sephacryl S-300 column (198 ml in bed capacity, ⌀1.6×98.5 cm) equilibrated with PBS, and t-gD-IL-2 fractions were collected as a purified sample (2.8 mg/14 ml).

EXAMPLE 12

Immunogenicity of Fused Protein (t-gD-IL-2) Composed of HSV-1 Truncated gD and IL-2

(1) Determination of Anti-HSV Antibodies

Each of truncated gD (t-gD) obtained in Example 10 and t-gD-IL-2 obtained in Example 11, alone or adsorbed on alum adjuvant (final concentration 0.5 mg/ml, pH 7.0), was abdominally subcutaneously administered in an amount of 0.2 ml/mouse to BALB/c mice (female, 6 weeks old, Charles River). After 5 weeks, blood was collected and serum samples were prepared. The anti-HSV antibodies were determined by the following method.

An inactivated HSV-coated microplate of a human anti-HSV antibody determination kit (Herpes Stat, Whittaker Bioproducts, Lot No. 002706) was blocked with PBS containing 20% FCS at room temperature for 2 hours, followed by washing 3 times with PBS containing 0.05% Tween 20 (PBS-Tween). To this plate was added 100 µl/well of the serum sample diluted with 20% FCS/40 mM Tris-HCl (pH 7.5)/5% NACl/0.05% Tween 20, followed by incubation at room temperature for 1 hour. The plate was washed 6 times with PBS-Tween, and then 100 µl of a 1,000-fold dilution of a peroxidase-labeled anti-mouse IgG antibody (HPR-conjugated rabbit X mouse IgG [H + L], Zymed Laboratories, Lot No. 80801651) was added to each well, followed by incubation at room temperature for 30 minutes. The plate was washed 6 times with PBS-Tween, and then 100 µl of a substrate solution [2 mg/ml o-phenylenediamine/0.02% $H_2O_2$/0.1M citrate buffer (pH 4.5)] was added to each well, followed by reaction for 10 minutes. After 200 µl of 2N sulfuric acid was added to each well to terminate color development, the absorbance was measured at 492 nm. (2) Comparison of Antibody Productivity of t-gD with That of t-gD-IL-2.

The titer of the anti-HSV antibody in the serum sample was calculated using mouse anti-gD monoclonal antibody M42 [Koji Inoue, *Osaka University Medical Magazine* 36 (No.4), 69 (1987)] as a standard antibody in the following manner. The antibody titer of the M42 antibody (1.9 mg/ml) was arbitrarily defined as to 1900 mU/ml, and the titer of the anti-HSV antibody was determined from the ratio of the dilution of M42 giving the 50% value (about 1) of the maximum absorbance ($\geq 2.0$) given by the 4-fold dilution of M42 to that of the serum sample. Mean values for groups each consisting of 10 mice are shown in Table 1.

TABLE 1

| Antigen | Dose (µg) | Antibody titer (mU/ml) | |
|---|---|---|---|
| | | Alum (−) | Alum (+) |
| t-gD | 0.35 | — | 76 |
| | 1.7 | <5 | 228 |
| t-gD-IL-2 | 1.0 | — | 513 |
| | 5.0 | 285 | 1,653 |
| Control | — | — | <5 |

As apparent from Table 1, when the antigen was administered alone [Alum (−)], t-gD could hardly induce the antibody. However, t-gD-IL-2 significantly exhibited the antibody productivity. These results revealed that IL-2 combined with t-gD achieved a strong adjuvant activity. When the Alum adjuvant was used [Alum (+)], it was observed that t-gD produced the antibody (228 mU/ml on administration of 1.7 µg). However, the high antibody titer was obtained by t-gD-IL-2 (513 mU/ml on administration of 1.0 µg), and the effect of IL-2 addition was observed.

EXAMPLE 13

Immunogenicity of Fused Protein (t-gD-IL-2) Composed of HSV-1 Truncated gD and IL-2

(1) Determination of Anti-HSV Antibodies

Each of truncated gD (t-gD) obtained in Example 10 and t-gD-IL-2 obtained in Example 11, alone, mixed with equimolar human recombinant IL-2 (rIL-2; 1.21 mg/ml, Takeda Chemical Industries, Lot No. H-609-035) or adsorbed on alum adjuvant (final concentration 0.5 mg/ml, pH 7.0), was abdominally subcutaneously administered in an amount of 0.2 ml/mouse to BALB/c mice (female, 8 weeks old, Charles River). After 5 weeks, blood was collected to prepare serum samples. When immunization was carried out twice, the antigen was administered again 4 weeks after the first administration, and blood was collected 2 weeks after the second administration. The anti-HSV antibodies were determined by the following method.

An inactivated HSV-coated microplate of a human anti-HSV antibody determination kit (Herpes State, Whittaker Bioproducts, Lot No. 002706) was blocked with PBS containing 20% FCS at room temperature for 2 hours, followed by washing 3 times with PBS containing 0.05% Tween 20 (PBS-Tween). To this plate was added 100 µl/well of the serum sample diluted with 20% FCS/40 mM Tris-HCl (pH 7.5)/5% NACl/0.05% Tween 20, followed by incubation at room temperature for 1 hour. The plate was washed 6 times with PBS-Tween, and then 100 µl of a 1,000-fold dilution of a peroxidase-labeled anti-mouse IgG antibody (HPR-conjugated rabbit X mouse IgG [H + L], Zymed Laboratories, Lot No. 80801651) was added to each well, followed by incubation at room temperature for 30 minutes. The plate was washed 6 times with PBS-Tween, and then 100 µl of a substrate solution [2 mg/ml o-phenylenediamine/0.02% $H_2O_2$/0.1M citrate buffer (pH 4.5)] was added to each well, followed by reaction for 10 minutes. After 200 µl of 2N sulfuric acid was added to each well to terminate color development, the absorbance was measured at 492 nm.

(2) Comparison of Antibody Productivity of t-gD with That of t-gD-IL-2

The titer of the anti-HSV antibody in the serum sample was calculated using mouse anti-gD monoclonal antibody M42 [Koji Inoue, *Osaka University Medical Magazine* 36 (No.4), 69 (1987)] as a standard antibody in the following manner. The antibody titer of the M42 antibody (1.9 mg/ml) was arbitrarily defined as to 1900 mU/ml, and the titer of the anti-HSV antibody was determined from the ratio of the dilution of M42 giving the 50% value (about 1) of the maximum absorbance ($\geq 2.0$) given by the 8-fold dilution of M42 to that of the serum sample. Mean values for groups each consisting of 10 mice are shown in Table 2. The range represented by ± shows a standard deviation.

TABLE 2

| Antigen (Dose) | Antibody titer (mU/ml) |
|---|---|
| Control [PBS] | 7 |
| t-gD (1 µg) | <15 |
| t-gD (5 µg) | 9 ± 4 |
| t-gD (1 µg) × 2 | 1,018 ± 1,833 |
| t-gD (1 µg) + IL-2 (0.25 µg) | 23 ± 29 |
| t-gD (5 µg) + IL-2 (1.25 µg) | 35 ± 38 |
| t-gD-IL-2 (1 µg) | 400 ± 292 |
| t-gD-IL-2 (5 µg) | 692 ± 442 |
| t-gD-IL-2 (1 µg) × 2 | 46,183 ± 38,443 |
| t-gD (1 µg)-Alum (125 µg) | 341 ± 267 |
| t-gD (5 µg)-Alum (125 µg) | 481 ± 451 |

As apparent from Table 2, when the antigen was once administered alone (Alum−) t-gD could hardly induce the antibody. However, t-gD-IL-2 significantly exhibited the antibody productivity, even when it was administered once. When the mixtures of t-gD and equimolar rIL-2 were administered once, the slight antibody production was only observed. These results revealed that IL-2 combined with t-gD achieved a strong adjuvant activity. When the Alum adjuvant was used (t-gD-Alum), it was observed that t-gD produced the antibody (341 mU/ml on administration of 1 µg and 481 mU/ml on administration of 5 µg). Compared to the antibody titers (400 mU/ml on administration of 1 µg and 692 mU/ml on administration of 5 µg) given by t-gD-IL-2, it was shown that the adjuvant effect due to IL-2 addition was not less than that of alum (125 µg/mouse).

(3) Determination of Killer Activity.

The killer activity was determined by the $^{51}$Cr releasing method. The preparation of effector cells and the labeling of target cells with $^{51}$Cr were performed according to the methods described in S. Hinuma et al., *Immunology* 159, 251 (1986). Each of t-gD (5 µg), the mixture of t-gD (5 µg) and recombinant human IL-2 (rIL-2) (1.25 µg), and t-gD-IL-2 (5 µg) was dissolved in 200 µl of PBS, and the resulting solutions were abdominally subcutaneously administered to BALB/c mice (4 mice per group). After 5 weeks, spleens were obtained from the mice. The spleens were collected for each group containing a control group to prepare single cell suspension. For stimulation in vitro with HSV-1, HSV-1 strain Miyama having a plaque forming unit (PFU) of about $1\times10^7$ was added to $1.25\times10^8$ spleen cells, followed by incubation at 37° C. for 1 hour. The stimulated cells were suspended in 50 ml of complete RPMI 1640 medium containing 10% FCS, and cultivated in a plastic flask (Nunc) in the presence of 5% $CO^2$ at 37° C. for 5 days. When the cells were not stimulated with HSV-1, the cultivation was similarly conducted without addition of HSV-1 strain Miyama. After the cultivation, the cells were washed by centrifugation. The number of the viable cells was counted, and then the cells were used as the effector cells.

As the target cells, P388, a macrophage cell line of the BALB/c mouse, was used. $3\times10^6$ P388 cells were incubated with HSV-1 strain Miyama having a PFU of about $3\times10^6$ at 37° C. for 1 hour to prepare HSV-1-infected P388 cells. Then, 0.1 mCi sodium chromate solution was added to the HSV-1-infected and non-infected cells to label the cells with $^{51}$Cr.

The spleen cells were added to $1\times10^4$ $^{51}$Cr-labeled P388 cells so as to give an effector cells/target cells ratio (E/T ratio) of 25 to 100, followed by cultivation on a U-type 96-well microplate (Nunc) at 37° C. for 4 hours. The killer activity was calculated from the amount of $^{51}$Cr liberated in the supernatant (200 µl). The determination was carried out twice, and the result was indicated by the mean value of the two determinations. Further, the HSV-1 specific $^{51}$Cr-release (%) was calculated from the following equation:

HSV-1 Specific $^{51}$Cr-Release (%)=[$^{51}$Cr Release from HSV-1-Infected P388 Cells (%)]− [$^{51}$Cr-Release from HSV-1-Uninfected P388 Cells (%)]

The results are shown in Table 3. The HSV-1-specific and nonspecific killer activities were only observed when the spleen cells of mice to which t-gD-IL-2 was administered was stimulated in vitro with HSV-1. This shows that the cellular immunity to HSV-1 is induced by the administration of t-gD-IL-2.

TABLE 3

Induction of HSV-1 Specific and Non-specific Killer Activities by Administration of t-gD-IL-2

| Administration in Vivo | HSV-1 Stimulation | HSV-1 Infection of Target | % $^{51}$Cr Release E/T Ratio | | |
|---|---|---|---|---|---|
| | | | 25 | 50 | 100 |
| Control | − | − | <1 | <1 | <1 |
| | − | + | <1 | <1 | <1 |
| | + | − | <1 | <1 | <1 |
| | + | + | <1 | <1 | <1 |
| t-gD | − | − | <1 | <1 | N$^{Da}$ |
| | − | + | <1 | <1 | <1 |
| | + | − | <1 | <1 | ND |
| | + | + | <1 | <1 | <1 |
| t-gD + rIL-2 | − | − | <1 | <1 | <1 |
| | − | + | <1 | <1 | <1 |
| | + | − | ND | ND | ND |
| | + | + | <1 | <1 | ND |
| t-gD-IL-2 | − | − | <1 | <1 | <1 |
| | − | + | >1 | <1 | <1 |
| | + | − | 14.7 | 19.7 | 24.8 |
| | + | + | 26.5 | 34.3 | 38.7 |
| | | | (11.8)$^b$ | (14.6) | (13.9) |

Figure 15:
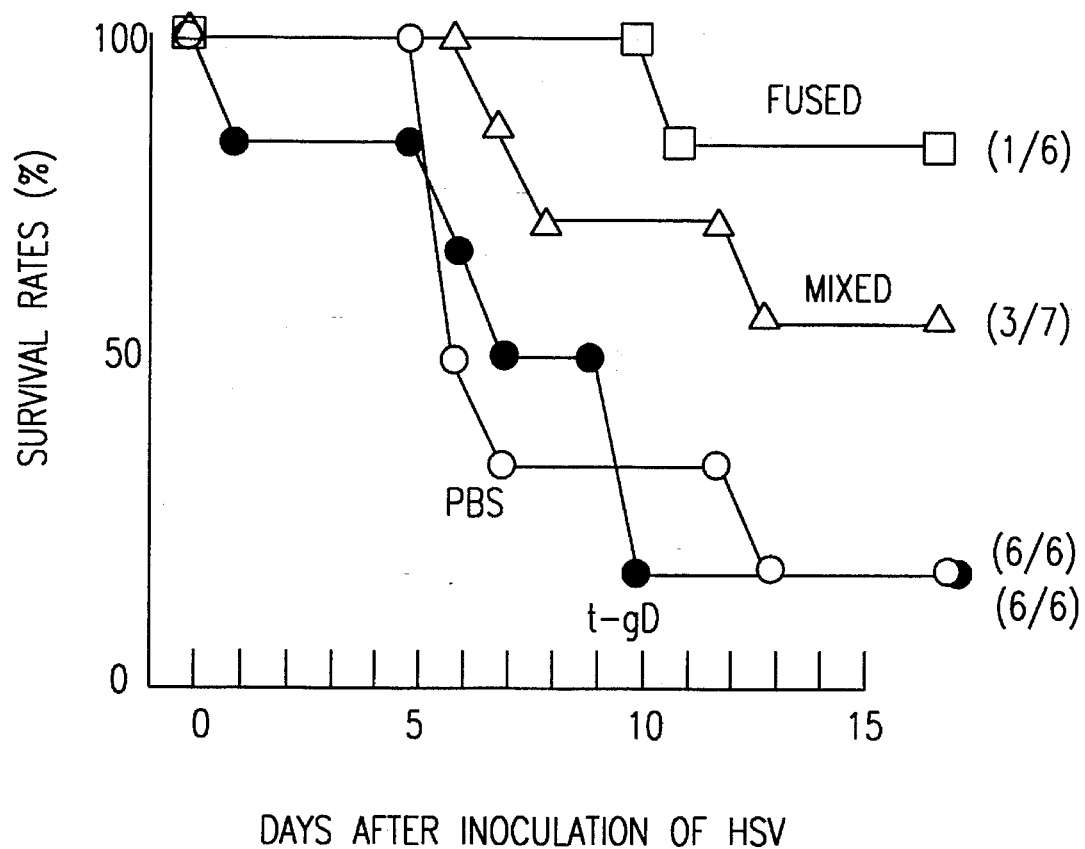
FIG. 15 is a graph showing survival rates of mice to time after inoculation of HSV.
Figure 16A:
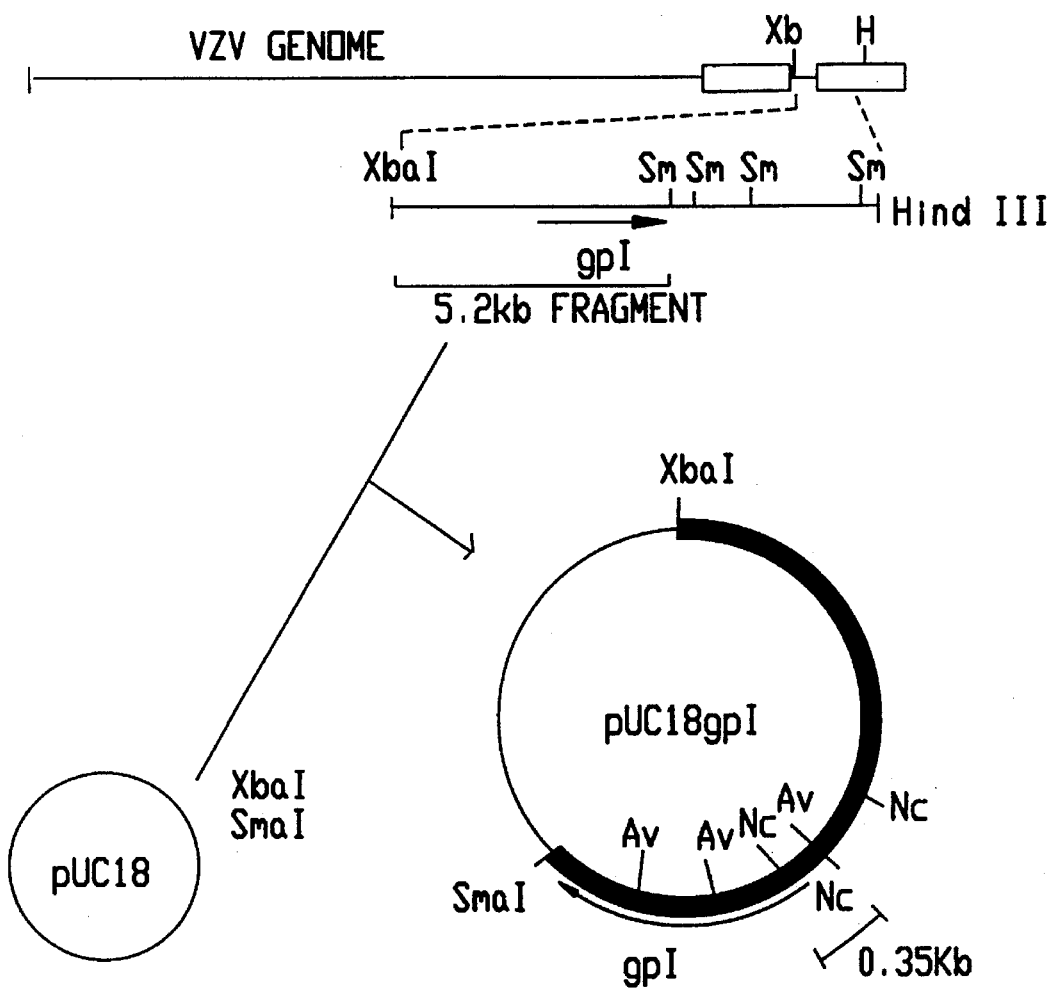
Figure 16B:
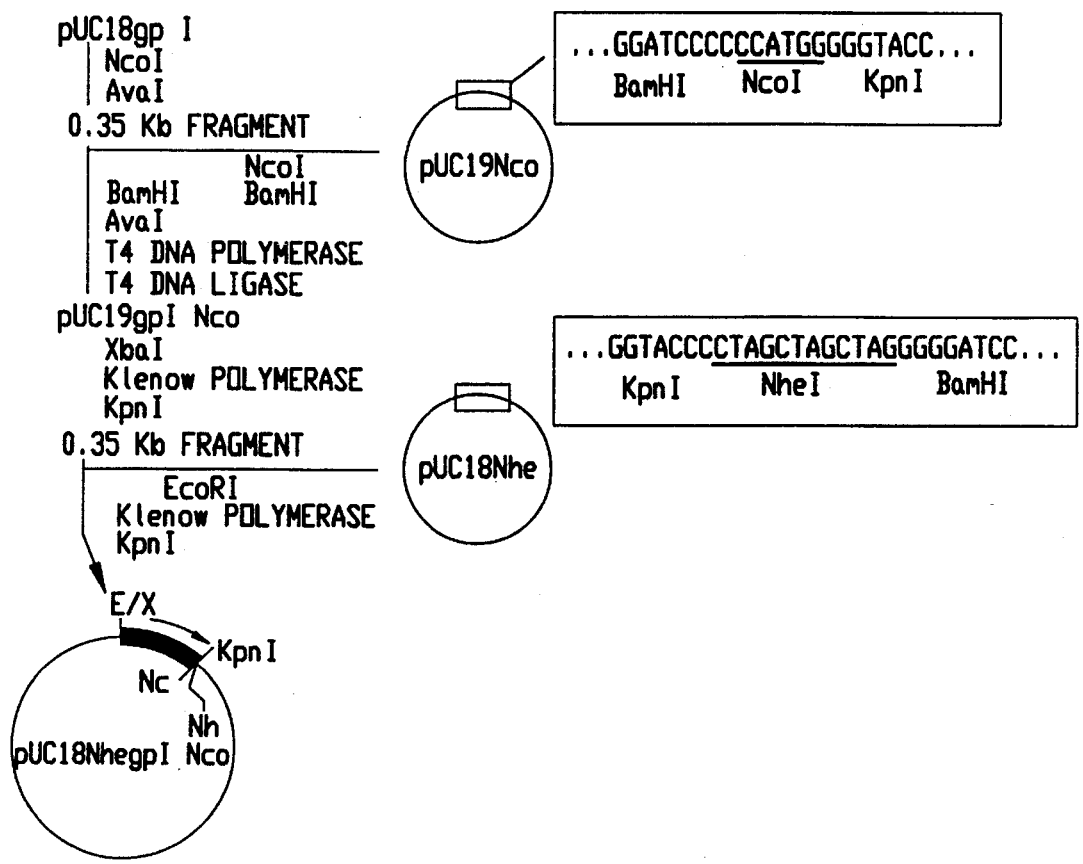
Figure 16C:
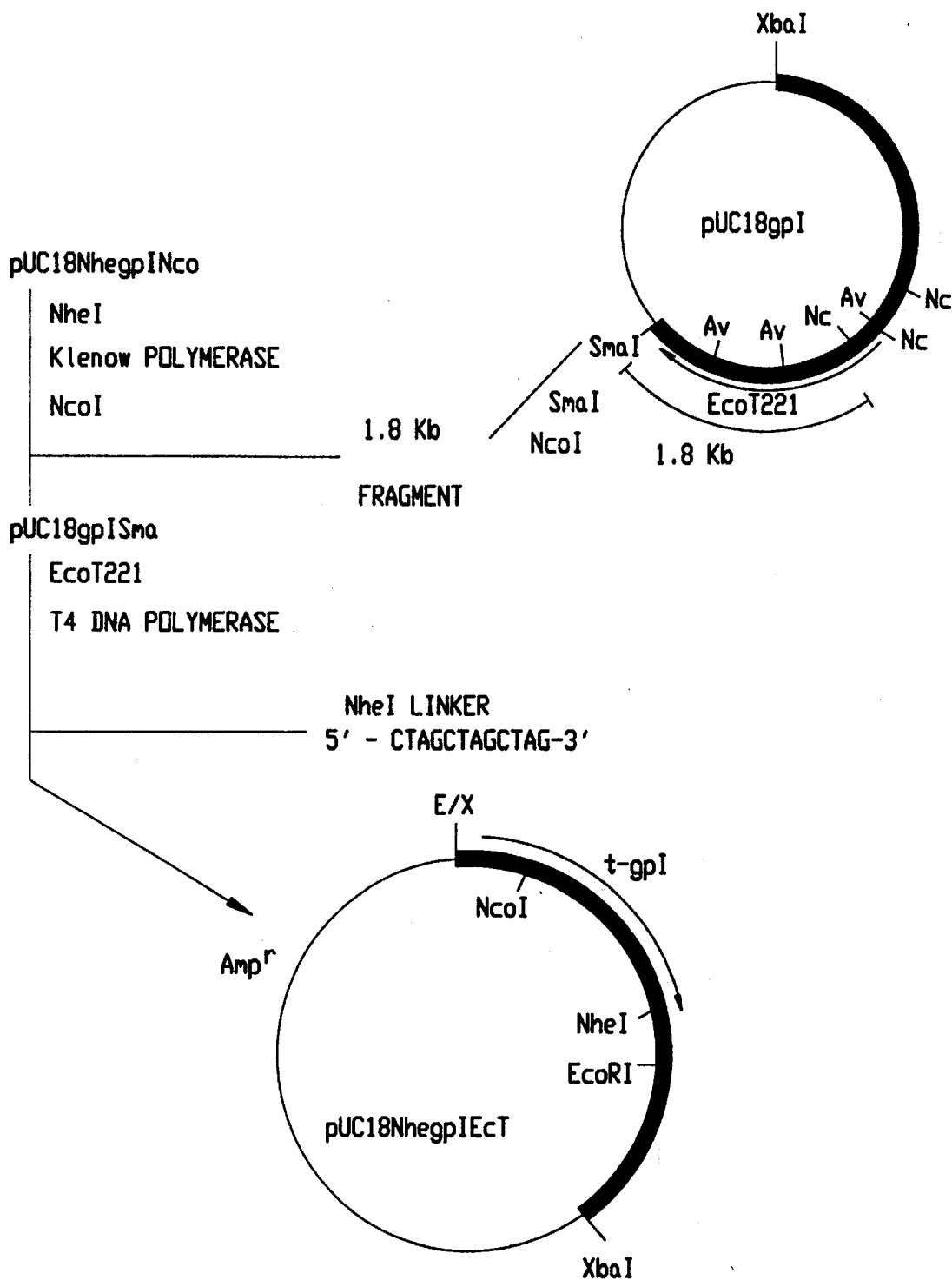
Figure 16D:
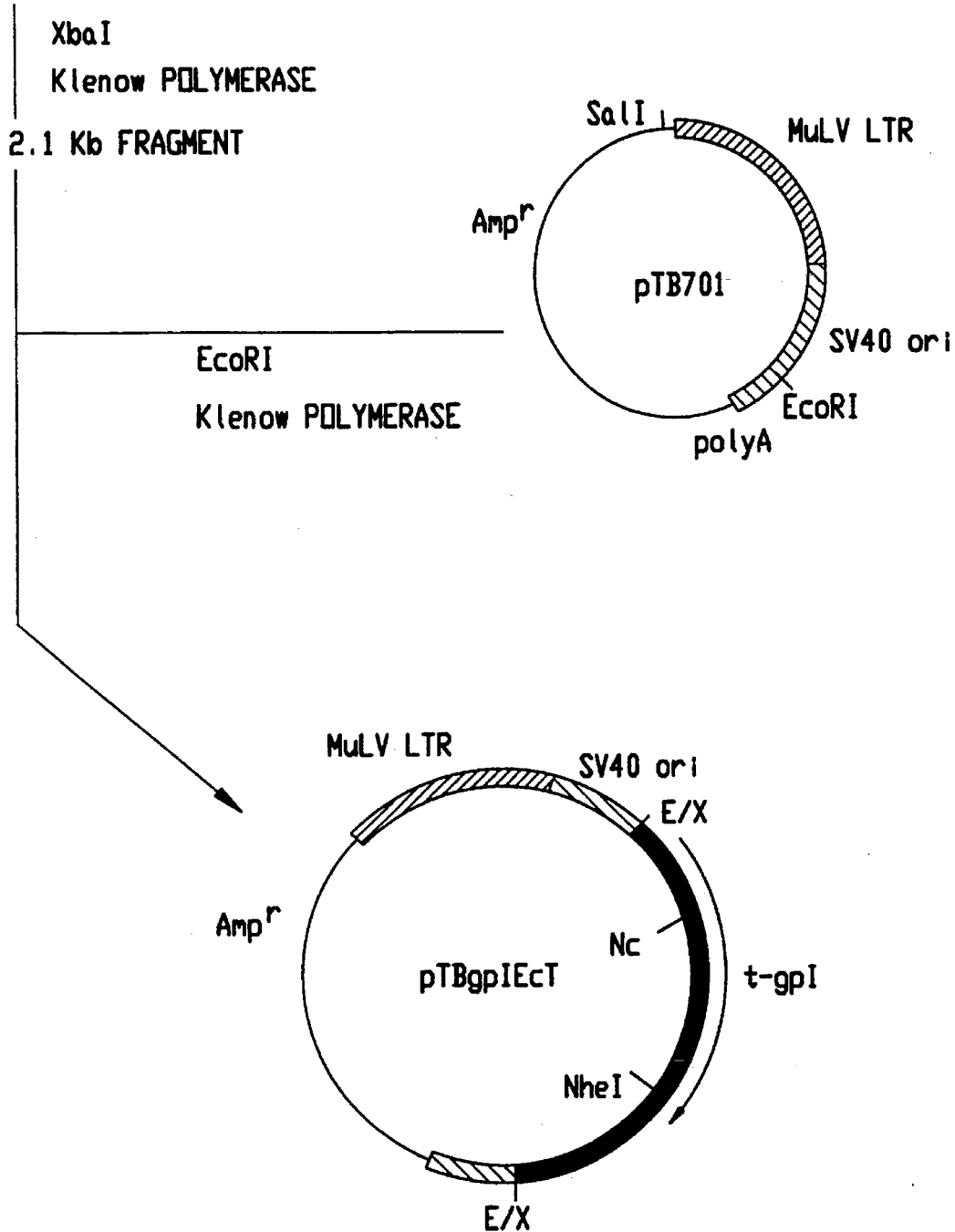
Figure 16F:
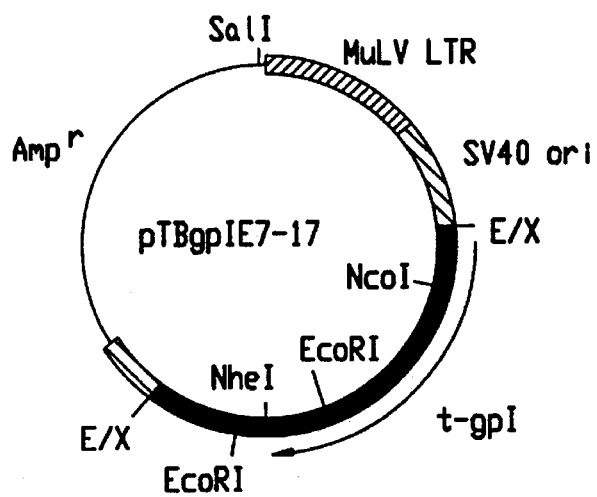
Figure 16G:
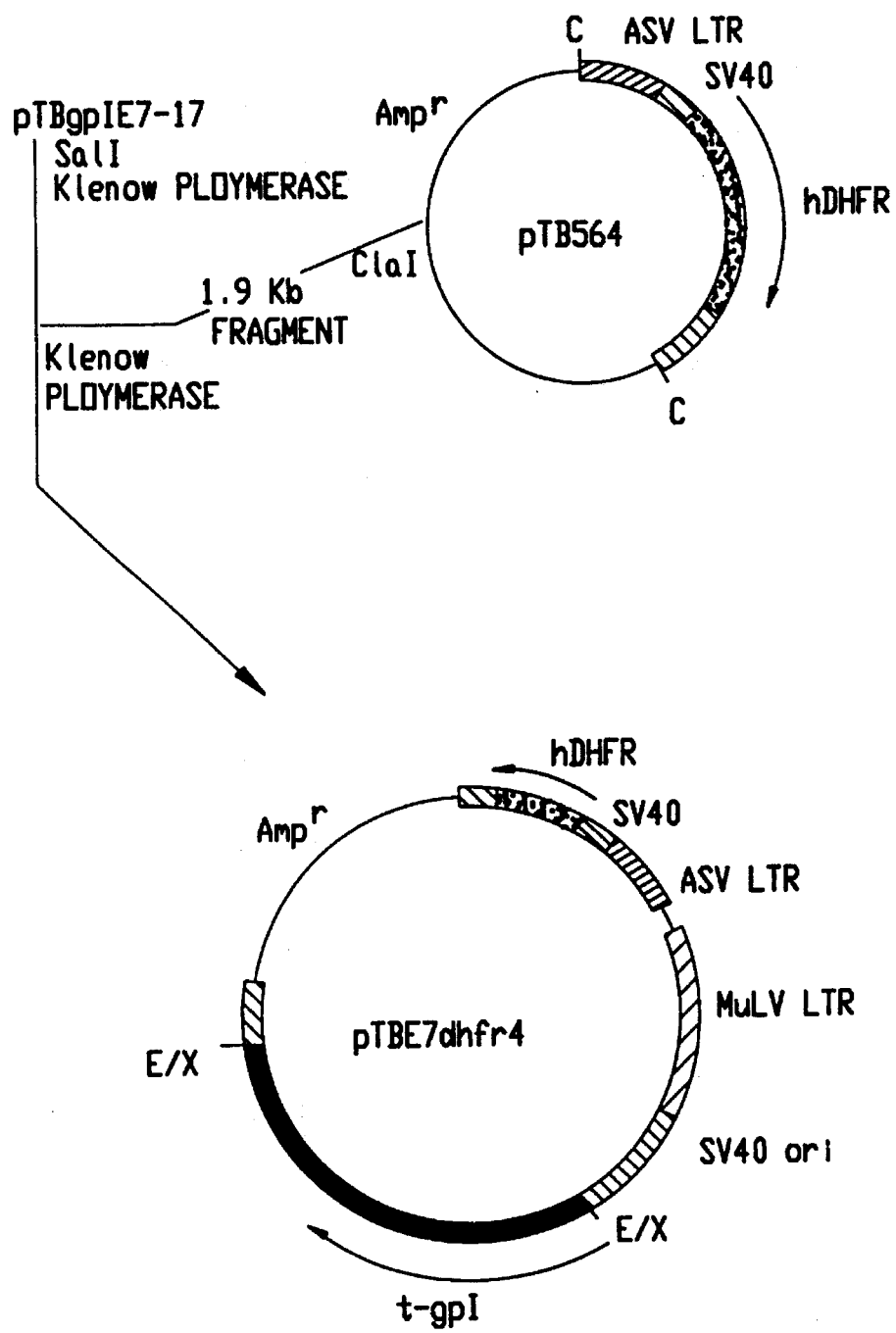

$^a$ND: Not done
$^b$HSV-1 specific $^{51}$Cr releasing amount (4) Protection against HSV-1 Challenge Mice were immunized with each of 1 µg of t-gD, 1 µg of t-gD-IL-2 and a mixture of 1 µg of t-gD and 0.25 µg of rIL-2, and protection against HSV-1 challenge in those mice was examined. Namely, each of the above antigens was administered to 8-week-old female BALB/c mice (a group consisting of 6 to 7 mice) in the manner described in the above item (1). After 5 weeks, 0.1 ml/mouse of HSV-1 (Miyama+ GC strain) having a PFU of $2 \times 10^5$ was intraperitoneally inoculated in the mice. After inoculation, observations were carried out for 17 days to determine the survival ratio of the mice. The results are shown in FIG. 15. The figures in parentheses indicate the number of the mice used and the number of mice in which the symptoms due to HSV-1 infection were observed (the symptoms appeared in the mice or the mice died).

In the control group (PBS) and the t-gD administration group, the symptoms due to HSV-1 infection were observed in all mice. Even in the group (mixed) to which the mixture of t-gD and rIL-2 was administered, about half of the mice died. In contrast, in the t-gD-IL-2 administration group (fused), only one mouse died 11 days after the HSV-1 inoculation.

These results show the effect of IL-2 addition to t-gD not only in antibody production, but also in protection against HSV-1 challenge.

EXAMPLE 14

Preparation of Hybrid Protein Composed of HSV-1 Type Truncated gD and rIL-2

(1) Maleimidation of HSV-1 Truncated gD 1 mg of the HSV truncated gD obtained in Example 11 was dissolved in 2 ml of 5 mM acetate buffer (pH 5.0), and then 50 μl of a bimolar N-(ε-maleimidocaproyloxy)succinimide ester solution in dimetylformamide was added thereto, followed by reaction at 30° C. for 20 minutes. The reaction mixture was subjected to a Sephadex G-25 column equilibrated with 0.1M phosphate buffer (PB, pH 6.5) to remove the combined reagent.

(2) Sulfhydrylation of IL-2

1 mg of the rIL-2 prepared in Japanese Patent Unexamined Publication No. 61-63282/1986 was dissolved in 0.05 M PBS (pH 7.3), and then 50 μl of a bimolar SPDf solution in methanol was added thereto, followed by reaction at 30° C. for 30 minutes. After reduction by addition of 50 μl of 0.1M aqueous solution of DTT, the resulting product was subjected to the Sephadex G-25 column described in the above item (1) to remove the excessive reagent.

(3) Preparation of Antigen-IL-2 Hybrid Protein 0.8 ml of the sulfhydrylated IL-2 prepared in the above item (2) was slowly added to 0.8 mg of the maleimidated truncated gD antigen obtained in the above item (1), with stirring under ice cooling, followed by reaction overnight. The reaction mixture was subjected to a Sephacryl S-200 column to separate and remove unreacted proteins from a chemically combined hybrid protein. As a result, about 1.2 mg of the hybrid protein composed of truncated gD and rIL-2 which were chemically combined with each other was obtained.

EXAMPLE 15

Construction of Gene Expression Plasmid for Fused Protein Composed of Truncated gpI of VZV (Kizuhara Strain) and IL-2

The plasmid pHDLneol which was constructed in Example 7 was partially digested with restriction enzyme NheI, and a DNA fragment of about 7.9 kb which was cleaved only at one site of two NheI sites was isolated. The terminus thereof was changed to a flush end with T4 DNA polymerase. Then, the resulting fragment was digested with NheI again, and a portion of the promoter and the gD region were removed to isolate a residual fragment (fragment (1)).

Figure 18:
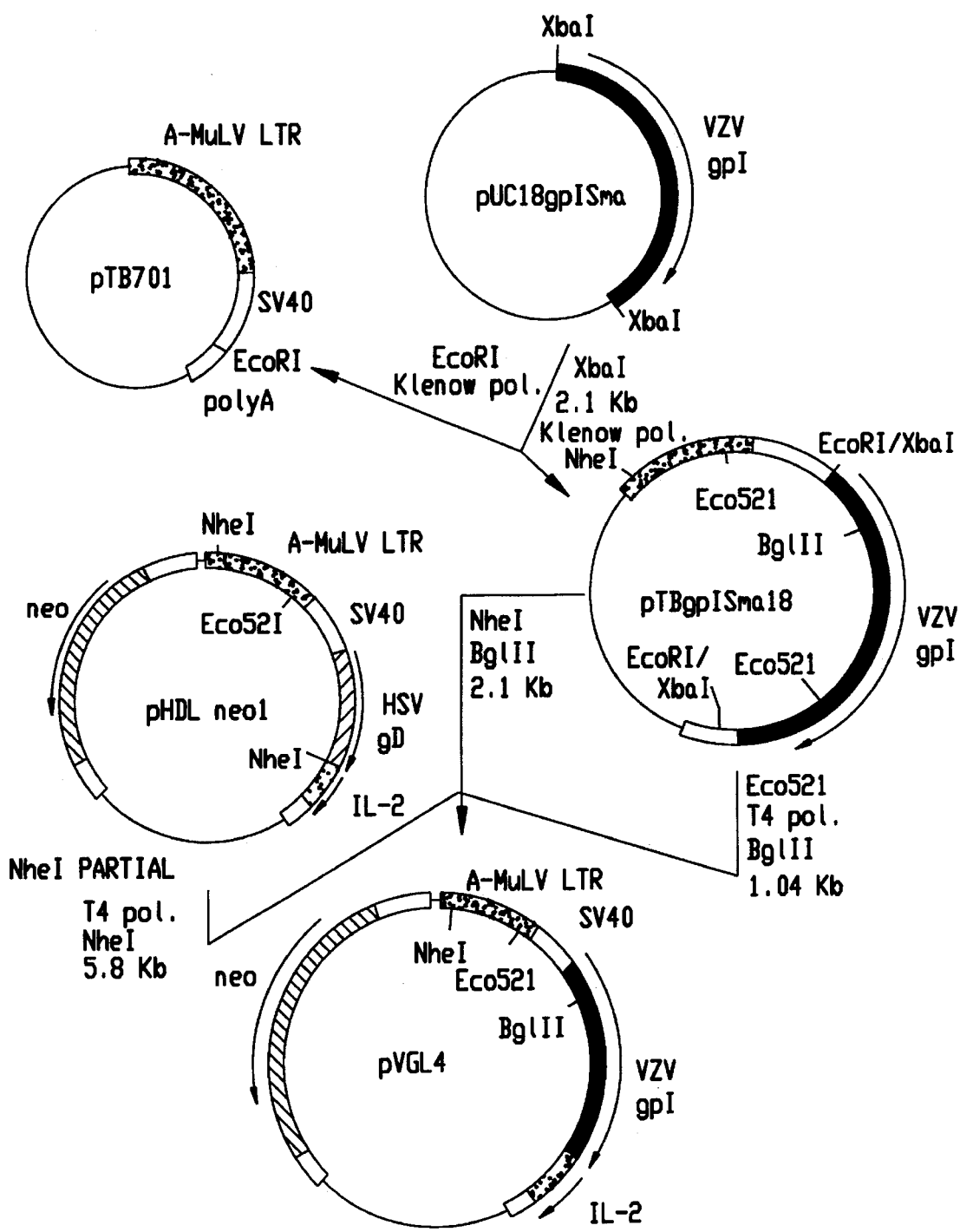
FIG. 18 is a schematic representation showing the construction of an expression plasmid for animal cells of the fused protein gene according to the present invention.

A fragment which was obtained by digesting the plasmid pUC18gpISma containing the VZVgpI gene (Reference Example 2-(3)-ii) with restriction enzyme XbaI was rendered flush with Klenow DNA polymerase, and then inserted into a vector which was obtained by digesting pTB701 (Reference Example 2-(3)iii) with restriction enzyme EcoRI, followed by rendering it flush with Klenow DNA polymerase. Thus, gpI expression plasmid pTBgpISma18 was constructed (FIG. 18). This plasmid was digested with restriction enzyme Eco52I to isolate a fragment coding for the amino acid sequence up to the 515th of gpI, and the termini thereof were changed to flush ends with T4 DNA polymerase. The resulting fragment was digested with restriction enzyme BglII to isolate a 1.04-kb fragment (fragment (2)).

Similarly, pTBgpISma18 was digested with NheI and BglII to isolate a fragment of about 2.1 kb containing a portion of the promoter and a portion of gpI (fragment (3)).

The above three fragments (1), (2) and (3) were ligated to one another with T4 DNA ligase to obtain gene expression plasmid pVGL4 for the fused protein composed of VZV truncated gpI and IL-2 (FIG. 18).

Figure 19:
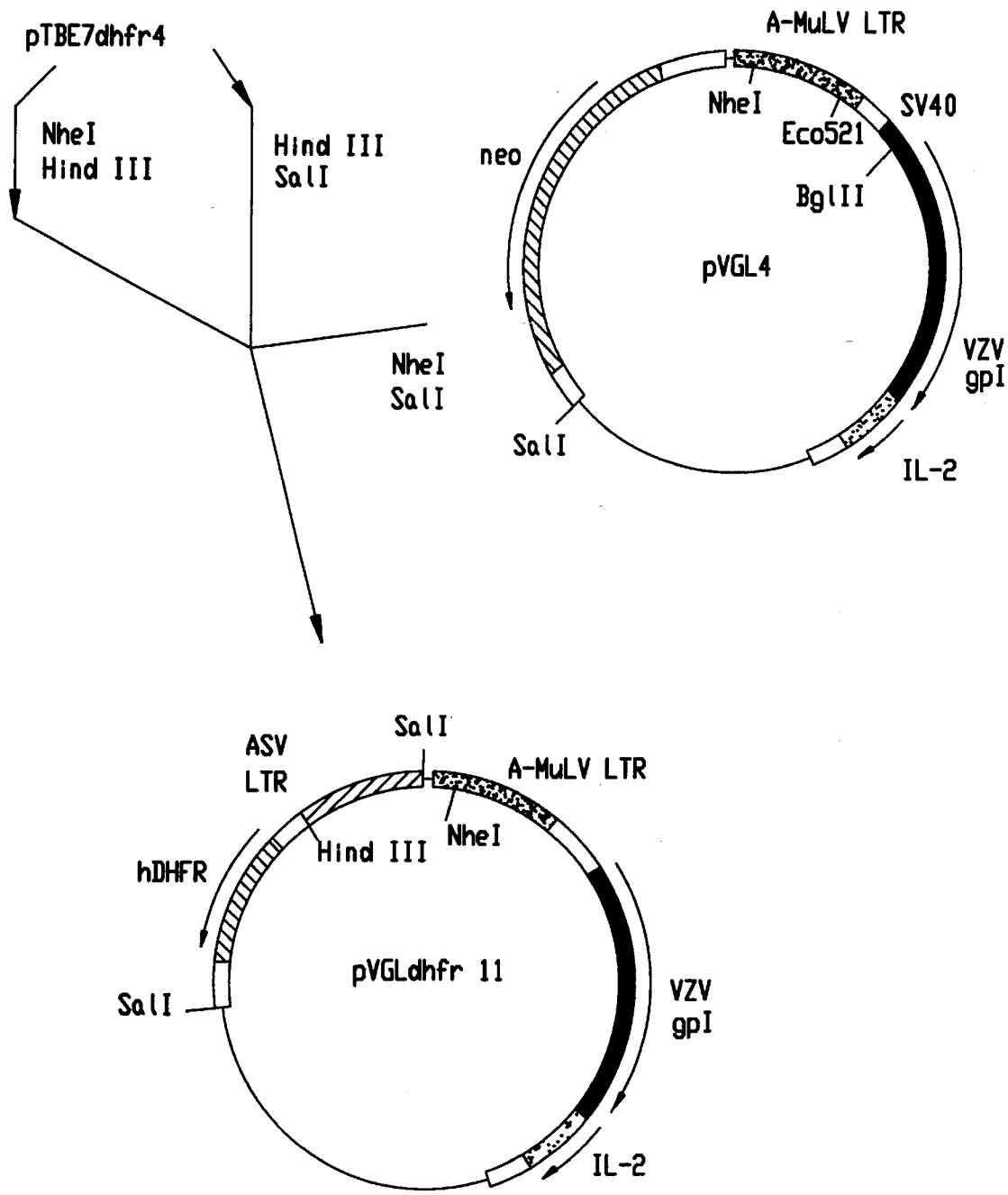
FIG. 19 is a schematic representation showing the construction of an expression plasmid for animal cells of the fused protein gene according to the present invention.

Further, a fragment (containing an ASVLTR promoter) which was obtained by digesting the truncated expression plasmid pTBE7dhfr4 having the hamster dihydrofolate reductase (hDHFR) as a selected marker (Reference Example 2-(4)) with NheI and HindIII, a fragment (containing an hDHFR gene) which was obtained by digesting the plasmid pTBE7dhfr4 with HindIII and SalI, and a fragment which was obtained by digesting pVGL4 with NheI and SalI were ligated to one another with T4 DNA ligase to construct plasmid pVGLdhfr11 (FIG. 19).

EXAMPLE 16

Gene Expression of Fused Protein Composed of VZV Truncated gpI and Il-2 in COS-7 Cell The plasmids pVGL4 and pVGLdhfr11 which were constructed in Example 15 were introduced into COS-7 cells to examine transient expression.

Figure 20A:
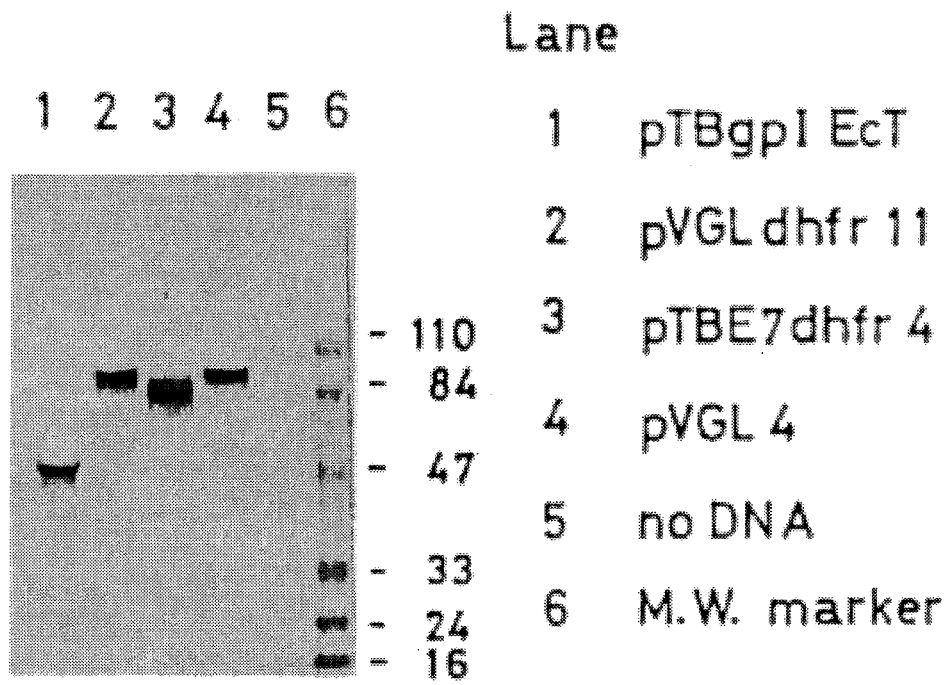
FIGS. 20A and 20B show Western blotting analysis of the fused protein of the present invention.
Figure 20B:
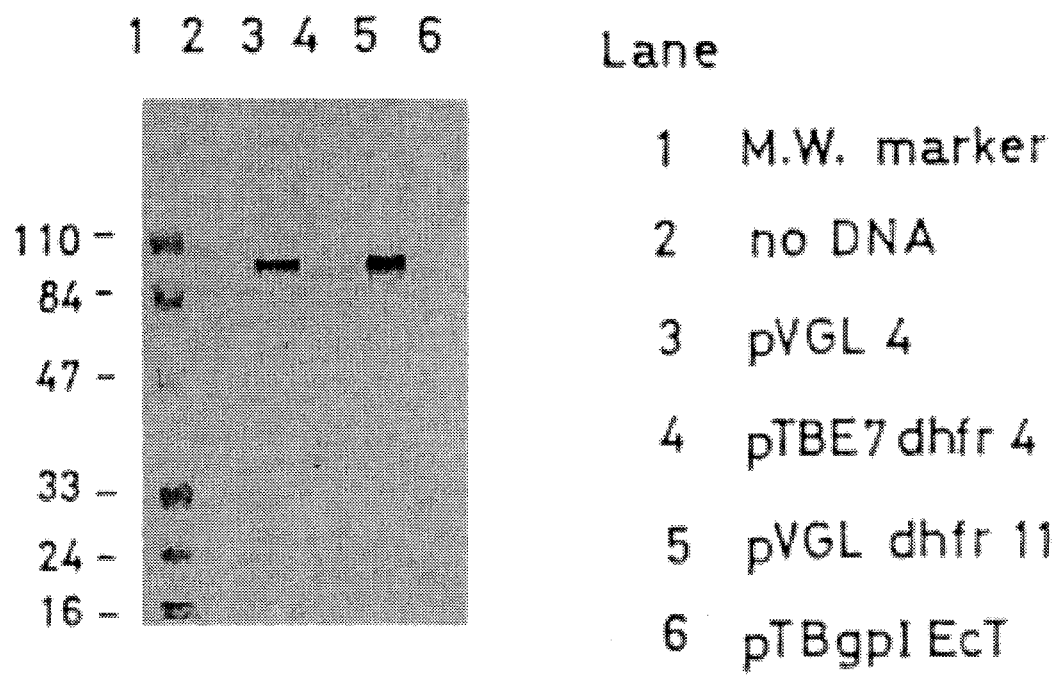

COS-7 cells ($5 \times 10^5$ cells/10 cm dish) were inoculated into 10 ml of Dulbecco's MEM medium (Gibco) containing 10% FCS, and after 18 hours, the cells were transfected with the above plasmids (20 μg/dish) in accordance with the method of Wigler et al. [Cell 16, 777–785 (1979)]. After 24 hours, the resulting cells were incubated on Dulbecco's MEM medium (Gibco) containing 25 mM HEPES (Donin Chemical Laboratory for 2 days. Then, 5 ml of the culture supernatant was concentrated to about 200 μl by a Centricut (Centricut 20, Kurabo Industries). 10 μl of this supernatant was mixed with 5 μl of Laemmli buffer having a 3-fold concentration [final concentrations: 62.5 mM Tris-HCl (pH 8.0), 2% SDS, 10% glycerol, 5% 2-ME, 0.001% BPB], and the mixture was heated at 95° C. for 5 minutes. This sample was subjected to electrophoresis using 10%–20% SDS polyacrylamide gels (Daiichi Kagaku). After electrophoresis, the sample was assayed by the Western blotting method using a mouse anti-gpI monoclonal antibody (which was obtained from a hybridoma prepared by fusing a spleen cell of a BALB/c mouse immunized with a supernatant of VZV-infected cells disrupted by ultrasonication as an immunogen and mouse myeloma cell SP2 with polyethylene glycol) and a rabbit anti-IL-2 antibody (Genzyme). As a result, in the supernatants of the cells into which pVGL4 and pVGLdhfrll were introduced, a band was detected for each of the ant-gpI antibody and the anti-IL-2 antibody (FIGS. 20A abd 20B). On the contrary, in the supernatants of the cells as a control into which pTBE7dhfr4 and pTBgpIEcT (Reference Example 2-(3)-iii) were introduced, a band was only detected for the anti-gpI antibody.

Further, IL-2 biological activity in each supernatant was examined in accordance with the method of Tada et al. [J. Immunol. Methods 93, 157–165 (1986)]. As a consequence, only when pVGL4 and pVGLdhfrll were introduced, the IL-2 activity was observed in the supernatant. This revealed that IL-2 which was fused with gpI had the biological activity (Table 4).

TABLE 4

| Plasmid | IL-2 Activity (U/ml) |
| --- | --- |
| Control | Not detected |
| pVGL4 | 0.27 |
| pTBE7dhfr4 | Not detected |
| pVGLdhfr11 | 0.14 |
| pTBgpIEcT | Not detected |

EXAMPLE 17

Construction of Gene Expression Plasmid for Fused Protein Composed of Human Immunodeficiency Virus (HIV) gag Protein and IL-2

(1) An SalI linker is added to a 5.1-kb AccII-SalI fragment containing the gag-pol region of HIV recombinant proviral clone pNL4-3 [Adachi et al., J. Virol. 59, 284–291 (1986); Gen'Bank R62.0 December 1989, locus HIVNL43], and then the resulting fragment is inserted into the SalI site of pBR322 to prepare plasmid pTB770.

(2) The plasmid pTB770 is digested with restriction enzyme XmnI to isolate a 0.43-kb fragment. This fragment is cleaved with BamHI, and then the cleaved fragment is inserted into pUC8 whose termini are changed to flush ends with T4 DNA polymerase to obtain subclone pUC8Xm3.

The subclone pUC8Xm3 is digested with EcoRI and EcoT22I to isolate a 0.42-kb fragment (fragment (1)).

The plasmid pTB770 is digested with BglII, and then the termini of the digested fragment is changed to flush ends with T4 DNA polymerase, followed by digestion with EcoT22I to isolate a 0.85-kb fragment (fragment (2)).

Plasmid pTB505 [Sasada et al., Cell Structure and Function 13, 129–141 (1988)] for secretory expression of EGF with the signal sequence of IL-2 is digested with EcoRI and SalI to isolate a 1.9-kb fragment (fragment (3)).

The plasmid pHDLneol (refer to Example 5) is digested with NheI, and then the termini of the digested fragment is changed to flush ends with T4 DNA polytmerase, followed by digestion with SalI to isolate a 3.0-kb fragment (fragment (4)).

Figure 21:
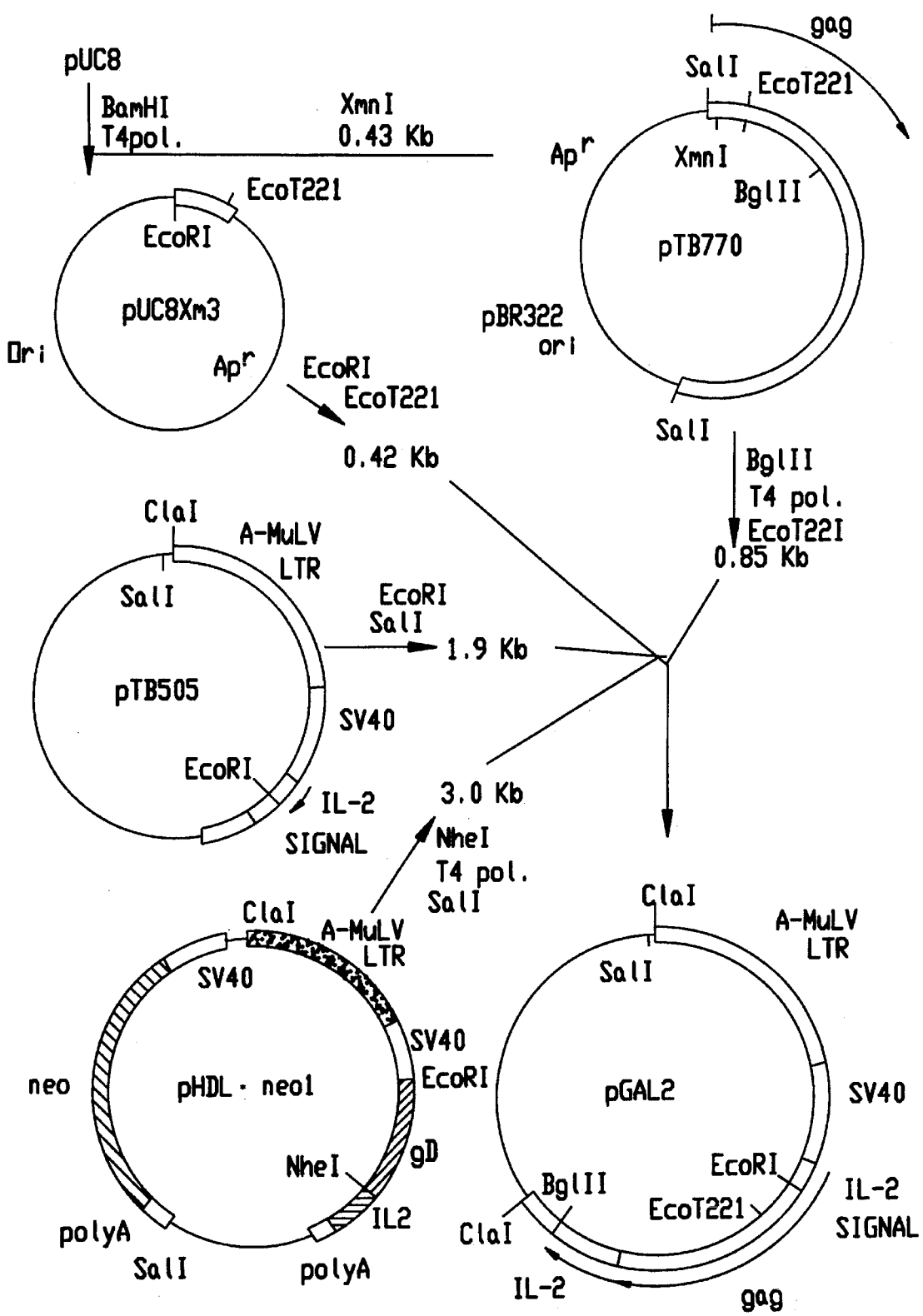
FIG. 21 is a schematic representation showing the construction of an expression plasmid for animal cells of the fused protein gene according to the present invention.

The above four fragments (1), (2), (3) and (4) are ligated to one another with T4 DNA ligase to obtain expression plasmid pGAL2 to which genes each coding for the IL-2 signal sequence (containing the amino acid sequence up to $Gln^{11}$), $Ile^{19}$ to $Ile^{437}$ of the HIV gag protein and $Ala^1$ to $Thr^{133}$ of IL-2 are ligated downstream from an A-MuLV LTR-SV40 promoter (FIG. 21).

(3) Further, in order to modify the plasmid which is obtained in (2) to a stable expression plasmid, the neo-gene of the plasmid pHDLneol is inserted into pGAL2.

The plasmid pHDLneol is digested with ClaI and SalI to isolate a 2.8-kb fragment. This fragment, a 3.6-kb fragment which is obtained by digesting pGAL2 with ClaI and BglII, and a 2.5-kb fragment which is obtained by digesting pGAL2 with SalI and BelII are ligated to one another with T4 DNA ligase to obtain expression plasmid pGALneo (FIG. 22).

With respect to the plasmid obtained according to the above methods, the biological activity of the expressed product can be assayed in the same manner as Example 16. The antigenicity of the expressed product can be confirmed by Western blotting using an anti-gag antibody (Chemicon).

It is understood that the examples and embodiments described herein are for illustrative purposes only and that various modifications or changes in light thereof that will be suggested to persons skilled in the art are to be included in the spirit and purview of this application and the scope of the approved claims.

The following references, which are referred to for their disclosure at various points in this application, are incorporated herein by reference.

Japanese Patent Application No. 63-180114/1988
Japanese Patent Application No. 1-158238/1989
Japanese Patent Application No. 1-308941/1989
Virol. 133, 301 (1984)
J. Virol. 53, 243 (1985)
Japanese Patent Unexamined Publication No. 61-78799/1986
Japanese Patent Unexamined Publication No. 59-93093/1984
Japanese Patent Unexamined Publication No. 60-115528/1985
Mol. Cell. Biol. 4, 771 (1984)
European Patent Publication No. 0235430
Current Genetics, 10, 443C1986
Proc. Natl. Acad. Sci. U.S.A., 75, 1929 (1978)
Virology, 52, 456 (1973 )
Proc. Natl. Acad. Sci. U.S.A., 77, 4505 (1980)
Science, 122, 501 (1952 )
Virology, 8, 396 (1959)
Journal of the American Medical Association, 199, 519 (1967)
Proceeding of the Society for the Biological Medicine, 73, 1 (1950)
J. Gen. Virol. 67, 1759 (1986)
Science 236., 1116–1120 (1987)
Cell Structure and Function 12, 205 (1987)
Japanese Patent Application No. 63-317546/1988
Japanese Patent Unexamined Publication No. 61-63282/1986
Proc. Natl. Acad. Sci. U.S.A. 77, 4216–4220 (1980)
Science 221, 551–553 (1983)
J. Immunol. Methods 93, 157 (1986)
Japanese Patent Application No. 1-233728/1989
Osaka University Medical Magazine 36 (No.4), 69 (1987)
Immunology 159, 251 (1986)

J. Virol. 59, 284–291 (1986)

Cell Structure and Function 13, 129–141 (1988)

What is claimed is:

1. A fused protein comprising a viral antigen and interleukin-2.

2. A fused protein in accordance with claim 1, in which the viral antigen is fused with interleukin-2 through a linker.

3. A fused protein in accordance with claim 1, in which the interleukin 2 is human-derived interleukin 2.

4. A fused protein in accordance with claim 1, in which the viral antigen is a herpesvirus antigen.

5. A fused protein in accordance with claim 4, in which the herpesvirus antigen is a herpes simplex virus antigen or a varicella-zoster virus antigen.

6. A fused protein in accordance with claim 1, in which the viral antigen is a human retrovirus antigen.

7. A fused protein in accordance with claim 6, in which the human retrovirus antigen is a human immunodeficiency virus antigen.

8. A fused protein in accordance with claim 7, in which the human immunodeficiency virus antigen is human immunodeficiency virus gag protein.

9. A fused protein in accordance with claim 1, in which the viral antigen is a herpes simplex virus surface antigen.

10. A fused protein in accordance with claim 9, in which the herpes simplex virus surface antigen is gD or gB of herpes simplex virus type I or type II.

11. A fused protein in accordance with claim 10, in which the gD or the gB is gD or gB lacking a transmembrane domain.

12. A fused protein in accordance with claim 1, in which a herpes simplex virus surface antigen is arranged on the amino terminal side and interleukin 2 is arranged on the carboxyl terminal side.

13. A pharmaceutical composition which comprises a fused protein in accordance with claim 1 and a pharmaceutically acceptable carrier.

14. A hybrid protein obtained by chemically coupling a viral antigen and interleukin-2.

15. A hybrid protein in accordance with claim 14, in which the viral antigen is a herpes simplex virus surface antigen.

16. A hybrid protein in accordance with claim 14 in which the viral antigen is a human retrovirus antigen.

17. A hybrid protein in accordance with claim 16, in which the human retrovirus antigen is a human immunodeficiency virus antigen.

18. A hybrid protein in accordance with claim 14, wherein the interleukin-2 is human interleukin-2.

19. A hybrid protein in accordance with claim 14, in which the viral antigen is a human immunodeficiency virus gag protein.

20. A pharmaceutical composition which comprises a hybrid protein obtained by chemically coupling a vital antigen with interleukin-2, and a pharmaceutically acceptable carrier.

* * * * *